US012570647B2

(12) United States Patent
Walker et al.

(10) Patent No.: US 12,570,647 B2
(45) Date of Patent: Mar. 10, 2026

(54) AMINO BENZOTHIAZOLE COMPOUNDS FOR TREATMENT OF ANTIBIOTIC RESISTANT BACTERIA

(71) Applicants: Saint Louis University, St. Louis, MO (US); United States Government as Represented by the Department of Veterans Affairs, Washington, DC (US)

(72) Inventors: John K. Walker, St. Louis, MO (US); Feng Cao, St. Louis, MO (US); Terri Boehm, Ballwin, MO (US); Kinthada Ramakumar, St. Louis, MO (US)

(73) Assignees: Saint Louis University, St. Louis, MO (US); United States Government as Represented by the Department of Veterans Affairs, Washington, DC (US)

( * ) Notice: Subject to any disclaimer, the term of this patent is extended or adjusted under 35 U.S.C. 154(b) by 67 days.

(21) Appl. No.: 17/578,616

(22) Filed: Jan. 19, 2022

(65) Prior Publication Data

US 2022/0267312 A1 Aug. 25, 2022

Related U.S. Application Data

(60) Provisional application No. 63/139,114, filed on Jan. 19, 2021.

(51) Int. Cl.

*C07D 417/04* (2006.01)
*A61P 31/04* (2006.01)
*C07D 417/12* (2006.01)
*C07D 417/14* (2006.01)

(52) U.S. Cl.

CPC ............ *C07D 417/04* (2013.01); *A61P 31/04* (2018.01); *C07D 417/12* (2013.01); *C07D 417/14* (2013.01)

(58) Field of Classification Search

CPC .. C07D 417/04; C07D 417/12; C07D 417/14; A61P 31/04
USPC .................................................... 514/254.02
See application file for complete search history.

(56) References Cited

U.S. PATENT DOCUMENTS

2019/0134056 A1* 5/2019 Tolias .................. A61K 31/536

FOREIGN PATENT DOCUMENTS

JP 2869561 B2 * 3/1999
WO WO-2010024903 A1 * 3/2010 ........... C07D 417/04
WO WO-2018201146 A1 * 11/2018 ......... A61K 31/4402
WO WO-2021247921 A1 * 12/2021 ........... C07D 487/04

OTHER PUBLICATIONS

Foscolos et al. Annales Pharmaceutiques Francaises (1977), 35(7-8), 295-307.*

Foscolos et al. Annales Pharmaceutiques Francises (1977), 35(7-8), 295-307.*

Reynolds et al. Tuberculosis (Oxford, United Kingdom), 2012, 92(1), 72-83.*

Annadurai et al., "Design and synthesis of 2-aminothiazole based antimicrobials targeting MRSA", *Bioorganic & Medicinal Chemistry Letters*, 22, pp. 7719-7725, 2012.

Cao et al., "Synthesis and Evaluation of Troponoids as a New Class of Antibiotics", *ACS Omega*, 3(11):15125-133, 2018.

Chohan et al., Zinc Complexes of Benzothiazole-derived Schiff Bases with Antibacterial Activity, *Journal of Enzyme Inhibition and Medicinal Chemistry*, 18(3), pp. 259-263, 2003.

Fajkusova et al., "Anti-infective and herbicidal activity of N-substituted 2-aminobenzothiazoles", *Bioorganic & Medicinal Chemistry*, 20, pp. 7059-7068, 2012.

Gawad et al., "Design, synthesis and biological evaluation of some 2-(6-nitrobenzo[d]thiazol-2-ylthio)-N-benzyl-N-(6-nitrobenzo[d]thiazol-2-yl)acetamide derivatives as selective DprE1 inhibitors", *Synthetic Communications*, 49(20):2696-2708, 2019.

Kavanagh, "Control of MSSA and MRSA in the United States: protocols, policies, risk adjustment and excuses", *Antimicrobial Resistance & Infection Control*, 8:103, 2019.

Peeters et al., "The impact of initial antibiotic treatment failure: real-world insights in patients with complicated, health care—associated intra-abdominal infection", *Infect. Drug Resist.*, 12:329-343, 2019.

Reynolds, et al., "High throughput screening of a library based on kinase inhibitor scaffolds against Mycobacterium tuberculosis H37Rv", *Tuberculosis*, 92(1):72-83, 2012.

Sharma et al., "Synthesis and antibacterial evaluation of novel analogs of fluoroquinolones annulated with 6-substituted-2-aminobenzothhiazoles", *Arabian Journal of Chemistry*, 8, pp. 671-677, 2015.

Soni et al., "Synthesis and evaluation of some new benzothiazole derivatives as potential antimicrobial agents", *European Journal of Medicinal Chemistry*, 45, 2938-2943, 2010.

Srivastava et al., "Synthesis and biological evaluation of 2-aminobenzothiazole derivatives", *Indian Journal of Chemistry*, 47B, pp. 1583-1586, 2008.

(Continued)

*Primary Examiner* — Kahsay Habte
(74) *Attorney, Agent, or Firm* — pH IP Law

(57) ABSTRACT

Provided herein are compounds of the formula:

(I)

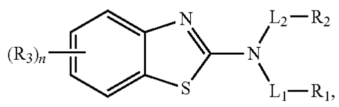

wherein the variables are as defined herein. Pharmaceutical compositions of the compounds are also provided. In some aspects, these compounds may be used for the treatment of diseases or disorders, such as an infection of an antibiotic resistant bacteria.

14 Claims, No Drawings

(56) References Cited

OTHER PUBLICATIONS

Umei et al., "Identification of novel 1,2,3,6-tetrahydropyridyl-substituted benzo[d]thiazoles: Lead generation and optimization toward potent and orally active $EP_1$ receptor antagonists", *Bioorg & Med. Chem.*, 25(13):3406-3430, 2017.

Von Bubnoff, "Seeking New Antibiotics in Nature's Backyard", *Cell*, 127(5):867-869, 2006.

Wright et al., "The evolving role of chemical synthesis in antibacterial drug discovery", *Angew Chem. Int. Ed.*, 53(34):8840-8869, 2014.

* cited by examiner

AMINO BENZOTHIAZOLE COMPOUNDS FOR TREATMENT OF ANTIBIOTIC RESISTANT BACTERIA

This application claims the benefit of priority to U.S. Provisional Application No. 63/139,114, filed on Jan. 19, 2021, the entire contents of which are hereby incorporated by reference.

This invention was made with government support under Grant no. R01 AI136799-01 awarded by the National Institutes of Health. The government has certain rights in the invention.

BACKGROUND

I. Field

The present disclosure relates generally to the fields of antibiotics. More particularly, it concerns compound useful in the treatment of antibiotic resistant bacterial infections.

II. Description of Related Art

Pandemics arising from a microorganisms are an emerging threat to the global population. While there are threats from a host of microorganisms such as virus, bacteria, and parasites, these threats are particularly relevant in bacteria which can quickly evolve and become resistant to front line treatments. This evolution of bacteria and their ability to develop resistant to antibiotics has lead to the rise of super-bugs such as methicillin-resistant *Staphylococcus aureus* (MRSA) and other bacteria resistant to a wide range of antibiotic treatments that have proven difficult to treat clinically. (Wright et al., 2014; von Bubnoff, 2006; Peeters et al., 2019). This is spawning serious public health concerns including the threat of further pandemics of infections that are not treatable. Cost effective strategies for overcoming antibiotic resistance and new agents that operate via different mechanisms of action may help alleviate some of these concerns. In particular, MRSA causes a significant strain on our hospital system and Staph infections resulted in almost 20,000 deaths in 2017 in the US. (Kavanagh, 2019). Therefore, there remains a need to develop new compounds that are useful in the treatment of antibiotic resistant bacterial infections such as MRSA.

SUMMARY OF THE INVENTION

The present disclosure provides compounds that may be used to treat an infection of an antibiotic resistant bacteria such as MRSA. In still yet another aspect, the present disclosure provides compounds of the formula:

(I)

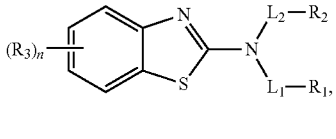

wherein:

n is 0, 1, 2, 3, or 4;

$L_1$ is a covalent bond, —C(O)—, or —$S(O)_2$—; or -alkanediyl$_{(C\le 12)}$-, -alkenediyl$_{(C\le 12)}$-, -alkynediyl$_{(C\le 12)}$-, —C(O)-alkenediyl$_{(C\le 12)}$-, or a substituted version of any of these groups; or $L_1$ and $R_1$ are taken together and is an amino acid residue or a monoprotected amino acid residue;

$R_1$ is alkyl$_{(C\le 12)}$, cycloalkyl$_{(C\le 12)}$, heterocycloalkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any one of these groups; or $R_1$ and $L_1$ are taken together and are as defined above;

$L_2$ is -alkanediyl$_{(C\le 12)}$- or substituted -alkanediyl$_{(C\le 12)}$-;

$R_2$ is heterocycloalkyl$_{(C\le 12)}$, substituted heterocycloalkyl$_{(C\le 12)}$, heteroaryl$_{(C\le 12)}$, substituted heteroaryl$_{(C\le 12)}$, heteroarylium$_{(C\le 12)}$, or substituted heteroarylium$_{(C\le 12)}$; or $L_1$-$R_1$ and $L_2$-$R_2$ are taken together and form a cycloalkanediyl$_{(C\le 12)}$, substituted cycloalkanediyl$_{(C\le 12)}$, heterocycloalkanediyl$_{(C\le 12)}$, substituted heterocycloalkanediyl$_{(C\le 12)}$, cycloalkanediyl$_{(C\le 12)}$ substituted with $R_4$, heterocycloalkanediyl$_{(C\le 12)}$ substituted with $R_4$, wherein $R_4$ is -alkanediyl$_{(C\le 12)}$-heteroaryl$_{(C\le 12)}$ or substituted -alkanediyl$_{(C\le 12)}$-heteroaryl$_{(C\le 12)}$;

$R_3$ is, in each instance independently, amino, cyano, halo, hydroxy, or nitro; or alkyl$_{(C\le 12)}$, cycloalkyl$_{(C\le 12)}$, heterocycloalkyl$_{(C\le 12)}$, aryl$_{(C\le 12)}$, heteroaryl$_{(C\le 12)}$, alkoxy$_{(C\le 12)}$, alkylamino$_{(C\le 12)}$, dialkylamino$_{(C\le 12)}$, or a substituted version of any one of these groups;

provided the compound is not N-(3-(1H-imidazol-1-yl)propyl)-N-(6-chloro-4-methylbenzo[d]thiazol-2-yl)furan-2-carboxamide.

or a pharmaceutically acceptable salt thereof.

In some embodiments, the compounds are further defined:

(II)

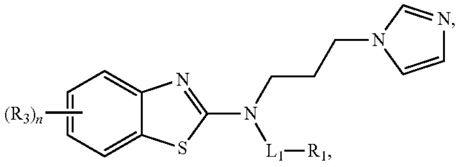

wherein:

n is 0, 1, 2, 3, or 4;

$L_1$ is a covalent bond, —C(O)—, or —$S(O)_2$—; or -alkanediyl$_{(C\le 12)}$-, -alkenediyl$_{(C\le 12)}$-, -alkynediyl$_{(C\le 12)}$-, —C(O)-alkenediyl$_{(C\le 12)}$-, or a substituted version of any of these groups; or $L_1$ and $R_1$ are taken together and are an amino acid residue or a monoprotected amino acid residue;

$R_1$ is alkyl$_{(C\le 12)}$, cycloalkyl$_{(C\le 12)}$, heterocycloalkyl$_{(C\le 12)}$, aryl$_{(C\le 12)}$, aralkyl$_{(C\le 12)}$, heteroaryl$_{(C\le 12)}$, heteroaralkyl$_{(C\le 12)}$, or a substituted version of any one of these groups; or $R_1$ and $L_1$ are taken together and is as defined above; and $R_3$ is, in each instance independently, amino, cyano, halo, hydroxy, or nitro; or alkyl$_{(C\le 12)}$, cycloalkyl$_{(C\le 12)}$, heterocycloalkyl$_{(C\le 12)}$, aryl$_{(C\le 12)}$, heteroaryl$_{(C\le 12)}$, alkoxy$_{(C\le 12)}$, alkylamino$_{(C\le 12)}$, dialkylamino$_{(C\le 12)}$, or a substituted version of any one of these groups;

provided the compound is not N-(3-(1H-imidazol-1-yl)propyl)-N-(6-chloro-4-methylbenzo[d]thiazol-2-yl)furan-2-carboxamide.

or a pharmaceutically acceptable salt thereof.

In some embodiments, the compounds are further defined:

(III)

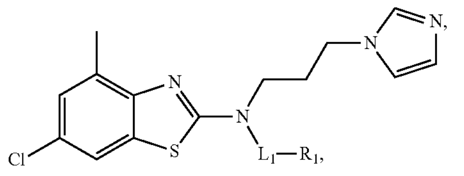

wherein:

$L_1$ is a covalent bond, —C(O)—, or —$S(O)_2$—; or -alkanediyl$_{(C\leq12)}$-, -alkenediyl$_{(C\leq12)}$-, -alkynediyl$_{(C\leq12)}$-, —C(O)-alkenediyl$_{(C\leq12)}$-, or a substituted version of any of these groups; or $L_1$ and $R_1$ are taken together and is an amino acid residue or a monoprotected amino acid residue; and $R_1$ is alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any one of these groups; or $R_1$ and $L_1$ are taken together and is as defined above;

provided the compound is not N-(3-(1H-imidazol-1-yl)propyl)-N-(6-chloro-4-methylbenzo[d]thiazol-2-yl)furan-2-carboxamide.

or a pharmaceutically acceptable salt thereof.

In some embodiments, $L_2$ is -alkanediyl$_{(C\leq12)}$- such as -propanediyl-. In some embodiments, $R_2$ is heteroarylium$_{(C\leq12)}$ such as 3-methyl-1H-imidazol-3-ium-1-yl. In other embodiments, $R_2$ is heteroaryl$_{(C\leq12)}$ such as 1H-imidazol-1-yl. In other embodiments, $R_2$ is heterocycloalkyl$_{(C\leq12)}$ such as N-methylpiperidinyl, piperidinyl, or pyrolidinyl. In some embodiments, n is 0, 1, or 2, specifically, n is 2. In some embodiments, $R_3$ is halo such as chloro. In other embodiments, $R_3$ is alkyl$_{(C\leq12)}$ such as methyl.

In some embodiments, $L_1$ is a covalent bond. In other embodiments, $L_1$ is —C(O)—. In other embodiments, $L_1$ is —$S(O)_2$—. In other embodiments, $L_1$ is -alkanediyl$_{(C\leq12)}$- such as methanediyl. In other embodiments, $L_1$ is —C(O)-alkenediyl$_{(C\leq12)}$- such as —C(O)—CHCH—. In other embodiments, $L_1$ and $R_1$ are taken together and is a monoprotected amino acid residue such as $L_1$ and $R_1$ are taken together and is N-Boc-phenylalanine.

In some embodiments, $R_1$ is alkyl$_{(C\leq12)}$ such as isopropyl. In some embodiments, $R_1$ is cycloalkyl$_{(C\leq12)}$ such as cyclopropyl, cyclobutyl, cyclopentyl, cyclohexyl, or 1-methylcycloprop-1-yl. In other embodiments, $R_1$ is heterocycloalkyl$_{(C\leq12)}$ such as tetrahydrofuran-2-yl. In other embodiments, $R_1$ is aryl$_{(C\leq12)}$ or substituted aryl$_{(C\leq12)}$. In some embodiments, $R_1$ is aryl$_{(C\leq12)}$ such as phenyl. In other embodiments, $R_1$ is substituted aryl$_{(C\leq12)}$ such as p-carboxyphenyl. In other embodiments, $R_1$ is heteroaryl$_{(C\leq12)}$ or substituted heteroaryl$_{(C\leq12)}$. In some embodiments, $R_1$ is heteroaryl$_{(C\leq12)}$ such as pyrrol-2-yl, furan-2-yl, furan-3-yl, 3-methylfuran-2-yl, 2-methylfuran-5-yl, 2,3-dimethylfuran-5-yl, benzofuran-2-yl, thiophen-2-yl, 2-methylthiophen-5-yl, or pyridin-2-yl. In other embodiments, $R_1$ is substituted heteroaryl$_{(C\leq12)}$ such as 2-((methylthio)methyl)furan-5-yl.

In some embodiments, the compounds are further defined as:

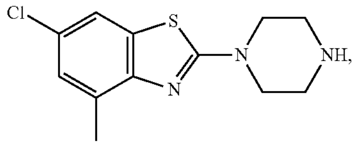

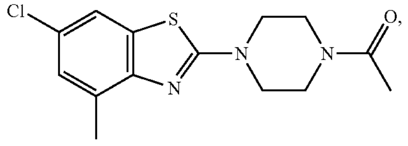

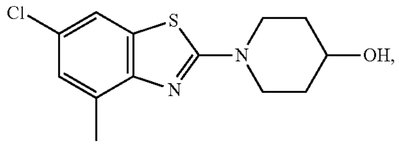

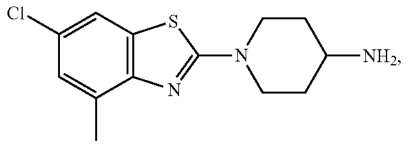

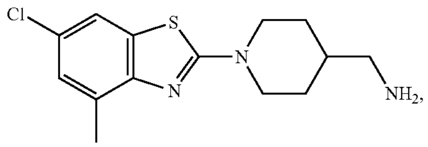

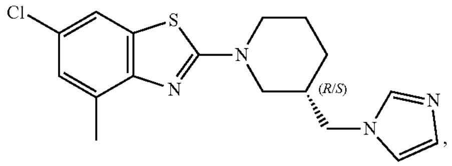

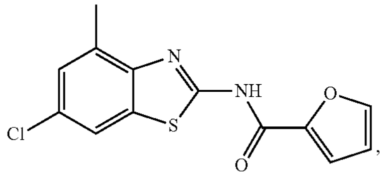

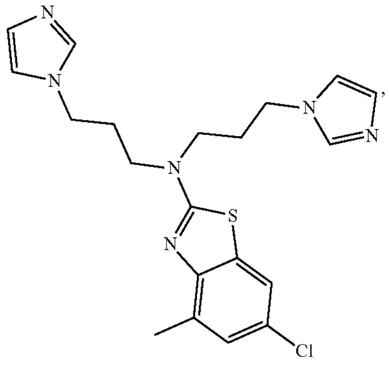

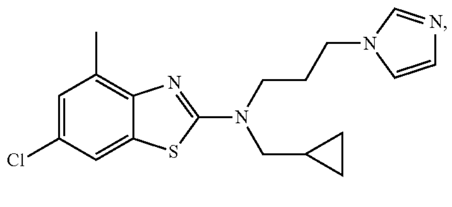

-continued
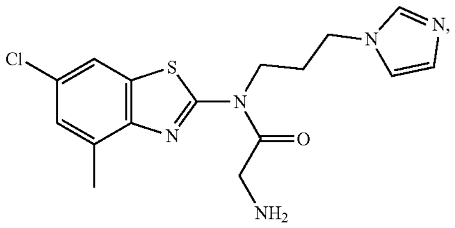
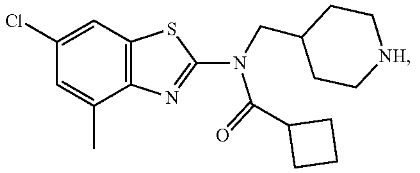
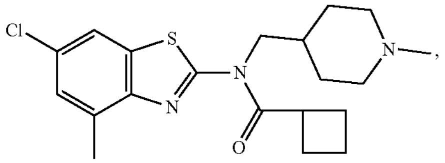
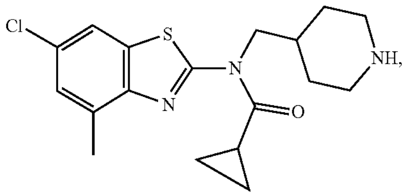
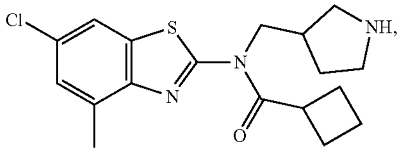
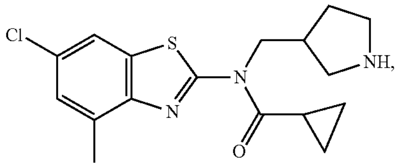
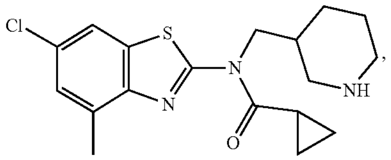
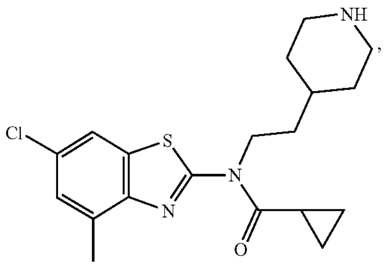
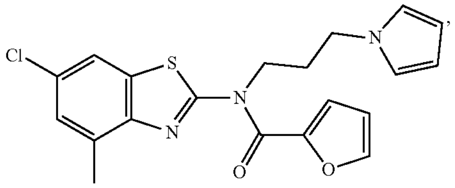
-continued
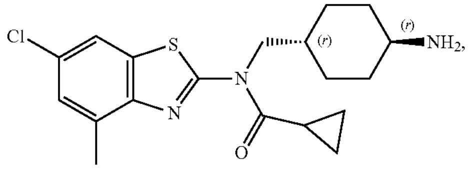
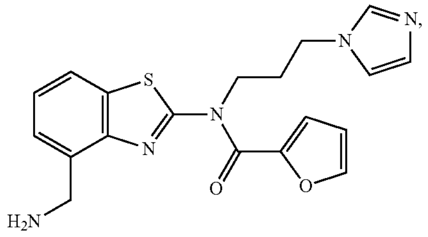
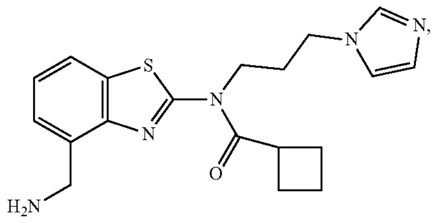
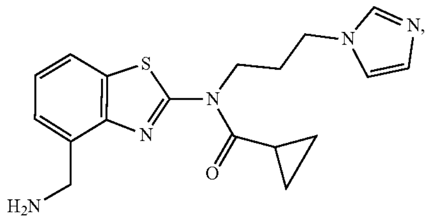
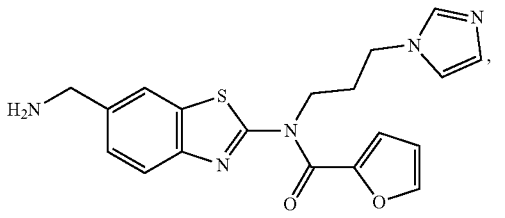
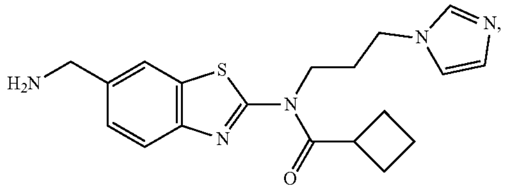
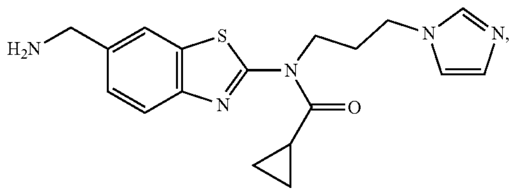
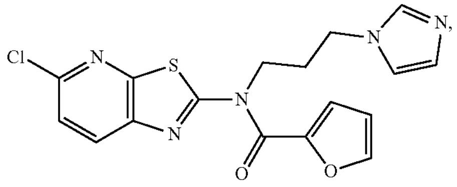

-continued
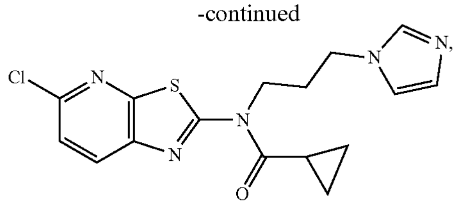
,
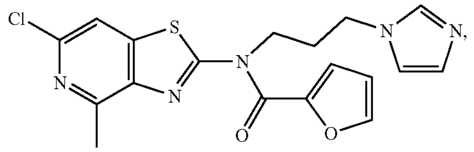
,
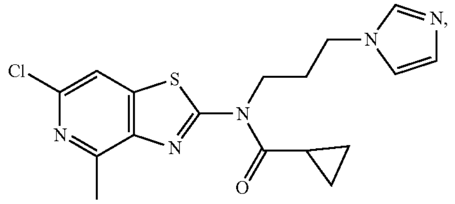
,
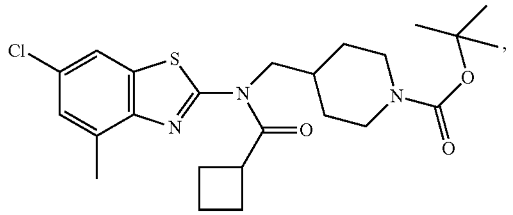
,
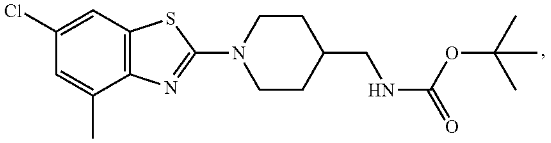
,
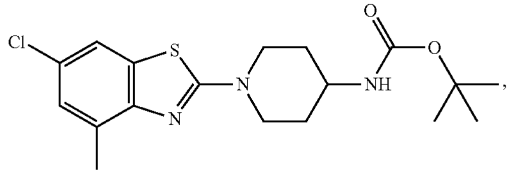
,
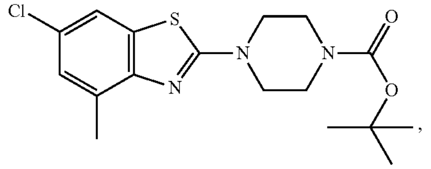
,
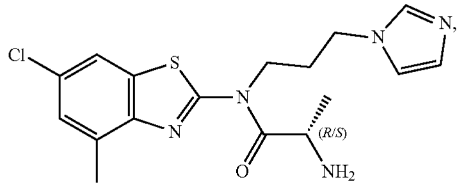
,
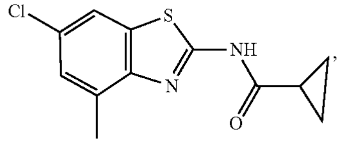
,
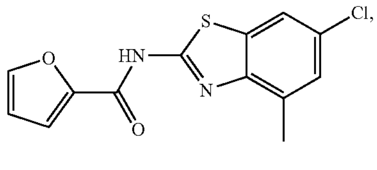
,
-continued
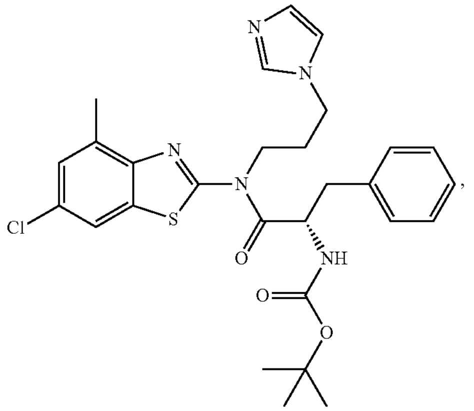
,
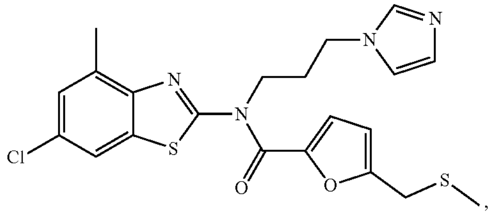
,
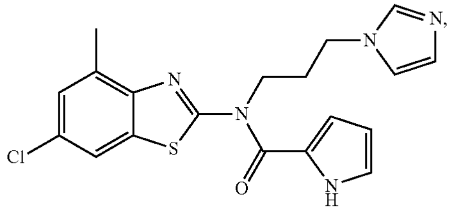
,
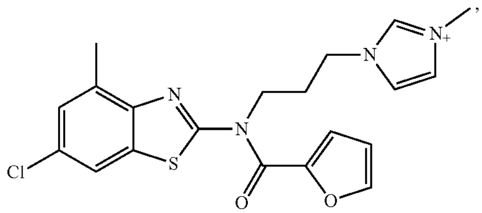
,
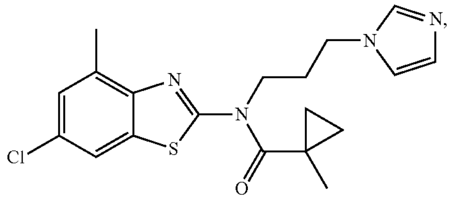
,
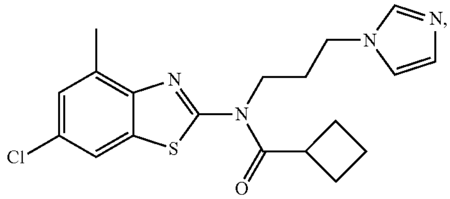
,
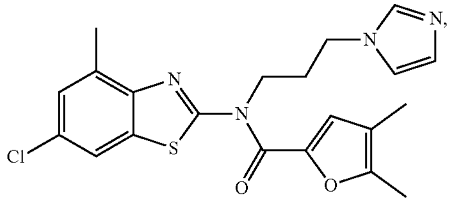
, -continued
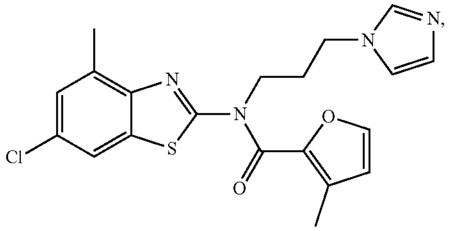
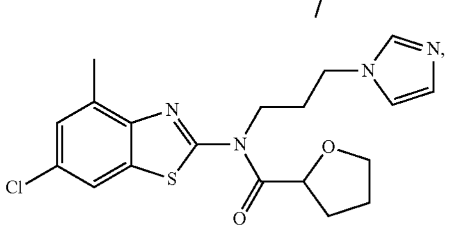
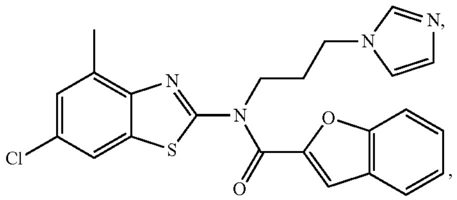
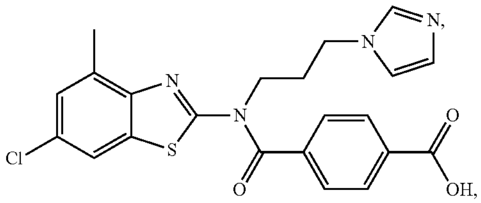
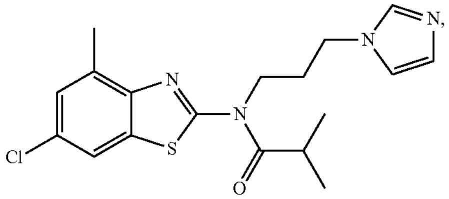
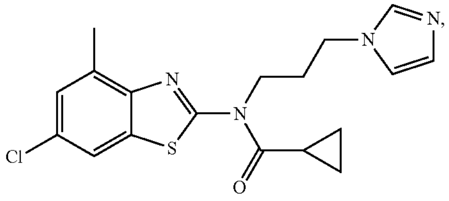
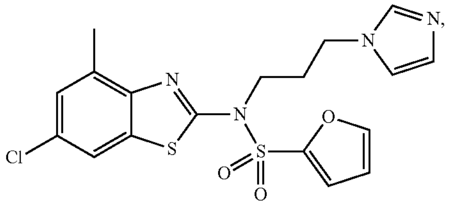
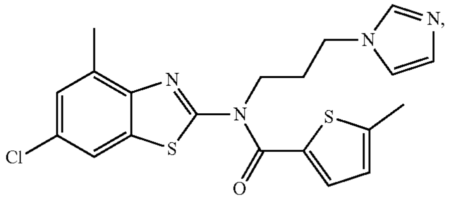
-continued
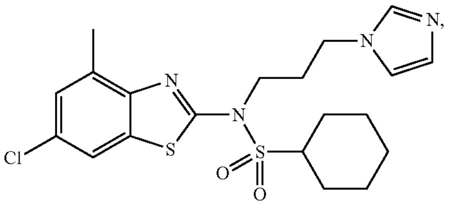
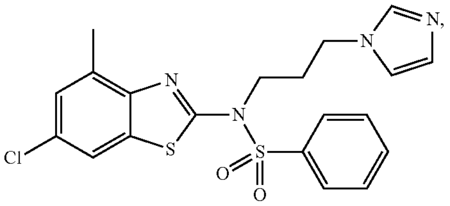
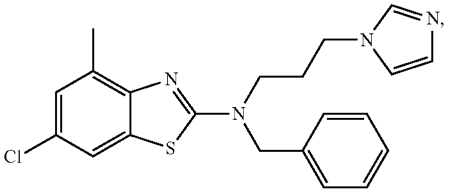
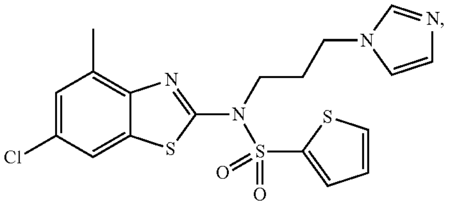
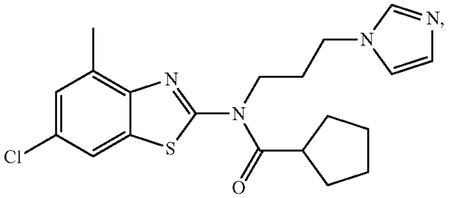
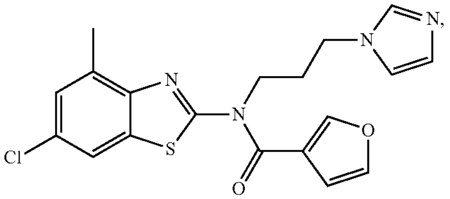
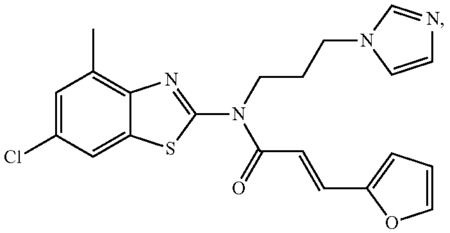
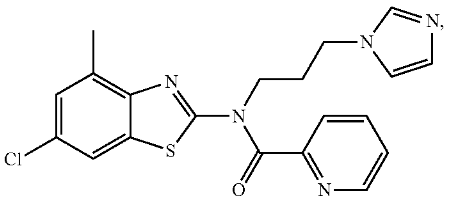

-continued

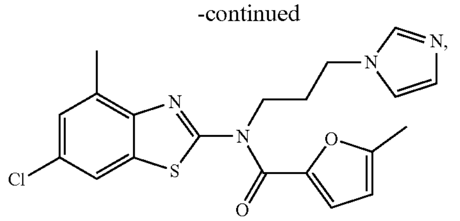

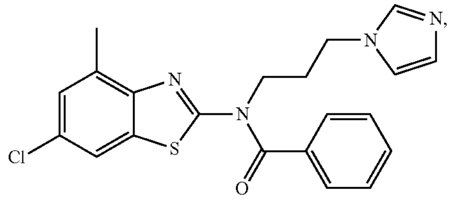

or

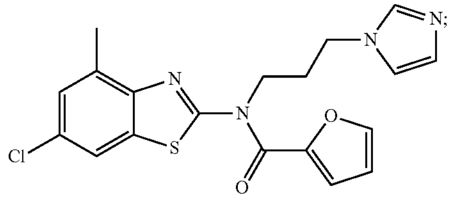

or a pharmaceutically acceptable salt thereof.

In another aspect, the present disclosure provides compound of the formula:

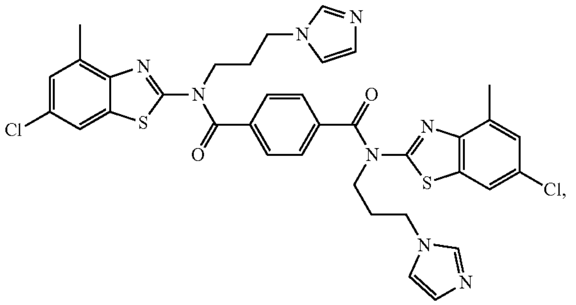

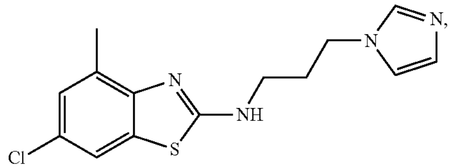

or

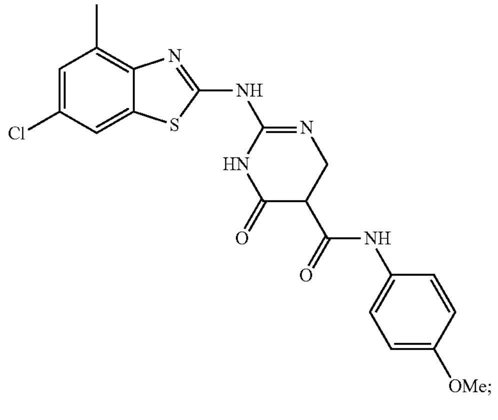

or a pharmaceutically acceptable salt thereof.

In another aspect, the present disclosure provides pharmaceutical compositions comprising:

a) a compound described herein; and b) an excipient or a pharmaceutically acceptable carrier.

In some embodiments, the composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in cremes, in lipid compositions, via a catheter, via a lavage, via continuous infusion, via infusion, via inhalation, via injection, via local delivery, or via localized perfusion.

In still yet another aspect, the present disclosure provides methods of treating or preventing a disease or disorder associated with gram-positive bacteria in a patient in need thereof comprising administering to the patient a therapeutically effective amount of N-(3-(1H-imidazol-1-yl)propyl)-N-(6-chloro-4-methylbenzo[d]thiazol-2-yl)furan-2-carboxamide or a compound or composition described herein. In some embodiments, the gram-positive bacteria is *S. aureus* such as methicillin-resistant *S. aureus* (MRSA). In some embodiments, the patient is a mammal such as a human. In some embodiments, the methods comprise intravenous, intra-arterial, intra-tumoral, subcutaneous, topical or intraperitoneal administration. In other embodiments, the methods comprise local, regional, systemic, or continual administration.

In yet another aspect, the present disclosure provides methods of inhibiting gram-positive bacteria comprising contacting the bacteria with an effective amount of N-(3-(1H-imidazol-1-yl)propyl)-N-(6-chloro-4-methylbenzo[d]thiazol-2-yl)furan-2-carboxamide or a compound or composition described herein. In some embodiments, the gram-positive bacteria is *S. aureus* such as methicillin-resistant *S. aureus* (MRSA). In some embodiments, the methods are performed in vitro. In other embodiments, the methods are performed ex vivo. In other embodiments, the methods are performed in vivo.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

DESCRIPTION OF ILLUSTRATIVE EMBODIMENTS

The compounds described herein are aminobenzothiazole compounds that show promise in the treatment of one or more antibiotic resistant bacterial infections. In particular, the compounds described herein comprise an aminobenzothiazole core with one or two substitutions on the amino group. Some of the compounds are disubstituted aminobenzothiazole compounds. Furthermore, these compounds are shown to be useful in the treatment of methicillin resistant

*Staphylococcus aureus* (MRSA). These and more details of the compounds will be described in more detail below.

I. Aminobenzothiazole Compounds

The aminobenzothaizole compounds described herein are shown, for example, above, in the summary of the invention section, and in the claims below. They may be made using the synthetic methods outlined in the Examples section. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the aminobenzothaizole compounds described herein may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the aminobenzothaizole compounds described herein are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the aminobenzothaizole compounds described herein have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

The aminobenzothaizole compounds described herein may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the aminobenzothaizole compounds described herein can have the S or the R configuration. In some embodiments, the present compounds may contain two or more atoms which have a defined stereochemical orientation.

Chemical formulas used to represent the aminobenzothaizole compounds described herein will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the aminobenzothaizole compounds described herein are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, the aminobenzothaizole compounds described herein function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the disclosure contemplates that the aminobenzothaizole compounds described herein may function as prodrugs as well as methods of delivering prodrugs. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, the aminobenzothaizole compounds described herein exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. Bacterial Infections

In some aspects, the present disclosure provides the aminobenzothaizole compounds described herein that may be used to treat a bacterial infection. While humans contain numerous different bacteria on and inside their bodies, an imbalance in bacterial levels or the introduction of pathogenic bacteria can cause a symptomatic bacterial infection. Pathogenic bacteria cause a variety of different diseases including but not limited to numerous foodborne illness, typhoid fever, tuberculosis, pneumonia, syphilis, and leprosy.

Additionally, different bacteria have a wide range of interactions with body and those interactions can modulate ability of the bacteria to cause an infection. For example, bacteria can be conditionally pathogenic such that they only cause an infection under specific conditions. For example, *Staphylococcus* and *Streptococcus* bacteria exist in the normal human bacterial biome, but these bacteria when they are allowed to colonize other parts of the body causing a skin infection, pneumonia, or sepsis. Other bacteria are known as opportunistic pathogens and only cause diseases in a patient with a weakened immune system or another disease or disorder.

Bacteria can also be intracellular pathogens which can grow and reproduce within the cells of the host organism. Such bacteria can be divided into two major categories as either obligate intracellular parasites or facultative intracellular parasites. Obligate intracellular parasites require the host cell in order to reproduce and include such bacteria as but are not limited to *Chlamydophila, Rickettsia*, and *Ehrlichia* which are known to cause pneumonia, urinary tract infections, typhus, and Rocky Mountain spotted fever. Facultative intracellular parasites can reproduce either intracellular or extracellular. Some non-limiting examples of facultative intracellular parasites include *Salmonella, Listeria, Legionella, Mycobacterium*, and *Brucella* which are known to cause food poisoning, typhoid fever, sepsis, meningitis, Legionnaire's disease, tuberculosis, leprosy, and brucellosis.

The aminobenzothaizole compounds described herein may be used in the treatment of bacterial infections, including those caused by *Staphylococcus aureus. S. aureus* is a major human pathogen, causing a wide variety of illnesses ranging from mild skin and soft tissue infections and food poisoning to life-threatening illnesses such as deep post-surgical infections, septicaemia, endocarditis, necrotizing pneumonia, and toxic shock syndrome. These organisms have a remarkable ability to accumulate additional antibiotic resistance determinants, resulting in the formation of multiply-drug-resistant strains.

Methicillin, being the first semi-synthetic penicillin to be developed, was introduced in 1959 to overcome the problem of penicillin-resistant *S. aureus* due to β-lactamase (penicillinase) production (Livermore, 2000). However, methicillin-resistant *S. aureus* (MRSA) strains were identified soon after the introduction of methicillin (Barber, 1961; Jevons, 1961). The methods described herein may be used in the treatment of MRSA bacterial strains.

Additionally, the aminobenzothaizole compounds described herein may be used to treat a *Streptococcus pneumoniae* infection. *Streptococcus pneumoniae* is a gram-positive, alpha-hemolytic, bile soluble aerotolerant anaerobe and a member of the genus *Streptococcus*. A significant human pathogenic bacterium, *S. pneumoniae* was recognized as a major cause of pneumonia in the late 19th century and is the subject of many humoral immunity studies.

Despite the name, the organism causes many types of pneumococcal infection other than pneumonia, including acute sinusitis, otitis media, meningitis, bacteremia, sepsis, osteomyelitis, septic arthritis, endocarditis, peritonitis, pericarditis, cellulitis, and brain abscess. *S. pneumoniae* is the most common cause of bacterial meningitis in adults and children and is one of the top two isolates found in ear infection, otitis media. Pneumococcal pneumonia is more common in the very young and the very old.

*S. pneumoniae* can be differentiated from *S. viridans*, some of which are also alpha hemolytic, using an optochin test, as *S. pneumoniae* is optochin sensitive. *S. pneumoniae* can also be distinguished based on its sensitivity to lysis by bile. The encapsulated, gram-positive coccoid bacteria have a distinctive morphology on gram stain, the so-called, "lancet shape." It has a polysaccharide capsule that acts as a virulence factor for the organism; more than 90 different serotypes are known, and these types differ in virulence, prevalence, and extent of drug resistance.

*S. pneumoniae* is part of the normal upper respiratory tract flora but as with many natural flora, it can become pathogenic under the right conditions (e.g., if the immune system of the host is suppressed). Invasins such as Pneumolysin, an anti-phagocytic capsule, various adhesins and immunogenic cell wall components are all major virulence factors.

Finally, bacterial infections could be targeted to a specific location in or on the body. For example, bacteria could be harmless if only exposed to the specific organs, but when it comes in contact with a specific organ or tissue, the bacteria can begin replicating and cause a bacterial infection.

A. Gram-Positive Bacteria

In some aspects of the present disclosure, the aminobenzothaizole compounds described herein may be used to treat a bacterial infection by a gram-positive bacteria. Gram-positive bacteria contain a thick peptidoglycan layer within the cell wall which prevents the bacteria from releasing the stain when dyed with crystal violet. Without being bound by theory, the gram-positive bacteria are often more susceptible to antibiotics. Generally, gram-positive bacteria, in addition to the thick peptidoglycan layer, also comprise a lipid monolayer and contain teichoic acids which react with lipids to form lipoteichoic acids that can act as a chelating agent. Additionally, in gram-positive bacteria, the peptidoglycan layer is outer surface of the bacteria. Many gram-positive bacteria have been known to cause disease including, but are not limited to, *Streptococcus, Straphylococcus, Corynebacterium, Enterococcus, Listeria, Bacillus, Clostridium*, Rathybacter, *Leifsonia*, and *Clavibacter.*

B. Gram-Negative Bacteria

In some aspects of the present disclosure, the aminobenzothaizole compounds described herein may be used to treat a bacterial infection by a gram-negative bacteria. Gram-negative bacteria do not retain the crystal violet stain after washing with alcohol. Gram-negative bacteria, on the other hand, have a thin peptidoglycan layer with an outer membrane of lipopolysaccharides and phospholipids as well as a space between the peptidoglycan and the outer cell membrane called the periplasmic space. Gram-negative bacterial generally do not have teichoic acids or lipoteichoic acids in their outer coating. Generally, gram-negative bacteria also release some endotoxin and contain prions which act as molecular transport units for specific compounds. Most bacteria are gram-negative. Some non-limiting examples of gram-negative bacteria include *Bordetella, Borrelia*, Burcelia, Campylobacteria, *Escherichia, Francisella, Haemophilus, Helicobacter, Legionella, Leptospira, Neisseria, Pseudomonas, Rickettsia, Salmonella, Shigella, Treponema, Vibrio*, and *Yersinia.*

C. Gram-Indeterminate Bacteria

In some aspects of the present disclosure, the aminobenzothaizole compounds herein may be used to treat a bacterial infection by a gram-indeterminate bacteria. Gram-indeterminate bacteria do not full stain or partially stain when exposed to crystal violet. Without being bound by theory, a gram-indeterminate bacteria may exhibit some of the properties of the gram-positive and gram-negative bacteria. A non-limiting example of a gram-indeterminate bacteria include *Mycobacterium tuberculosis* or *Mycobacterium leprae.*

III. Pharmaceutical Formulations and Routes of Administration

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of an aminobenzothaizole compounds described herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assimilable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form (also known as a unit dose) for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the disclosure are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.,* 22(3):659-661, 2008, which is incorporated herein by reference):

$$\text{HED (mg/kg)}=\text{Animal dose (mg/kg)}\times(\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 $m^2$) is 37, whereas a 20 kg child (BSA 0.8 $m^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of the aminobenzothaizole compounds or compositions described herein comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the disclosure provides that the agent(s) may be taken orally and that the timing of which is or is not dependent upon food intake. Thus, for example, the agent can be taken every morning and/or every evening, regardless of when the patient has eaten or will eat.

IV. Combination Therapy

In addition to being used as a monotherapy, the compounds of the present disclosure may also be used in combination therapies with an additional antimicrobial agent such as an antibiotic or a compound which mitigates one or more of the side effects experienced by the patient.

These therapies would be provided in a combined amount effective to achieve a reduction in one or more disease parameter(s). This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the aminobenzothaizole compounds described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 12 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations. Other potential combinations will be apparent to the skilled practitioner.

It also is conceivable that more than one administration of either the compound or the other therapy will be desired. Various combinations may be employed, where a compound of the present disclosure is "A," and the other therapy is "B," as exemplified below:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Agents or factors suitable for use in a combined therapy with agents according to the present disclosure against an infectious disease include antibiotics such as penicillins, cephalosporins, carbapenems, macrolides, aminoglycosides, quinolones (including fluoroquinolones), sulfonamides and tetracyclines. Other combinations are contemplated.

1. Antibiotics

The term "antibiotics" are drugs that may be used to treat a bacterial infection through either inhibiting the growth of bacteria or killing bacteria. Without being bound by theory, it is believed that antibiotics can be classified into two major classes: bactericidal agents that kill bacteria or bacteriostatic agents that slow down or prevent the growth of bacteria.

The first commerically available antibiotic was released in the 1930's. Since then, many different antibiotics have been developed and widely prescribed. In 2010, on average, 4 in 5 Americans are prescribed antibiotics annually. Given the prevalence of antibiotics, bacteria have started to develop resistance to specific antibiotics and antibiotic mechanisms. Without being bound by theory, the use of antibiotics in combination with another antibiotic may modulate resistance and enhance the efficacy of one or both agents.

In some embodiments, antibiotics can fall into a wide range of classes. In some embodiments, the compounds of the present disclosure may be used in conjunction with another antibiotic. In some embodiments, the compounds may be used in conjunction with a narrow spectrum antibiotic which targets a specific bacteria type. In some non-limiting examples of bactericidal antibiotics include penicillin, cephalosporin, polymyxin, rifamycin, lipiarmycin, quinolones, and sulfonamides. In some non-limiting examples of bacteriostatic antibiotics include macrolides, lincosamides, or tetracyclines. In some embodiments, the antibiotic is an aminoglycoside such as kanamycin and streptomycin, an ansamycin such as rifaximin and geldanamycin, a carbacephem such as loracarbef, a carbapenem such as ertapenem, imipenem, a cephalosporin such as cephalexin, cefixime, cefepime, and ceftobiprole, a glycopeptide such as vancomycin or teicoplanin, a lincosamide such as lincomycin and clindamycin, a lipopeptide such as daptomycin, a macrolide such as clarithromycin, spiramycin, azithromycin, and telithromycin, a monobactam such as aztreonam, a nitrofuran such as furazolidone and nitrofurantoin, an oxazolidonones such as linezolid, a penicillin such as amoxicillin, azlocillin, flucloxacillin, and penicillin G, an antibiotic polypeptide such as bacitracin, polymyxin B, and colistin, a quinolone such as ciprofloxacin, levofloxacin, and gatifloxacin, a sulfonamide such as silver sulfadiazine, mefenide, sulfadimethoxine, or sulfasalazine, or a tetracycline such as demeclocycline, doxycycline, minocycline, oxytetracycline, or tetracycline. In some embodiments, the compounds could be combined with a drug that acts against mycobacteria such as cycloserine, capreomycin, ethionamide, rifampicin, rifabutin, rifapentine, and streptomycin. Other antibiotics that are contemplated for combination therapies may include arsphenamine, chloramphenicol, fosfomycin, fusidic acid, metronidazole, mupirocin, platensimycin, quinupristin, dalfopristin, thiamphenicol, tigecycline, tinidazole, or trimethoprim.

V. Definitions

The definitions below supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

A. Chemical Groups

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; imino means =NH; "cyano" means —CN; "isocyanyl" means —N=C=O; "azido" means —$N_3$; "boronic acid" means —B$(OH)_2$; in a monovalent context "phosphate" means —OP(O)$(OH)_2$ or a deprotonated form thereof; in a divalent context "phosphate" means —OP(O)(OH)O— or a deprotonated form thereof, "mercapto" means —SH; and "thio" means =S; "thiocarbonyl" means —C(=S)—; "sulfonyl" means —S$(O)_2$—; "sulfonate" means —OS$(O)_2$—; and "sulfinyl" means —S(O)—.

In the context of chemical formulas, the symbol "—" means a single bond, "=" means a double bond, and "≡" means triple bond. The symbol "----" represents optional bond, which if present is either single or double. The symbol "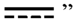" represents a single bond or a double bond. Thus, the formula

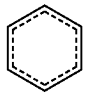

covers, for example,

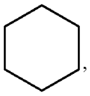, 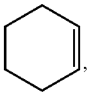, 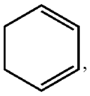, 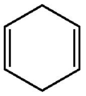 and 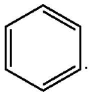.

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "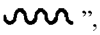", when drawn perpendicularly across a bond (e.g.,

for methyl) indicates a point of attachment the group. It is noted that the point of attachment is typically only identified in this manner for larger groups in order to assist the reader in unambiguously identifying a point of attachment. The symbol "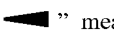" means a single bond where the group attached to the thick end of the wedge is "out of the page." The symbol "" means a single bond where the group attached to the thick end of the wedge is "into the page". The symbol "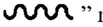" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

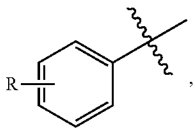

, then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

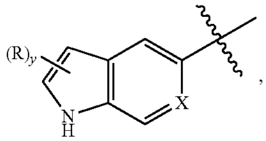

, then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed.

In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" or "C=n" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C\le 8)}$", "alkanediyl$_{(C\le 8)}$", "heteroaryl$_{(C\le 8)}$", and "acyl$_{(C\le 8)}$" is one, the minimum number of carbon atoms in the groups "alkenyl$_{(C\le 8)}$", "alkynyl$_{(C\le 8)}$", and "heterocycloalkyl$_{(C\le 8)}$" is two, the minimum number of carbon atoms in the group "cycloalkyl$_{(C\le 8)}$" is three, and the minimum number of carbon atoms in the groups "aryl$_{(C\le 8)}$" and "arenediyl$_{(C\le 8)}$" is six. "Cn-n'" defines both the minimum (n) and maximum number (n') of carbon atoms in the group. Thus, "alkyl$_{(C2\text{-}10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "$C_{1\text{-}4}$-alkyl", "C1-4-alkyl", "alkyl$_{(C1\text{-}4)}$", and "alkyl$_{(C\le 4)}$" are all synonymous. Except as noted below, every carbon atom is counted to determine whether the group or compound falls with the specified number of carbon atoms. For example, the group dihexylamino is an example of a dialkylamino$_{(C\le 12)}$ group; however, it is not an example of a dialkylamino$_{(C6)}$ group. Likewise, phenylethyl is an example of an aralkyl$_{(C=8)}$ group. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1\text{-}6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system. An aromatic compound or chemical group may be depicted as a single resonance structure; however, depiction of one resonance structure is taken to also refer to any other resonance structure. For example:

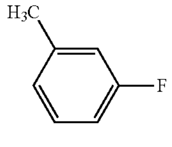

is also taken to refer to

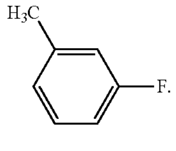

Aromatic compounds may also be depicted using a circle to represent the delocalized nature of the electrons in the fully conjugated cyclic π system, two non-limiting examples of which are shown below:

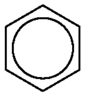 and 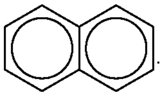.

The term "alkyl" refers to a monovalent saturated aliphatic group with a carbon atom as the point of attachment, a linear or branched acyclic structure, and no atoms other than carbon and hydrogen. The groups $-CH_3$ (Me), $-CH_2CH_3$ (Et), $-CH_2CH_2CH_3$ (n-Pr or propyl), $-CH(CH_3)_2$ (i-Pr, $^i$Pr or isopropyl), $-CH_2CH_2CH_2CH_3$ (n-Bu), $-CH(CH_3)CH_2CH_3$ (sec-butyl), $-CH_2CH(CH_3)_2$ (isobutyl), $-C(CH_3)_3$ (tert-butyl, t-butyl, t-Bu or $^t$Bu), and $-CH_2C(CH_3)_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups $-CH_2-$ (methylene), $-CH_2CH_2-$, $-CH_2C(CH_3)_2CH_2-$, and $-CH_2CH_2CH_2-$ are non-limiting examples of alkanediyl groups. The term "alkylidene" refers to the divalent group $=CRR'$ in which R and R' are independently hydrogen or alkyl. Non-limiting examples of alkylidene groups include: $=CH_2$, $=CH(CH_2CH_3)$, and $=C(CH_3)_2$. An "alkane" refers to the class of compounds having the formula H—R, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: $-CH(CH_2)_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

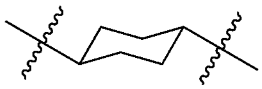 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: $-CH=CH_2$ (vinyl), $-CH=CHCH_3$, $-CH=CHCH_2CH_3$, $-CH_2CH=CH_2$ (allyl), $-CH_2CH=CHCH_3$, and $-CH=CHCH=CH_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups $-CH=CH-$, $-CH=C(CH_3)CH_2-$, $-CH=CHCH_2-$, and $-CH_2CH=CHCH_2-$ are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups $-C\equiv CH$, $-C\equiv CCH_3$, and $-CH_2C\equiv CCH_3$ are non-limiting examples of alkynyl groups. An "alkyne" refers to the class of compounds having the formula H—R, wherein R is alkynyl.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl groups (carbon number limitation permitting) attached to the first aromatic ring or any additional aromatic ring present. Non-limiting examples of aryl groups include phenyl (Ph), methylphenyl, (dimethyl)phenyl, $-C_6H_4CH_2CH_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

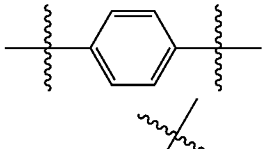, 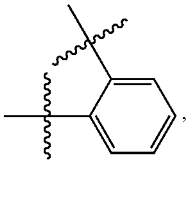,

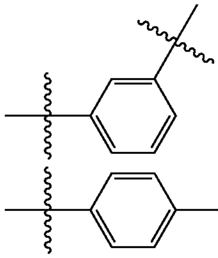,

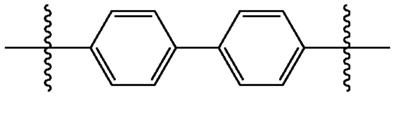, and

-continued

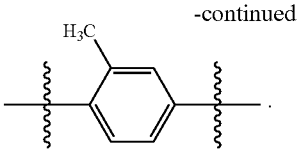

An "arene" refers to the class of compounds having the formula H—R, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused; however, the term heteroaryl does not preclude the presence of one or more alkyl or aryl groups (carbon number limitation permitting) attached to one or more ring atoms. Non-limiting examples of heteroaryl groups include benzoxazolyl, benzimidazolyl, furanyl, imidazolyl (Im), indolyl, indazolyl, isoxazolyl, methylpyridinyl, oxazolyl, oxadiazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes. The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

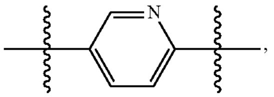

,

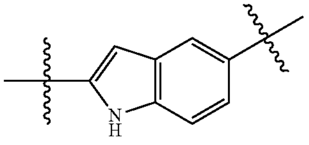

and

-continued

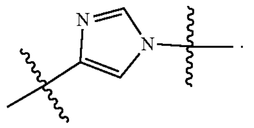

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms.

Also, the term does not preclude the presence of one or more double bonds in the ring or ring system, provided that the resulting group remains non-aromatic. Non-limiting examples of heterocycloalkanediyl groups include:

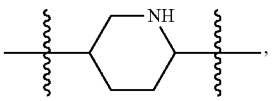

,

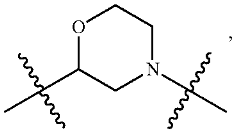

, and

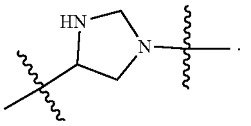

.

The term "heteroaralkyl" refers to the monovalent group -alkanediyl-heterocycloalkyl, in which the terms alkanediyl and heterocycloalkyl are each used in a manner consistent with the definitions provided above. Non-limiting examples are: 2-morpholinoethyl and piperindyl-methyl.

The term "acyl" refers to the group —C(O)R, in which R is a hydrogen, alkyl, cycloalkyl, or aryl as those terms are defined above. The groups, —CHO, —C(O)$CH_3$ (acetyl, Ac), —C(O)$CH_2CH_3$, —C(O)CH$(CH_3)_2$, —C(O)CH$(CH_2)_2$, —C(O)$C_6H_5$, and —C(O)$C_6H_4CH_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "acetal" is used to describe a carbonyl group which have reacted with two hydroxy or a dihydroxy containing compounds to form a diether of a germinal diol of the structure $R_2C(OR')_2$ arising from the carbonyl group of the structure: $R_2C(O)$, wherein neither R' is not hydrogen and each R' may be the same, different, or may be taken together to form a ring. A "mixed acetal" is an acetal wherein R' are both different. "Acetal" may be used to describe the carbonyl group, which is an aldehyde, wherein one or both R groups are hydrogen atoms, or a ketone, wherein neither R group is a hydrogen atom. "Ketal" is a subgroup of "acetal" wherein the carbonyl group is a ketone. The term "hemiacetal" is used to describe a carbonyl group which has been reacted with one hydroxy containing compound to form a monoether of a germinal diol forming a group of the structure: $R_2C(OH)OR'$, wherein R' is not hydrogen. "Hemiacetal" may be used to describe the carbonyl group that is an aldehyde, wherein one or both R groups are hydrogen atoms, or a ketone, wherein neither R group is a hydrogen atom. Analogous to "ketal", a "hemiketal" is a subgroup of "hemiacetal" wherein the carbonyl group is a ketone.

The term "alkoxy" refers to the group —OR, in which R is an alkyl, as that term is defined above. Non-limiting examples include: —$OCH_3$ (methoxy), —$OCH_2CH_3$ (ethoxy), —$OCH_2CH_2CH_3$, —OCH$(CH_3)_2$ (isopropoxy), or —OC$(CH_3)_3$ (tert-butoxy). The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —$NHCH_3$ and —$NHCH_2CH_3$. The term "dialkylamino" refers to the group —NRR', in which R and R' can be the same or different alkyl groups. Non-limiting examples of dialkylamino groups include: —N$(CH_3)_2$ and —N$(CH_3)(CH_2CH_3)$. The terms "cycloalkylamino", "alkenylamino", "alkynylamino", "arylamino", "aralkylamino", "heteroarylamino", "heterocycloalkylamino", and "alkoxyamino" when used without the "substituted" modifier, refers to groups, defined as —NHR, in which R is cycloalkyl, alkenyl, alkynyl, aryl, aralkyl, heteroaryl, heterocycloalkyl, and alkoxy, respectively. A non-limiting example of an arylamino group is —$NHC_6H_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)$CH_3$.

The terms "alkylsulfonyl" and "alkylsulfinyl" refers to the groups —S$(O)_2$R and —S(O)R, respectively, in which R is an alkyl, as that term is defined above. The terms "cycloalkylsulfonyl", "alkenylsulfonyl", "alkynylsulfonyl", "arylsulfonyl", "aralkylsulfonyl", "heteroarylsulfonyl", and "heterocycloalkylsulfonyl" are defined in an analogous manner.

The term "alkylphosphate" refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" refers to the group —OP(O)(OR)(OR'), in which R and R' can be the same or different alkyl groups, or R and R' can be taken together to represent an alkanediyl. Non-limiting examples of dialkylphosphate groups include: —OP(O)$(OMe)_2$, —OP(O)(OEt)(OMe) and —OP(O)$(OEt)_2$.

When a chemical group is used with the "substituted" modifier, one or more hydrogen atom has been replaced, independently at each instance, by —OH, —F, —Cl, —Br, —I, —$NH_2$, —$NO_2$, —$CO_2H$, —$CO_2CH_3$, —$CO_2CH_2CH_3$, —CN, —SH, —$OCH_3$, —$OCH_2CH_3$, —C(O)$CH_3$, —$NHCH_3$, —$NHCH_2CH_3$, —N$(CH_3)_2$, —C(O)$NH_2$, —C(O)$NHCH_3$, —C(O)N$(CH_3)_2$, —OC(O)$CH_3$, —NHC(O)$CH_3$, —S$(O)_2$OH, —S$(O)_2NH_2$, or an amino protecting group. For example, the following groups are non-limiting examples of substituted alkyl groups: —$CH_2OH$, —$CH_2Cl$, —$CF_3$, —$CH_2CN$, —$CH_2$C(O)OH, —$CH_2$C(O)$OCH_3$, —$CH_2$C(O)$NH_2$, —$CH_2$C(O)$CH_3$, —$CH_2OCH_3$, —$CH_2$OC(O)$CH_3$, —$CH_2NH_2$, —$CH_2$N$(CH_3)_2$, and —$CH_2CH_2Cl$. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —$CH_2Cl$ is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —$CH_2F$, —$CF_3$, and —$CH_2CF_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)$CH_2CF_3$, —$CO_2H$ (carboxyl), —$CO_2CH_3$ (methylcarboxyl), —$CO_2CH_2CH_3$, —C(O)$NH_2$ (carbamoyl), and —CON$(CH_3)_2$, are non-limiting examples of substituted acyl groups. The groups —NHC(O)$OCH_3$ and —NHC(O)$NHCH_3$ are non-limiting examples of substituted amido groups.

An "amine protecting group" or "amino protecting group" is well understood in the art. An amine protecting group is a group which modulates the reactivity of the amine group during a reaction which modifies some other portion of the molecule. Amine protecting groups can be found at least in Greene and Wuts, 1999, which is incorporated herein by reference. Some non-limiting examples of amino protecting groups include formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxycarbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethyl-silylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyl-oxycarbonyl, phenylthiocarbonyl and the like; alkylaminocarbonyl groups (which form ureas with the protect amine) such as ethylaminocarbonyl and the like; aralkyl groups such as benzyl, triphenylmethyl, benzyloxymethyl and the like; and silyl groups such as trimethylsilyl and the like. Additionally, the "amine protecting group" can be a divalent protecting group such that both hydrogen atoms on a primary amine are replaced with a single protecting group. In such a situation the amine protecting group can be phthalimide (phth) or a substituted derivative thereof wherein the term "substituted" is as defined above. In some embodiments, the halogenated phthalimide derivative may be tetrachlorophthalimide (TCphth). When used herein, a "protected amino group", is a group of the formula $PG_{MA}NH—$ or $PG_{DA}N—$ wherein $PG_{MA}$ is a monovalent amine protecting group, which may also be described as a "monovalently protected amino group" and $PG_{DA}$ is a divalent amine protecting group as described above, which may also be described as a "divalently protected amino group".

A "moiety cleavable to hydrogen" means any group that is convertible to a hydrogen atom by enzymological or chemical means including, but not limited to, hydrolysis and hydrogenolysis. Non-limiting examples include hydrolyzable groups, such as acyl groups, groups having an oxycarbonyl group, amino acid residues, peptide residues, o-nitrophenylsulfenyl, trimethylsilyl, tetrahydropyranyl, and diphenylphosphinyl. Non-limiting examples of acyl groups include formyl, acetyl, and trifluoroacetyl. Non-limiting examples of groups having an oxycarbonyl group include ethoxycarbonyl, tert-butoxycarbonyl ($—C(O)OC(CH_3)_3$), benzyloxycarbonyl, p-methoxybenzyloxycarbonyl, vinyloxycarbonyl, and 0-(p-toluenesulfonyl)ethoxycarbonyl. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and 3-Ala. Examples of suitable amino acid residues also include amino acid residues that are protected with a protecting group. Non-limiting examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), and tert-butoxycarbonyl groups ($—C(O)OC(CH_3)_3$). Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Non-limiting examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), and tert-butoxycarbonyl groups ($—C(O)OC(CH_3)_3$). Other examples of substituents "moiety cleavable to hydrogen" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl). In some embodiments, the functional group may have a structure:

B. Other Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients. Absent one of the of the above measurements, the term "about" means ±5%.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to the patient or subject, is sufficient to effect such treatment or prevention of the disease as those terms are defined below.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an active pharmaceutical ingredient of the present invention. The prodrug itself may or may not have activity with in its prodrug form. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-p-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

As used herein, the term "substantially expressed" means that the enzyme is produced by the microorganism in an amount that is 2-fold greater than that produced by a human cell line. The term "preferentially expressed" means that the enzyme is produced by the microorganism in an amount that is 10-fold greater than that produced by a human cell line. The term "exclusively expressed" means that the enzyme is produced by the microorganism in an amount that is 100-fold greater than that produced by a human cell line.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus can be considered to constitute preferred modes for its practice. However, those skilled in the art should, in light of the present disclosure, appreciate that many changes can be made in the specific embodiments which are disclosed and still obtain a like or similar result without departing from the spirit and scope of the invention.

Example 1: Compounds and Synthesis

Synthetic Procedures. Compounds of the present disclosure that can be classified as 2-aminobenzothiazoles bearing a 3-propylimdizole group attached to the amino group can be prepared according to the procedure outlined in Scheme 1. Preparation of compound 1 can be prepared in a 2-step one-pot procedure starting from 4-chloro-2-methylaniline. Addition of 2-pyridyl thiocarbonate to the aniline followed by addition of 3-aminopropyl imidazole gives the acyclic thiourea. Cyclization with benzyltrimethyl ammonium tribromide gives 2-aminobenzothiazole compound 1. Amide derivatives of type A can be prepared via a CDI, T3P, or BTFFH mediated coupling with various carboxylic acids. The sulfonamides of type B can be prepared from 1 via deprotonation of the amine followed by addition of various sulfonyl chlorides. Alkyl substituents of type C can be added via deprotonation and addition of different alkyl halides.

Scheme 1. Synthesis of basic benzothiazole analogs.

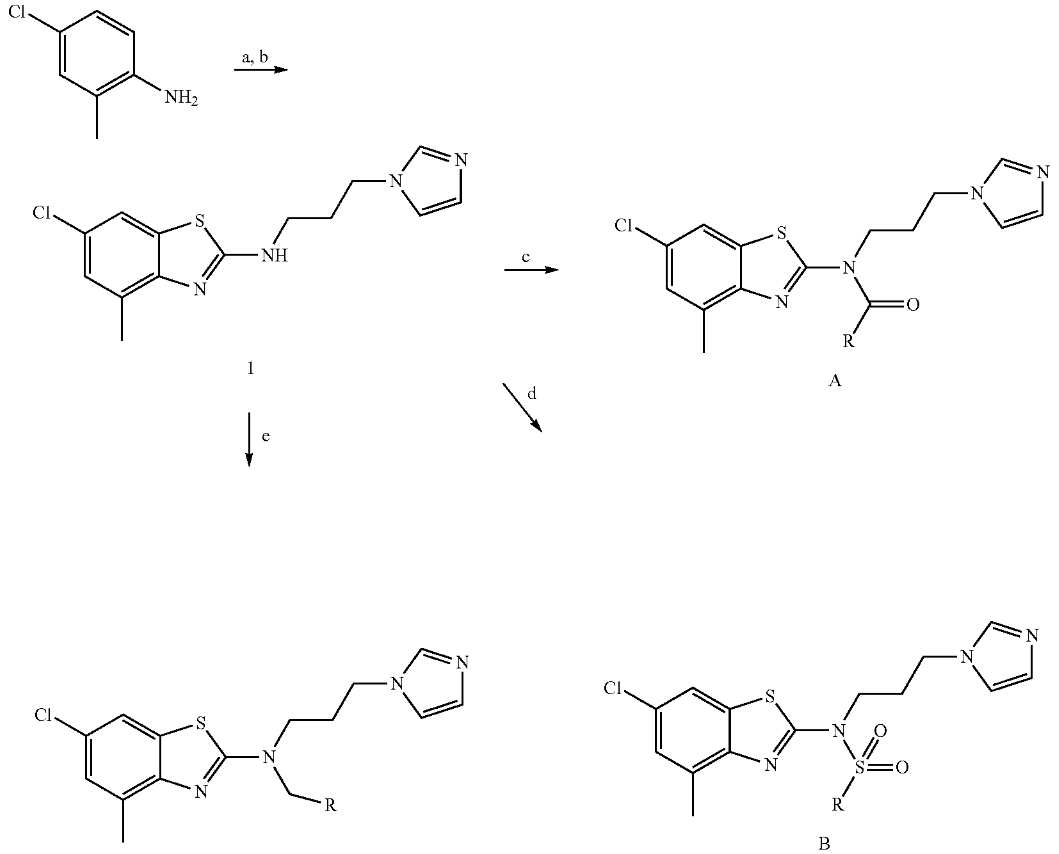

1

A

C

B

Reagents and conditions: a) Di-2-pyridyl-thiocarbonate, $CH_2Cl_2$, rt, 12 h, then add 1-(3-aminopropyl)imidazole, rt, 4 h; b) benzyltrimethyl ammonium tribromide, $CH_2Cl_2$, rt, 2 d; c) RCOOH, (2 eq.), CDI (2 eq.), $CH_2Cl_2$, 70° C., 1-3; d) R—$SO_2Cl$ (1 eq.), NaH (2 eq.), THF, 0° C. 1 h; e) $RCH_2Br$, NaH (2-3 eq.), THF, 0° C. to rt An alternate procedure for preparation of di-substituted 2-aminobenzothiazoles is outlined in Scheme 2. Starting from 2-amino-6-chloro-4-methylbenzothiazole, conversion to the 2-iodo intermediate 3 was accomplished via procedure outlined in the literature protocol (Umei et al., 2017). Compounds of type D are then prepared via displacement of the iodo group with different primary or secondary amines.

Scheme 2. Introduction of amine substituents via displacement

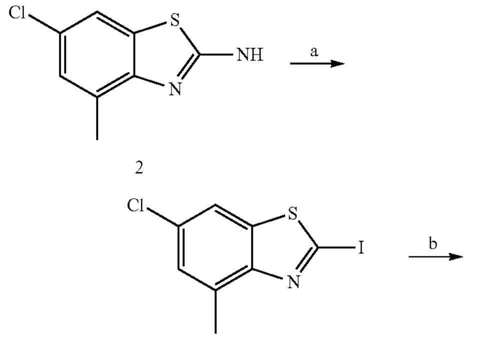

2

3

-continued

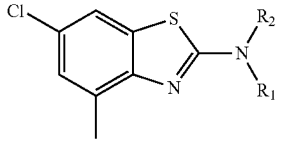

D

Reagents and conditions: a) $NaNO_2$, p-toluenesulfonic acid, KI, $CH_3CN$, $H_2O$, rt. b) $HNR_1R_2$, 1,4-dioxane, 100° C., 20 h.

Preparation of analogs with aminomethyl substitution on the 2-aminobenzothiazole ring are prepared according to the procedure outlined in Scheme 3. Starting from the Boc-protected anilines 4 or 6, conversion to the corresponding to 2-aminobenzothiazoles was accomplished via the protocol outlined above in Scheme 1. Addition of di-pyridylthiocarbonate, followed by addition of the amine and cyclization with benzyltrimethylammonium tribromide gives the 2-aminobenzothiazoles 5 and 7. Amides E and F were prepared via coupling of the desired RCOOH's using the polyphosphonic anhydride reagent T3P in pyridine. The resulting amides were deprotected under acidic conditions to yield the analogs belonging to Type E and F.

Scheme 3. Preparation of benzothiazole analogs containing 2-aminomethyl substituents.

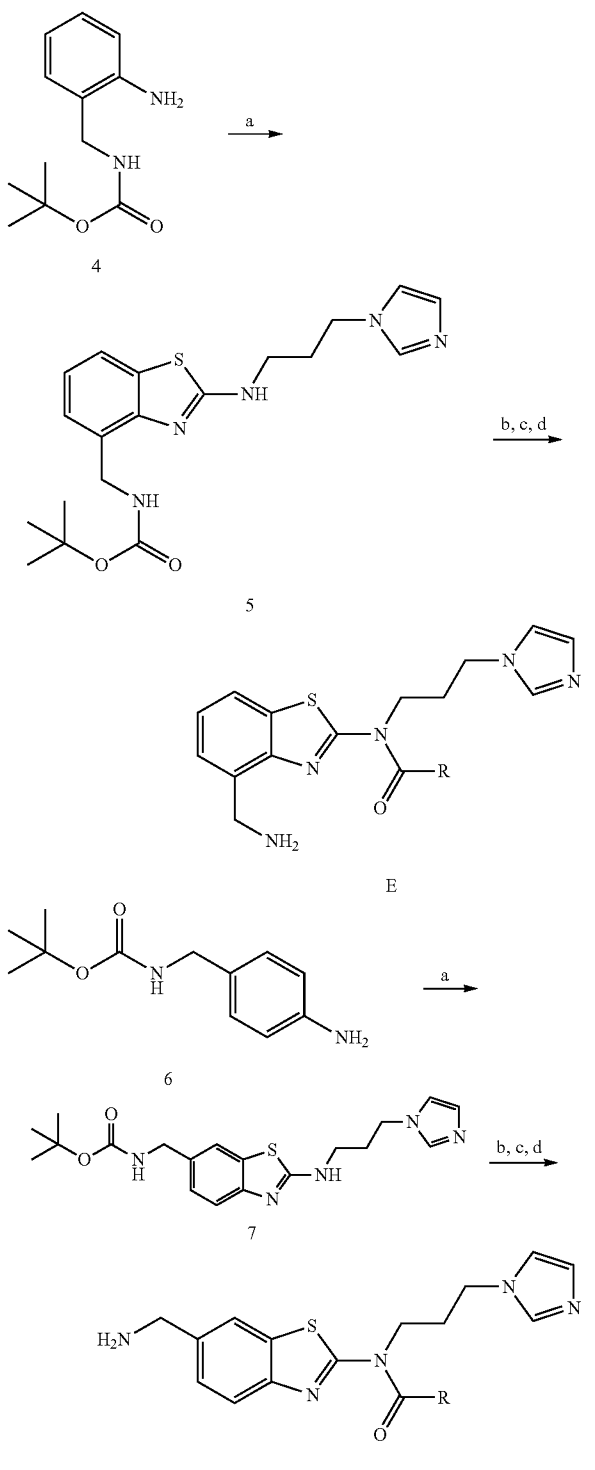

4
5
E
6
7
F

Reagents and Conditions: a) Di-2-pyridyl-thiocarbonate, $CH_2Cl_2$, rt, 12 h, then add 1-(3-aminopropyl)imidazole, rt, 4 h; b) benzyltrimethyl ammonium tribromide, $CH_2Cl_2$, rt, 2 d c) RCOOH, Pyridine, T3P, EtOAc, rt, 12 h. d) 4N—HCl-Dioxane, rt, 12 h Compounds with a nitrogen atom in the benzothiazole ring were prepared as outlined in Scheme 4. Starting from the known aminothiazole derivative 8, conversion to compound 9 was accomplished in 2 steps. Conversion of the 2-amino group to a bromide intermediate was achieved with copper bromide and tert-butyl nitrite in acetonitrile. The resulting bromide was displaced with 3-aminopropyl imidazole to give intermediate 9. Coupling of 9 with the desired carboxylic acids using BTFFH in DMF gave amides of type G. Amides of type H were prepared starting from 4-bromo-6-chloro-2-methylpyridin-3-amine following a known procedure to give the 2-aminothiazole compound which was converted to the bromide with copper bromide (Umei et al., 2017). The corresponding amides of type H were prepared from 10 using T3P in ethyl acetate.

Scheme 4. Preparation of analogs with modifications to 2-aminobenzothiazole ring.

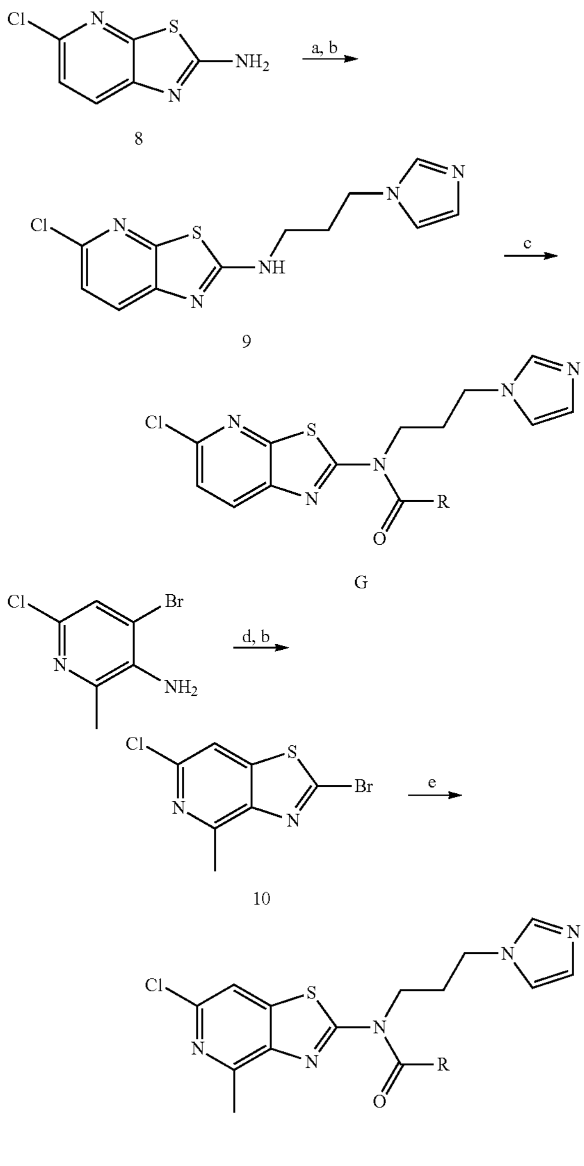

8
9
G
10
H

Reagents and Conditions: a) $CuBr_2$, $(CH_3)_3CONO$, $CH_3CN$, rt, 2 h. b) 1-(3-aminopropyl)imidazole, $K_2CO_3$, 1,4-dioxane, 100° C., 12 h. c) BTFFH, $iPr_2NEt$, DMF, $RCO_2H$, rt, 16 h d) KSCN, 1,4-dioxane, HCl (con), e) T3P, pyridine, EtOAc, $RCO_2H$ A. Experimentals Synthesis of N-(3-(1H-imidazol-1-yl)propyl)-6-chloro-4-methylbenzo[d]thiazol-2-amine (Example 1): To a solution of 4-Chloro-2-methylaniline (1.42 g, 10.03 mmol) in dichloromethane (20.0 mL) was added Di-2-pyridyl-thiocarbonate (2.33 g, 10.03 mmol) and the resulting mixture was stirred at room temperature overnight. To the mixture was added 1-(3-aminopropyl)imidazole (1.26 g, 10.03 mmol). The mixture was stirred at room temperature for 4 h. The precipitate that formed was collected by filtration. The filtrate was concentrated under reduced pressure and the solids were collected and washed with dichloromethane. The solids were combined and the crude product (0.039 g) was taken up in dichloromethane (3.0 mL) and treated with benzyltrimethyl ammonium tribromide (0.390 g, 1.00 mmol) and the resulting mixture was stirred at room temperature for 2 days. The reaction was concentrated under reduced pressure and subjected to preparative HPLC (RP18 acetonitrile/water w/0.1% TFA). The fractions containing the desired compound were partially concentrated to remove the acetonitrile. The aqueous layer was treated with 1.0 N NaOH to adjust the pH ≥7. The aqueous layer was extracted with ethyl acetate. The combined organic layers were washed with brine, dried ($Na_2SO_4$), filtered and concentrated to give the product (0.219 g, 71%) as an off-white solid. LCMS: 2.23 min, MS: ES+307.1.

Compounds Belonging to Type A:

Synthesis of N-(3-(1H-imidazol-1-yl)propyl)-N-(6-chloro-4-methylbenzo[d]thiazol-2-yl)furan-2-carboxamide (example 2): 2-furoic acid (12 mg, 0.1 mmol) and 1,1'-carbonyldiimidazole (17 mg, 0.1 mmol) were mixed in dry DCM (0.5 mL, 0.2 M) and stirred for 20 minutes at room temperature. After 20 minutes N-(3-(1H-imidazol-1-yl)propyl)-6-chloro-4 methylbenzo[d]thiazol-2-amine (15 mg, 0.05 mmol) was added under argon and stirred at 70° C. for 1 day. The reaction mixture was dissolved in minimum amount of DMSO and subjected to preparative HPLC (RP18 acetonitrile/water w/0.1% TFA). The product was isolated as a TFA salt white solid (0.011 g, 43%). $^1$H NMR (400 MHz, DMSO-$D_6$) δ 14.46 (s, 1H), 9.19 (s, 1H), 8.02 (d, J=1.0 Hz, 1H), 7.97 (s, 1H), 7.89 (t, J=1.6 Hz, 1H), 7.74 (t, J=1.6 Hz, 1H), 7.49 (d, J=3.6 Hz, 1H), 7.37 (s, 1H), 6.82 (dd, J=3.6, 1.7 Hz, 1H), 4.53 (m, 2H), 4.43 (t, J=6.7 Hz, 2H), 3.48 (brs, 2H), 2.55 (s, 3H). $^{19}$F NMR (376 MHz, DMSO-$D_6$) 6-74.35. LCMS: 2.504 min, MS: ES+400.8

Synthesis of N-(3-(1H-imidazol-1-yl)propyl)-N-(6-chloro-4-methylbenzo[d]thiazol-2-yl)benzamide (example 3): prepared from benzoic acid according to the procedure outlined for example 2. Product was isolated as a TFA salt, white solid (0.025 g, 48%). $^1$H NMR (400 MHz, MeOD) δ 8.87 (s, 1H), 7.77-7.61 (m, 1H), 7.60-7.44 (m, 7H), 7.25 (d, J=15.2 Hz, 1H), 4.30 (t, J=6.6 Hz, 4H), 2.58 (d, J=8.8 Hz, 3H), 2.49-2.35 (m, 2H). $^{19}$F NMR (376 MHz, MeOD) δ–76.90. LCMS: 2.584 min, MS: ES+410.8

Synthesis of N-(3-(1H-imidazol-1-yl)propyl)-N-(6-chloro-4-methylbenzo[d]thiazol-2-yl)-5-methylfuran-2-carboxamide (example 4): prepared from 5-methyl-2-furoic acid (26 mG, 0.2 mmol) according to the procedure outlined for example 2. Product was isolated as a TFA salt, yellow solid (0.022 g, 42%). $^1$H NMR (400 MHz, DMSO-$D_6$) δ 14.46 (s, 1H), 9.18 (s, 1H), 7.96 (d, J=1.8 Hz, 1H), 7.89 (s, 1H), 7.74 (s, 1H), 7.40 (d, J=3.5 Hz, 1H), 7.36 (s, 1H), 6.47 (d, J=3.4 Hz, 1H), 4.58-4.52 (m, 2H), 4.43 (t, J=6.7 Hz, 2H), 2.54 (s, 3H), 2.52-2.47 (m, 2H), 2.42 (s, 3H). $^{19}$F NMR (376 MHz, DMSO-$D_6$) 6-73.74. LCMS: 2.610 min, MS: ES+414.8

Synthesis of N-(3-(1H-imidazol-1-yl)propyl)-N-(6-chloro-4-methylbenzo[d]thiazol-2-yl)picolinamide (example 5): Was prepared from 2-pyridinecarboxylic acid according to the procedure outlined for example 2. Product was isolated as a TFA salt, white solid (0.030 g, 57%). $^1$H NMR (400 MHz, MeOD) δ 8.98 (s, 1H), 8.63 (d, J=4.8 Hz, 1H), 8.02 (t, J=7.8 Hz, 1H), 7.85 (d, J=7.8 Hz, 1H), 7.69 (d, J=11.6 Hz, 2H), 7.63-7.54 (m, 2H), 7.25 (s, 1H), 4.42 (t, J=6.7 Hz, 2H), 4.39-4.34 (m, 2H), 2.73-2.62 (m, 2H), 2.58 (s, 3H). $^{19}$F NMR (376 MHz, MeOD) δ −77.14. LCMS: 2.460 min, MS: ES+411.8

Synthesis of (E)-N-(3-(1H-imidazol-1-yl)propyl)-N-(6-chloro-4-methylbenzo[d]thiazol-2-yl)-3-(furan-2-yl)acrylamide (example 6): was prepared from 3-(2-furyl)acrylic acid as outlined in the procedure for example 2. Product was isolated as a TFA salt, yellow solid, (0.027 g, 50%). $^1$H NMR (400 MHz, MeOD) δ 9.01 (s, 1H), 7.77 (s, 1H), 7.69 (dd, J=11.5, 8.1 Hz, 3H), 7.63 (s, 1H), 7.23 (s, 1H), 6.99 (d, J=15.0 Hz, 1H), 6.89 (d, J=3.4 Hz, 1H), 6.62 (dd, J=3.2, 1.7 Hz, 1H), 4.66-4.55 (m, 2H), 4.50 (t, J=6.9 Hz, 2H), 2.57 (s, 3H), 2.52 (dd, J=14.4, 7.2 Hz, 2H). $^{19}$F NMR (376 MHz, MeOD) δ −77.10. LCMS: 2.688 min, MS: ES+427.1

Synthesis of N-(3-(1H-imidazol-1-yl)propyl)-N-(6-chloro-4-methylbenzo[d]thiazol-2-yl)furan-3-carboxamide (example 7): Was prepared from 3-furoic acid according to the procedure outlined for example 2. Product was isolated as a TFA salt, white solid (0.031 g, 59%). $^1$H NMR (400 MHz, MeOD) δ 8.98 (s, 1H), 8.10 (s, 1H), 7.70 (s, 1H), 7.67 (s, 1H), 7.65 (d, J=1.8 Hz, 1H), 7.59 (s, 1H), 7.22 (s, 1H), 6.88-6.66 (m, 1H), 4.51-4.45 (m, 2H), 4.42 (t, J=6.8 Hz, 2H), 2.56 (s, 3H), 2.54-2.46 (m, 2H). $^{19}$F NMR (376 MHz, MeOD) δ −77.34. LCMS: 2.493 min, MS: ES+401.1

Synthesis of N-(3-(1H-imidazol-1-yl)propyl)-N-(6-chloro-4-methylbenzo[d]thiazol-2-yl)cyclopentanecarboxamide (example 8): Was prepared from cyclopentane carboxylic according to the procedure outlined with example 2. Product was isolated as a TFA salt, colorless oil (0.019 g, 73%). $^1$H NMR (400 MHz, MeOD) δ 9.06 (s, 1H), 7.78 (s, 1H), 7.71-7.48 (m, 2H), 7.36-7.05 (m, 1H), 4.48 (dd, J=17.3, 10.4 Hz, 4H), 3.29 (m, 1H), 2.52 (dd, J=19.0, 12.1 Hz, 5H), 2.06 (dd, J=18.1, 7.1 Hz, 2H), 1.95-1.76 (m, 4H), 1.72 (dd, J=11.9, 7.3 Hz, 2H). $^{19}$F NMR (376 MHz, MeOD) δ −77.25. LCMS: m/z calcd for $C_{20}H_{24}ClN_4OS$ $[M+H]^+$ 403.13; found $[M+H]^+$ 403.1.

Synthesis of N-(3-(1H-imidazol-1-yl)propyl)-N-(6-chloro-4-methylbenzo[d]thiazol-2-yl)-5-methylthiophene-2-carboxamide (example 9): Was prepared with 5-methylthiophene-2-carboxylic acid according to the procedure outlined for example 2. Product was isolated as a TFA salt, white solid (0.016 g, 60%). $^1$H NMR (400 MHz, MeOD) δ 9.00 (s, 1H), 7.73 (s, 1H), 7.69 (s, 1H), 7.61 (s, 1H), 7.44 (d, J=3.7 Hz, 1H), 7.26 (s, 1H), 6.93-6.82 (m, 1H), 4.58 (t, J=7.3 Hz, 2H), 4.46 (t, J=6.8 Hz, 2H), 2.59 (s, 3H), 2.57-2.52 (m, 2H), 2.55 (s, 3H). $^{19}$F NMR (376 MHz, MeOD) δ −77.09. LCMS: m/z calcd for $C_{20}H_{20}ClN_4OS_2$ $[M+H]^+$ 431.07; found $[M+H]^+$ 431.1

Synthesis of N-(3-(1H-imidazol-1-yl)propyl)-N-(6-chloro-4-methylbenzo[d]thiazol-2-yl)cyclopropanecarboxamide (example 10): Was prepared from cyclopropanecarboxylic acid (9 mg, 0.1 mmol) according to the procedure outlined for example 2. Product was isolated as a TFA salt, white solid (0.009 g, 36%). $^1$H NMR (400 MHz, MeOD) δ 9.02 (s, 1H), 7.77 (s, 1H), 7.64 (d, J=14.2 Hz, 2H), 7.23 (s, 1H), 4.66 (t, J=12.5 Hz, 2H), 4.49 (t, J=7.0 Hz, 2H), 2.56 (t, J=10.0 Hz, 2H), 2.55 (s, 3H), 2.36-2.18 (m, 1H), 1.12 (ddd, J=10.8, 9.8, 7.3 Hz, 4H). $^{19}$F NMR (376 MHz, MeOD) δ −77.22. LCMS: 2.530 min, MS: ES+375.1

Synthesis of N-(3-(1H-imidazol-1-yl)propyl)-N-(6-chloro-4-methylbenzo[d]thiazol-2-yl)isobutyramide (example 11): Was prepared from isobutyric acid according to the procedure outlined for example 2. Product was isolated as a TFA salt, white solid (0.013 g, 51%). $^1$H NMR (400 MHz, MeOD) δ 9.05 (s, 1H), 7.77 (s, 1H), 7.65 (d, J=12.1 Hz, 2H), 7.21 (d, J=7.6 Hz, 1H), 4.47 (dd, J=17.0, 10.0 Hz, 4H), 3.19 (hept, J=6.6 Hz, 1H), 2.53 (s, 3H), 2.51-2.39 (m, 2H), 1.27 (d, J=6.7 Hz, 6H). $^{19}$F NMR (376 MHz, MeOD) δ −77.23. LCMS: 2.586 min, MS: ES+377.2

Synthesis of 4-((3-(1H-imidazol-1-yl)propyl)(6-chloro-4-methylbenzo[d]thiazol-2-yl)carbamoyl)benzoic acid (example 12) Was prepared from terephthalic according to the procedure outlined for example 2. Product was isolated as a TFA salt, white solid (0.024 g, 20%). $^1$H NMR (400 MHz, MeOD) δ 8.88 (s, 1H), 8.14 (d, J=8.4 Hz, 2H), 7.71 (d, J=1.7 Hz, 1H), 7.66 (d, J=8.4 Hz, 2H), 7.59 (t, J=1.6 Hz, 1H), 7.49 (t, J=1.6 Hz, 1H), 7.32-7.21 (m, 1H), 4.30 (t, J=6.7 Hz, 2H), 4.28-4.18 (m, 2H), 2.58 (s, 3H), 2.50-2.36 (m, 2H). $^{19}$F NMR (376 MHz, MeOD) δ −76.90. LCMS: 2.483 min, MS: ES+455.2

Synthesis of N-(3-(1H-imidazol-1-yl)propyl)-N-(6-chloro-4-methylbenzo[d]thiazol-2-yl)benzofuran-2-carboxamide (example 13): Was prepared from benzofuran-2-carboxylic according to the procedure outlined fro example 2. Product was isolated as a TFA salt, white solid (0.012 g, 42%). $^1$H NMR (400 MHz, MeOD) δ 9.01 (s, 1H), 7.74 (d, J=8.2 Hz, 2H), 7.71 (d, J=0.6 Hz, 1H), 7.66 (d, J=1.8 Hz, 1H), 7.61 (d, J=8.0 Hz, 1H), 7.58-7.49 (m, 2H), 7.43-7.32 (m, 1H), 7.24 (d, J=1.1 Hz, 1H), 4.80-4.66 (m, 2H), 4.55 (t, J=6.8 Hz, 2H), 2.80-2.64 (m, 2H), 2.58 (s, 3H). $^{19}$F NMR (376 MHz, MeOD) δ −76.91. LCMS: 2.856 min, MS: ES+451.2.

Synthesis of N-(3-(1H-imidazol-1-yl)propyl)-N-(6-chloro-4-methylbenzo[d]thiazol-2-yl)tetrahydrofuran-2-carboxamide (example 14): Was prepared from tetrahydro-2-furoic acid according to the procedure outlined for example 2. Product was isolated as a TFA salt, colorless oil (0.014 g, 52%). $^1$H NMR (400 MHz, MeOD) δ 9.04 (s, 1H), 7.75 (t, J=1.6 Hz, 1H), 7.71-7.57 (m, 2H), 7.20 (s, 1H), 4.96 (dd, J=7.6, 5.1 Hz, 1H), 4.50 (dt, J=13.7, 6.8 Hz, 3H), 4.41-4.24 (m, 1H), 3.94 (dq, J=22.4, 7.4 Hz, 2H), 2.69-2.45 (m, 5H), 2.43-2.31 (m, 1H), 2.30-2.16 (m, 1H), 2.11-1.96 (m, 2H). $^{19}$F NMR (376 MHz, MeOD) δ −77.04. LCMS: 2.474 min, MS: ES+405.2

Synthesis of N-(3-(1H-imidazol-1-yl)propyl)-N-(6-chloro-4-methylbenzo[d]thiazol-2-yl)-3-methylfuran-2-carboxamide (example 15): Was prepared from 3-methyl-2-furoic acid according to the procedure outlined for example 2. Product was isolated as a TFA salt, white solid (0.011 g, 41%). $^1$H NMR (400 MHz, MeOD) δ 9.03 (s, 1H), 7.76 (t, J=1.6 Hz, 1H), 7.66 (d, J=2.0 Hz, 1H), 7.62 (s, 2H), 7.22 (d, J=0.8 Hz, 1H), 6.58 (d, J=1.6 Hz, 1H), 4.64-4.40 (m, 4H), 2.72-2.60 (m, 2H), 2.57 (s, 3H), 2.37 (s, 3H). $^{19}$F NMR (376 MHz, MeOD) δ −77.12. LCMS: 2.712 min, MS: ES+415.2.

Synthesis of N-(3-(1H-imidazol-1-yl)propyl)-N-(6-chloro-4-methylbenzo[d]thiazol-2-yl)-4,5-dimethylfuran-2-carboxamide (example 16): Was prepared from 4,5-dimethyl-2-furoic acid according to the procedure outlined for example 2. Product was isolated as a TFA salt, white solid (0.014 g, 50%). $^1$H NMR (400 MHz, MeOD) δ 8.98 (s, 1H), 7.74 (s, 1H), 7.69 (d, J=1.8 Hz, 1H), 7.60 (s, 1H), 7.25 (s, 1H), 7.22 (s, 1H), 4.76-4.62 (m, 2H), 4.50 (t, J=6.8 Hz, 2H), 2.67-2.58 (m, 2H), 2.58 (s, 3H), 2.33 (s, 3H), 2.04 (s, 3H). $^{19}$F NMR (376 MHz, MeOD) δ −76.93. LCMS: 2.761 min, MS: ES+429.2

Synthesis of N-(3-(1H-imidazol-1-yl)propyl)-N-(6-chloro-4-methylbenzo[d]thiazol-2-yl)cyclobutanecarboxamide (example 17): Was prepared from cyclobutanecarboxylic according to the procedure outlined for example 2. Product was isolated as a TFA salt, white solid (0.023 g, 91%). $^1$H NMR (400 MHz, MeOD) δ 9.06 (s, 1H), 7.77 (s, 1H), 7.70-7.49 (m, 2H), 7.17 (dd, J=22.4, 5.8 Hz, 1H), 4.48 (t, J=6.9 Hz, 2H), 4.22 (s, 2H), 3.72 (dd, J=14.7, 6.7 Hz, 1H), 2.63-2.38 (m, 4H), 2.45 (s, 3H), 2.32 (d, J=8.1 Hz, 2H), 2.22-2.02 (m, 1H), 1.95 (s, 1H). $^{19}$F NMR (376 MHz, MeOD) δ −76.91. LCMS: 2.735 min, MS: ES+389.2

Synthesis of N-(3-(1H-imidazol-1-yl)propyl)-N-(6-chloro-4-methylbenzo[d]thiazol-2-yl)-1-methylcyclopropanecarboxamide (example 18): Was prepared from 1-methylcyclopropanecarboxylic acid according to the procedure outlined for example 2. Product was isolated as a TFA salt, white solid (0.010 g, 39%). $^1$H NMR (400 MHz, MeOD) δ 9.09 (s, 1H), 7.80 (s, 1H), 7.68 (d, J=4.9 Hz, 1H), 7.65 (s, 1H), 7.24 (s, 1H), 4.63-4.45 (m, 4H), 2.58 (s, 3H), 2.64-2.48 (m, 2H), 1.42 (s, 3H), 1.23-1.08 (m, 2H), 0.77 (q, J=4.8 Hz, 2H). $^{19}$F NMR (376 MHz, MeOD) δ −76.93. LCMS: 2.632 min, MS: ES+389.2.

Synthesis of N-(3-(1H-imidazol-1-yl)propyl)-N-(6-chloro-4-methylbenzo[d]thiazol-2-yl)-1H-pyrrole-2-carboxamide (example 19): Was prepared from pyrrole-2-carboxylic acid according to the procedure outlined for example 2. Product was isolated as a TFA salt, white solid (0.006 g, 12%). $^1$H NMR (400 MHz, MeOD) δ 8.96 (s, 1H), 7.73 (s, 1H), 7.65 (s, 1H), 7.59 (s, 1H), 7.22 (s, 1H), 7.13 (s, 1H), 6.76 (d, J=3.9 Hz, 1H), 6.36-6.24 (m, 1H), 4.76-4.61 (m, 2H), 4.50 (t, J=6.8 Hz, 2H), 2.65-2.51 (m, 2H), 2.57 (s, 3H). $^{19}$F NMR (376 MHz, MeOD) δ −76.90. LCMS: 2.529 min, MS: ES+400.1.

Synthesis of N-(3-(1H-imidazol-1-yl)propyl)-N-(6-chloro-4-methylbenzo[d]thiazol-2-yl)-5-((methylthio)methyl)furan-2-carboxamide (example 20): Was prepared from 5-[(methylthio)methyl]-2-furoic acid (18 mg, 0.1 mmol) according to the procedure outlined for example 2. Product was isolated as a TFA salt, yellow solid (0.023 g, 79%). $^1$H NMR (400 MHz, MeOD) δ 9.02 (s, 1H), 7.77 (s, 1H), 7.69 (d, J=1.5 Hz, 1H), 7.62 (s, 1H), 7.38 (d, J=3.5 Hz, 1H), 7.24 (s, 1H), 6.56 (d, J=3.5 Hz, 1H), 4.74-4.61 (m, 2H), 4.55 (t, J=7.0 Hz, 2H), 3.84 (s, 2H), 2.74-2.61 (m, 2H), 2.57 (s, 3H), 2.08 (s, 3H). $^{19}$F NMR (376 MHz, MeOD) δ −76.92. LCMS: 2.776 min, MS: ES+461.1.

Synthesis of (S)-tert-butyl (1-((3-(1H-imidazol-1-yl)propyl)(6-chloro-4-methylbenzo[d]thiazol-2-yl)amino)-1-oxo-3-phenylpropan-2-yl)carbamate (example 21): Was prepared from N-(tert-butoxycarbonyl)-L-phenylalanine (27 mg, 0.1 mmol) according to the procedure outlined for example 2. Product was isolated as a TFA salt, white solid (0.023 g, 67%). $^1$H NMR (400 MHz, MeOD) δ 8.94 (s, 1H), 7.68 (d, J=7.5 Hz, 2H), 7.58 (s, 1H), 7.35-7.13 (m, 7H), 4.47 (dd, J=25.6, 19.0 Hz, 1H), 4.41-4.33 (m, 2H), 4.07-3.92 (m, 1H), 3.15 (dd, J=13.3, 7.6 Hz, 1H), 3.02 (dd, J=13.3, 7.4 Hz, 1H), 2.55 (s, 3H), 2.40-2.25 (m, 2H), 1.40 (s, 9H), 1.48-1.23 (m, 1H). $^{19}$F NMR (376 MHz, MeOD) δ −76.96. LCMS: 2.976 min, MS: ES+554.2.

Compounds Belonging to Type B

Synthesis of N-(3-(1H-imidazol-1-yl)propyl)-N-(6-chloro-4-methylbenzo[d]thiazol-2-yl)thiophene-2-sulfonamide (example 22): N-(3-(1H-imidazol-1-yl)propyl)-6-chloro-4 methylbenzo[d]thiazol-2-amine (15 mg, 0.05 mmol) was dissolved in THF (0.5 mL, 0.1 M) and cooled to 0° C. then added NaH (4 mg, 0.1 mmol, 60% dispersion in mineral oil) after 10 minutes solution of 2-thiophenesulfonyl chloride (10 mg, 0.05 mmol) in THF (0.5 mL, 0.1 M) were slowly added and stirred at 0° C. for 1 hour. The crude reaction mixture was worked up with cold water, and the aqueous layer was extracted with EtOAc. The combined organic layers were dried ($Na_2SO_4$), filtered, concentrated and the reaction mixture was dissolved in minimum amount of DMSO and subjected to preparative HPLC (RP18 acetonitrile/water w/0.1% TFA) Product was isolated as a TFA salt, white solid (0.013 g, 44%). $^1$H NMR (400 MHz, MeOD) δ 8.98 (s, 1H), 7.90 (dd, J=5.0, 1.3 Hz, 1H), 7.81 (dd, J=3.9, 1.3 Hz, 1H), 7.73 (s, 1H), 7.69 (t, J=1.6 Hz, 1H), 7.58 (t, J=1.6 Hz, 1H), 7.25 (s, 1H), 7.19 (dd, J=4.9, 4.0 Hz, 1H), 4.44 (t, J=6.8 Hz, 2H), 4.21 (t, J=6.4 Hz, 2H), 2.52 (s, 3H), 2.55-2.46 (m, 2H). $^{19}$F NMR (376 MHz, MeOD) δ −77.22. LCMS: 2.617 min, MS: ES+453.0.

Synthesis of N-(3-(1H-imidazol-1-yl)propyl)-N-(6-chloro-4-methylbenzo[d]thiazol-2-yl)benzenesulfonamide (example 23): Was prepared from benzenesulfonyl chloride according to the procedure outlined for example 22. Product was isolated as a TFA salt, white solid (0.022 g, 79%). $^1$H NMR (400 MHz, MeOD) δ 8.99 (s, 1H), 7.91 (d, J=7.8 Hz, 2H), 7.77-7.62 (m, 3H), 7.61-7.52 (m, 3H), 7.20 (d, J=25.0 Hz, 1H), 4.44 (t, J=6.7 Hz, 2H), 4.19 (t, J=6.4 Hz, 2H), 2.48 (dd, J=12.5, 5.8 Hz, 2H), 2.46 (s, 3H). $^{19}$F NMR (376 MHz, MeOD) δ −76.98. LCMS: 2.676 min, MS: ES+447.1.

Synthesis of N-(3-(1H-imidazol-1-yl)propyl)-N-(6-chloro-4-methylbenzo[d]thiazol-2-yl)cyclohexanesulfonamide (example 24): Prepared from cyclohexanesulfonyl chloride as according to the procedure outlined for example 22. Product was isolated as a TFA salt, colorless oil (0.020 g, 70%). $^1$H NMR (400 MHz, MeOD) δ 8.95 (s, 1H), 7.66 (d, J=6.1 Hz, 2H), 7.56 (s, 1H), 7.24 (s, 1H), 4.39 (t, J=6.7 Hz, 2H), 4.29 (t, J=6.2 Hz, 2H), 3.51 (tt, J=11.9, 3.2 Hz, 1H), 2.57 (s, 3H), 2.46 (p, J=6.5 Hz, 2H), 2.03 (d, J=11.8 Hz, 2H), 1.83 (d, J=12.7 Hz, 2H), 1.66 (d, J=12.3 Hz, 1H), 1.55 (q, J=12.3 Hz, 2H), 1.37-1.11 (m, 3H). $^{19}$F NMR (376 MHz, MeOD) δ −77.05. LCMS: 2.799 min, MS: ES+453.1.

Synthesis of N-(3-(1H-imidazol-1-yl)propyl)-N-(6-chloro-4-methylbenzo[d]thiazol-2-yl)furan-2-sulfonamide (example 25): Was prepared from furan-2-sulfonyl chloride according to the procedure outlined for example 22. Product was isolated as a TFA salt, white solid (0.020 g, yield 73%). $^1$H NMR (400 MHz, MeOD) δ 8.99 (s, 1H), 7.81 (d, J=0.9 Hz, 1H), 7.70 (d, J=1.8 Hz, 2H), 7.59 (s, 1H), 7.36 (d, J=3.6 Hz, 1H), 7.25 (s, 1H), 6.65 (dd, J=3.6, 1.8 Hz, 1H), 4.45 (t, J=6.8 Hz, 2H), 4.30 (t, J=6.6 Hz, 2H), 2.53 (s, 3H), 2.57-2.45 (m, 2H). $^{19}$F NMR (376 MHz, MeOD) δ −77.10. LCMS: 2.579 min, MS: ES+437.0.

Examples of Type C

Synthesis of N-(3-(1H-imidazol-1-yl)propyl)-N-benzyl-6-chloro-4-methylbenzo[d]thiazol-2-amine (example 26): N-(3-(1H-imidazol-1-yl)propyl)-6-chloro-4 methylbenzo[d]thiazol-2-amine (15 mg, 0.05 mmol) was dissolved in THF (0.5 mL, 0.1 M) and cooled to 0° C. then added NaH (4 mg, 0.1 mmol, 60% dispersion in mineral oil) after 10 minutes solution of benzyl bromide (9 mg, 0.05 mmol) in THF (0.5 mL, 0.1 M) were slowly added and stirred at RT for 20 hours. The crude reaction mixture was worked up with cold water, and the aqueous layer was extracted with EtOAc. The combined organic layers were dried ($Na_2SO_4$), filtered, concentrated and the reaction mixture was dissolved in minimum amount of DMSO and subjected to preparative HPLC (RP18 acetonitrile/water w/0.1% TFA) Product was isolated as a TFA salt, colorless oil, (0.014 g, 55%). $^1$H NMR (400 MHz, MeOD) δ 8.93 (s, 1H), 7.67 (d, J=1.5 Hz, 1H), 7.57 (d, J=1.4 Hz, 1H), 7.46 (d, J=5.9 Hz, 1H), 7.39-7.25 (m, 5H), 7.10 (s, 1H), 4.75 (d, J=3.1 Hz, 2H), 4.33 (t, J=6.9 Hz, 2H), 3.71 (dd, J=9.2, 4.7 Hz, 2H), 2.48 (s, 3H), 2.32 (dd, J=12.4, 5.8 Hz, 2H). $^{19}$F NMR (376 MHz, MeOD) δ −77.26. LCMS: 2.748 min, MS: ES+397.1.

Synthesis of N-(3-(1H-imidazol-1-yl)propyl)-6-chloro-N-(cyclopropylmethyl)-4-methylbenzo[d]thiazol-2-amine (example 27): Was prepared from (bromomethyl)cyclopropane according to the procedure outlined for example 26. Product was isolated as a TFA salt, yellow solid (0.016 g, 34%). $^1$H NMR (400 MHz, MeOD) δ 8.99 (s, 1H), 7.75 (s, 1H), 7.59 (s, 1H), 7.46 (d, J=1.4 Hz, 1H), 7.08 (s, 1H), 4.38 (t, J=6.9 Hz, 2H), 3.82 (t, J=7.0 Hz, 2H), 3.40 (d, J=6.8 Hz, 2H), 2.46 (s, 3H), 2.40 (p, J=7.0 Hz, 2H), 1.22-1.09 (m, 1H), 0.67-0.56 (m, 2H), 0.42-0.32 (m, 2H). $^{19}$F NMR (376 MHz, MeOD) δ −77.04. LCMS: m/z calcd for $C_{18}H_{22}ClN_4S$ $[M+H]^+$ 361.12; found $[M+H]^+$ 361.1.

Synthesis of N,N-bis(3-(1H-imidazol-1-yl)propyl)-6-chloro-4-methylbenzo[d]thiazol-2-amine (example 28): Was prepared 1-(3-bromopropyl)-1H-imidazole according to the procedure outlined for example 26, isolated as a colorless oil, (0.025 g, 47%). $^1$H NMR (400 MHz, MeOD) δ 8.99 (s, 2H), 7.73 (t, J=1.7 Hz, 2H), 7.64-7.55 (m, 2H), 7.47 (d, J=1.9 Hz, 1H), 7.10 (d, J=1.3 Hz, 1H), 4.38 (t, J=7.1 Hz, 4H), 3.68 (t, J=7.2 Hz, 4H), 2.45 (s, 3H), 2.41-2.31 (m, 4H). $^{19}$F NMR (376 MHz, MeOD) δ −77.03. LCMS: 2.694 min, MS: ES+361.1.

Synthesis of 1-(3-(N-(6-chloro-4-methylbenzo[d]thiazol-2-yl)furan-2-carboxamido)propyl)-3-methyl-1H-imidazol-3-ium (example 29): N-(3-(1H-imidazol-1-yl)propyl)-N-(6-chloro-4-methylbenzo[d]thiazol-2-yl)furan-2-carboxamide (40 mg, 0.1 mmol, example 2) and methyl p-toluenesulfonate (186 mg, 1.0 mmol, 10 equiv.) were mixed in dry DMF (1.0 mL, 0.1 M) under argon and stirred at 70° C. for 6 days. The reaction mixture was dissolved in minimum amount of DMSO and subjected to preparative HPLC (RP18 acetonitrile/water w/0.1% TFA). Product was isolated as a TFA salt. Isolated product was dissolved in water (2 mL) and stirred with ion-exchange resin (1-$X_4$, BioRad AG, 200-400 chloride form) (0.5 g) for 4 hours. The resulting slurry was loaded onto the 1 g column of the same resin. The column was eluted with water and methanol, fractions containing the compound were combined and evaporated to dryness to get the pure chloride salt, white solid (0.015 g, 33%). $^1$H NMR (400 MHz, $D_2O$) δ 8.69 (s, 1H), 7.73 (d, J=0.8 Hz, 1H), 7.52 (s, 1H), 7.48 (s, 1H), 7.29 (d, J=1.6 Hz, 1H), 7.20 (d, J=3.6 Hz, 1H), 6.92 (s, 1H), 6.69 (dd, J=3.6, 1.6 Hz, 1H), 4.32 (t, J=6.2 Hz, 2H), 4.14-4.05 (m, 2H), 3.86 (s, 3H), 2.28 (dt, J=13.9, 7.1 Hz, 2H), 2.21 (s, 3H). LCMS: 2.680 min, MS: ES+415.1.

Compounds of Type D.

Synthesis of 6-chloro-4-methyl-2-(piperazin-1-yl)-1,3-benzothiazole (example 30). Step 1-tert-butyl 4-(6-chloro-4-methyl-1,3-benzothiazoyl)piperazine-1-carboxylate: To a solution of 6-chloro-2-iodo-4-methylbenzo[d]thiazole (3) (0.062 g, 0.200 mmol) in 1,4-dioxane (1.0 mL) was added N-Boc-piperazine (0.186 g, 1.00 mmol). The mixture was heated at 100° C. for 20 h. The resulting mixture was cooled to room temperature and then concentrated under reduced pressure. The residue was purified by silica gel chromatography (hexanes-ethyl acetate, 1:0 to 1:1) to provide the title compound (0.070 g, 95%) as a white glassy solid. $^1$H NMR (400 MHz, DMSO-$d_6$) δ ppm 7.77 (d, J=2.1 Hz, 1H), 7.21 (d, J=1.4 Hz, 1H), 3.61-3.59 (m, 4H), 3.53-3.51 (m, 4H), 2.48 (s, 3H), 1.47 (s, 9H). LCMS: 3.35 min, MS: ES+368.1

Step 2—6-chloro-4-methyl-2-(piperazin-1-yl)-1,3-benzothiazole: To a solution of tert-butyl 4-(6-chloro-4-methyl-1,3-benzothiazol-2-yl)piperazine-1-carboxylate (0.070 g, 0.190 mmol) in 1,4-dioxane (0.5 mL) was added a solution of 4N HCl in dioxane (0.467 mL, 1.90 mmol) at room temperature. A precipitate formed immediately and then methanol (0.2 mL) was added and the mixture was stirred at room temperature overnight. The 1,4-dioxane was removed and then residue was dissolved in acetonitrile/water and dried by lyophilization yielding the title compound (0.060 g, 92%) as an off-white fluffy solid. $^1$H NMR (400 MHz, DMSO-$d_6$) δ ppm 9.23 (br s, 2H), 7.82 (d, J=2.1 Hz, 1H), 7.25 (d, J=1.4 Hz, 1H), 3.84-3.82 (m, 4H), 3.30 (br m, 4H), 2.50 (s, 3H). LCMS: 2.13 min, MS: ES+268.1

Synthesis of 1-(4-(6-chloro-4-methylbenzo[d]thiazol-2-yl)piperazin-1-yl)ethan-1-one (example 31): Was prepared from according to the procedure 1-(piperazin-1-yl)ethan-1-one according to the procedure outlined in Step 1 of example 30. $^1$H NMR (400 MHz, DMSO-$d_6$) δ ppm 7.52 (s, 1H), 7.18 (s, 1H), 4.84 (d, J=4.0 Hz, 1H, 3.87-3.74 (m, 3H), 3.39-3.30 (m, 2H), (2.32 s, 3H), 1.88-1.83 (m, 2H), 1.52-1.44 (m 2H). LCMS: 2.51 min, MS: ES+310.1

Synthesis of 1-(6-chloro-4-methylbenzo[d]thiazol-2-yl) piperidin-4-ol (example 32): Was prepared from 4-hydroxypiperidine according to the procedure outlined in step 1 for example 30. $^1$H NMR (400 MHz, DMSO-$d_6$) δ ppm 7.57 (s, 1H), 7.21 (s, 1H), 3.62-3.54 (m, 8H), 2.34 (s, 3H), 2.07 (s, 3H). LCMS: 2.40 min, MS: ES+283.1 Synthesis of 1-(6-chloro-4-methyl-1,3-benzothiazol-2-yl)piperidin-4-amine (example 33) Step 1—tert-butyl N-[1-(6-chloro-4-methyl-1,3-benzothiazol-2-yl)piperidin-4-yl]carbamate Was prepared from 4-N-Boc-aminopiperidine according to step 1 of the procedure outlined for example 30. $^1$H NMR (400 MHz, DMSO-$d_6$) δ ppm 7.73 (d, J=1.8 Hz, 1H), 7.19-7.18 (m, 1H), 6.96-6.94 (br d, J=7.7 Hz, 1H) 4.02-3.99 (m, 2H), 3.61-3.58 (m, 1H), 3.30-3.23 (m, 2H), 2.47 (s, 3H), 1.90-1.87 (m, 2H), 1.52-1.45 (m, 2H), 1.43 (s, 9H). LCMS: 3.18 min, MS: ES+382.2

Step 2—1-(6-chloro-4-methyl-1,3-benzothiazol-2-yl)piperidin-4-amine: Was prepared from the compound in step 1 according to the procedure outlined for example 30. $^1$H NMR (400 MHz, DMSO-$d_6$) δ ppm 8.22 (br s, 3H), 7.76 (d, J=2.1 Hz, 1H), 7.21 (m 1H), 4.13-4.10 (br d, 2H) 3.42-3.36 (m, 1H), 3.31-3.24 (m, 2H), 2.48 (s, 3H), 2.11-2.07 (m, 2H), 1.70-1.60 (m, 2H). LCMS: 2.16 min, MS: ES+282.1

1-(6-chloro-4-methyl-1,3-benzothiazol-2-yl)piperidin-4-amine (Example 34) Step 1-tert-butyl N-{[1-(6-chloro-4-methyl-1,3-benzothiazol-2-yl)piperidin-4-yl] methyl}carbamate: Was prepared from 4-(tert-buthoxycarbonlyaminomethyl)piperidine according to the procedure outlined in step 1 for example 30. $^1$H NMR (400 MHz, DMSO-$d_6$) δ ppm 7.72 (d, J=2.1 Hz, 1H), 7.18 (d, J=1.4 Hz, 1H), 6.97-6.95 (br t, 1H) 4.07-4.03 (m, 2H), 3.18-3.12 (m, 2H), 2.91-2.88 (m, 2H), 2.47 (s, 3H), 1.9-1.75 (m, 2H), 1.73-1.67 (m, 1H), 1.42 (s, 9H), 1.26-1.16 (m, 2H). LCMS: 3.18 min, MS: ES+396.2

Step 2—1-(6-chloro-4-methyl-1,3-benzothiazol-2-yl)piperidin-4-amine: Was prepared from the compound in step 1 above according to the procedure outlined for example 30. $^1$H NMR (400 MHz, DMSO-$d_6$) δ ppm 8.08 (br s, 3H), 7.74 (d, J=1.8 Hz, 1H), 7.20 (m 1H), 4.10-4.07 (br d, 2H) 3.24-3.17 (m, 2H), 2.80-2.77 (m, 2H), 2.47 (s, 3H), 1.95-1.88 (m, 3H), 1.38-1.28 (m, 2H). LCMS: 2.18 min, MS: ES+296.1

Synthesis of 6-chloro-2-{3-[(1H-imidazol-1-yl)methyl] piperidin-1-yl}-4-methyl-1,3-benzothiazole (example 35): Was prepared from 3-(1H-imidazole-1-ylmethyl)piperidine trihydrochloride according to the procedure outlined in Step 1 for example 30. $^1$H NMR (400 MHz, DMSO-$d_6$) δ ppm 14.41 (br s, 1H), 9.19 (br s, 1H), 7.87 ((br s, 1H), 7.80 (br s, 1H), 7.74 (br s, 1H), 7.20 (br s, 1H), 4.35-4.30 (m, 1H) 4.24-4.19 (m, 2H), 3.91-3.81 (m, 2H), 3.35-3.29 (m, 1H), 3.18-3.13 (m, 1H), 2.44 (s, 3H), 2.28 (br s, 1H), 1.86-1.83 (m, 1H), 1.75-1.73 (m, 1H), 1.59-1.56 (m, 1H), 1.41-1.36 (m, 1H). LCMS: 2.34 min, MS: ES+347.1

Synthesis of 2-amino-N-(6-chloro-4-methyl-1,3-benzothiazol-2-yl)-N-[3-(1H-imidazol-1-yl)propyl]acetamide (example 36) Step 1—tert-butyl (2-((3-(1H-imidazol-1-yl) propyl)(6-chloro-4-methylbenzo[d]thiazol-2-yl)amino)-2-oxoethyl)carbamate. In a microwave vial, fitted with a stirrer was added a solution of N-Boc glycine (0.060 g, 0343 mmol) in dichloromethane (1.0 mL) followed by diisopropylethyl amine (0.212 mL, 1.19 mmol) and BTFFH (0.125 g, 0.396 mmol) and 1491 (0.081 g, 0.264 mmol). The vial was sealed and the resulting mixture was heated to 80° C. for 22 h. The mixture was stirred at room temperature overnight and then diluted with dichloromethane. The reaction mixture concentrated under reduced pressure. The residue was partitioned between ethyl acetate and water. The aqueous layer was extracted further with ethyl acetate. The combined organics were washed with brine, dried ($Na_2SO_4$), filtered and concentrated under reduced pressure. The residue was subjected to preparative HPLC (RP18 acetonitrile/water w/0.1% TFA). The fractions containing the desired compound were partially concentrated to remove the acetonitrile. The aqueous layer was treated with 1.0 N NaOH to adjust the pH ≥7. The aqueous layer was extracted with ethyl acetate. The combined organic layers were washed with brine, dried ($Na_2SO_4$), filtered and concentrated to give the product (0.025 g, 20%) as an oily residue. LCMS: 2.51 min, MS: ES+464.2.

Step 2—2-amino-N-(6-chloro-4-methyl-1,3-benzothiazol-2-yl)-N-[3-(1H-imidazol-1-yl)propyl]acetamide: Was prepared from the above compound according to the procedure outlined for example 30. $^1$H NMR (400 MHz, DMSO-$d_6$) δ ppm 9.20 (br s, 1H), 8.60 (br s, 3H), 8.03 (s, 1H), 7.89 (s, 1H), 7.73 (s, 1H), 7.42 (s, 1H), 4.45-4.37 (br m, 4H), 4.30-4.22 (br m 2H), 2.67 (s, 3H), 2.43-2.40 (br m, 2H). LCMS: 1.99 min, MS: ES+364.1

Synthesis of N-(6-chloro-4-methylbenzo[d]thiazol-2-yl)-N-(piperidin-4-ylmethyl)cyclobutanecarboxamide (example 37): Step 1—tert-butyl 4-(((6-chloro-4-methylbenzo[d]thiazol-2-yl)amino)methyl)piperidine-1-carboxylate: Was prepared from 4-(aminomethyl)-1-N-Boc-piperidine according to the procedure outlined in Step 1 for example 30. LCMS: 2.97 min, MS: ES+396.2 Step 2—tert-butyl 4-((N-(6-chloro-4-methylbenzo[d]thiazol-2-yl)cyclobutanecarboxamido)methyl)piperidine-1-carboxylate: To a solution of the above compound (0.068 g, 0.172 mmol) and cyclobutane carboxylic acid (0.052 g, 0.515 mmol) in ethyl acetate (0.4 mL) and pyridine (0.2 mL) was added T3P (0.614 mL, 50% wt in ethyl acetate, 1.03 mmol). The mixture was heated at 50° C. for 48 h. The resulting mixture was cooled to room temperature, quenched by the addition of 1.0 N NaOH. The aqueous was extracted into ethyl acetate. The organic layers were concentrated under reduced pressure. The reside was purified by silica gel chromatography (hexanes-ethyl acetate, 1:0 to 1:1) to provide the desired product (0.086 g, >100%) as an off-white solid. $^1$H NMR (400 MHz, DMSO-$d_6$) δ ppm 11.98 (s, 1H), 7.92 (d, J=1.8 Hz, 1H), 7.33-7.32 (m, 1H), 4.08 (d, J=6.9 Hz, 2H), 3.95-3.93 (br m, 2H), 3.81 (m, 1H), 3.06. (m, 1H), 2.52 (s, 3H), 2.38-2.24 (m, 4H), 2.16-2.02 (m, 4H), 1.58-1.56 (m, 2H), 1.39 (s, 9H), 1.28-1.17 (m, 2H). LCMS: 3.63 min, MS: ES+478.2

Step 3—N-(6-chloro-4-methylbenzo[d]thiazol-2-yl)-N-(piperidin-4-ylmethyl)cyclobutanecarboxamide: Was prepared from the intermediate from step 2 above following the procedure outlined for example 30. $^1$H NMR (400 MHz, DMSO-$d_6$) δ ppm 8.73 (br s, 1H), 8.46 (br s, 1H), 7.96 (m, 1H), 7.36 (m 1H), 4.18 (m, 2H), 3.85-3.77 (quint, J=8.3 Hz, 1H), 3.30-3.27 (m, 2H), 2.85-2.82 (m, 2H), 2.62 (s, 3H), 2.47-2.27 (m, 4H), 2.21-2.18 (m, 1H), 2.11-2.02 (m, 1H), 1.94-1.84 (m, 1H), 1.79-1.76 (m, 2H), 1.61-1.51 (m, 2H). LCMS: 2.55 min, MS: ES+378.1

Synthesis of N-(6-chloro-4-methyl-1,3-benzothiazol-2-yl)-N-[(1-methylpiperidin-4-yl)methyl]cyclobutanecarboxamide (example 38). To a solution of example 37 (0.035 g, 0.084 mmol) in dichloroethane (0.5 mL) was added a solution of 37% formaldehyde in water (100 mL, 7.45 mmol) followed by sodium triacetoxyborohydride (0.027 g, 0.126 mmol). The mixture was stirred at room temperature for 1 h and then diluted with dichloromethane. The reaction was quenched by the addition of a solution of saturated ammonium chloride. The reaction mixture was extracted into dichloromethane. The organic layers were washed with water, dried ($Na_2SO_4$), filtered and concentrated under reduced pressure. The residue was suspended in water and 1N NaOH was added to make the aqueous layer alkaline. The aqueous layer was extracted with ethyl acetate. The combined organic layers were washed with brine, dried ($Na_2SO_4$), filtered and concentrated under reduce pressure yielding the title compound (0.025 g, 76%) as a white waxy solid. $^1$H NMR (400 MHz, DMSO-$d_6$) δ ppm 7.97 (s, 1H), 7.36 (s, 1H), 4.13 (d, J=6.8 Hz, 2H), 3.88-3.79 (m, 1H), 2.77 (m, 2H), 2.60 (s, 3H), 2.41-2.29 (m, 4H), 2.15 (s, 3H), 2.11-2.00 (m, 1H), 1.85-1.77 (m, 4H), 1.58-1.55 (m 2H), 1.43-1.35 (m, 2H). LCMS: 2.58 min, MS: ES+392.2

Synthesis of N-(6-chloro-4-methyl-1,3-benzothiazol-2-yl)-N-[(yl)methyl]cyclopropanecarboxamide) (example 39): Step 1—tert-butyl 4-((N-(6-chloro-4-methylbenzo[d]thiazol-2-yl)cyclopropanecarboxamido)methyl)piperidine-1-carboxylate: Was prepared from cyclopropane carboxylic acid and tert-butyl 4-(((6-chloro-4-methylbenzo[d]thiazol-2-yl)amino)methyl)piperidine-1-carboxylate according to the procedure outlined in Step 2 for example 37. LCMS: 3.453 min, MS: ES+464.2.

Step 2—N-(6-chloro-4-methyl-1,3-benzothiazol-2-yl)-N-[(yl)methyl]cyclopropanecarboxamide): Was prepared from the above compound according to the procedure outlined for example 30. $^1$H NMR (400 MHz, DMSO-$d_6$) δ ppm 8.48 (br s, 1H), 7.94 (d, J=1.9 Hz, 1H), 7.36 (d, J=1.2 Hz, 1H), 4.54 (d, J=6.9 Hz, 2H), 3.31 (m, 2H), 2.88-2.82 (m, 2H), 2.64 (s, 3H), 2.46-2.40 (m, 2H), 2.30-2.26 (m, 1H), 1.85-1.82 (m, 2H), 1.64-1.54 (m, 2H), 1.12-1.10 (m, 4H). LCMS: 2.75 min, MS: ES+364.2

Synthesis of N-(6-chloro-4-methyl-1,3-benzothiazol-2-yl)-N-[(pyrrolidin-3-yl)methyl]cyclobutanecarboxamide (example 40). Step 1—tert-butyl 3-(((6-chloro-4-methylbenzo[d]thiazol-2-yl)amino)methyl)pyrrolidine-1-carboxylate: Was prepared from t-butyl-3-(aminomethyl)pyrrolidine carboxylate according to the procedure outlined in Step 1 for example 30. LCMS: 2.837 min, MS: ES+382.2

Step 2—tert-butyl 3-((N-(6-chloro-4-methylbenzo[d]thiazol-2-yl)cyclobutanecarboxamido)methyl)pyrrolidine-1-carboxylate: Was prepared from cyclobutane carboxylic acid and tert-butyl 3-(((6-chloro-4-methylbenzo[d]thiazol-2-yl)amino)methyl)pyrrolidine-1-carboxylate according to the procedure outlined in Step 2 for example 37. LCMS: 3.533 min, MS: ES+464.2.

Step 3—N-(6-chloro-4-methyl-1,3-benzothiazol-2-yl)-N-[(pyrrolidin-3-yl)methyl]cyclobutanecarboxamide: Was prepared from the above compound according to the procedure outlined for example 30. $^1$H NMR (400 MHz, DMSO-$d_6$) δ ppm 9.11 (br s, 2H), 7.97 (d, J=1.7 Hz, 1H), 7.37 (m, 1H), 4.36-4.24 (m, 2H), 3.87 (quint, J=8.3 Hz, 1H), 3.34-3.29 (m, 2H), 3.19-3.10 (m, 2H), 2.84-2.77 (m, 1H), 2.63 (s, 3H), 2.43-2.29 (m, 4H), 2.11-2.00 (m, 2H), 1.93-1.74 (m, 2H). LCMS: 2.49 min, MS: ES+364.1

Synthesis of N-(6-chloro-4-methylbenzo[d]thiazol-2-yl)-N-(pyrrolidin-3-ylmethyl)cyclopropanecarboxamide (example 41) Step 1—tert-butyl 3-((N-(6-chloro-4-methylbenzo[d]thiazol-2-yl)cyclopropanecarboxamido)methyl)pyrrolidine-1-carboxylate: Was prepared from cyclopropane carboxylic acid and tert-butyl 3-(((6-chloro-4-methylbenzo[d]thiazol-2-yl)amino)methyl)pyrrolidine-1-carboxylate according to the procedure outlined in Step 2 for example 37. LCMS: 3.568 min, MS: ES+450.2.

Step 2—N-(6-chloro-4-methylbenzo[d]thiazol-2-yl)-N-(pyrrolidin-3-ylmethyl)cyclopropanecarboxamide: Was prepared from the above compound according to the procedure outlined for example 30. $^1$H NMR (400 MHz, DMSO-$d_6$) δ ppm 9.15 (br s, 1H), 8.96 (br s, 1H), 7.95 (d, J=1.7 Hz, 1H), 7.37 (dd, J=2.1, 0.8 Hz, 1H), 4.77-4.71 (m, 1H), 4.65-4.60 (m, 1H), 3.23-3.12 (m, 2H), 2.95-2.86 (m, 1H), 2.65 (s, 3H), 2.50-2.46 (m, 1H), 2.15-2.06 (m, 1H), 1.89-1.79 (m, 1H), 1.12-1.10 (m, 4H). LCMS: 2.38 min, MS: ES+350.1

Synthesis of N-(6-chloro-4-methyl-1,3-benzothiazol-2-yl)-N-[(piperidin-3-yl)methyl]cyclopropanecarboxamide (example 42): Step 1—tert-butyl 3-(((6-chloro-4-methylbenzo[d]thiazol-2-yl)amino)methyl)piperidine-1-carboxylate: Was prepared from t-butyl-3-(aminomethyl)pyrrolidine carboxylate according to the procedure outlined in Step 1 for example 30. LCMS: 2.791 min, MS: ES+396.2

Step 2—tert-butyl 3-((N-(6-chloro-4-methylbenzo[d]thiazol-2-yl)cyclopropanecarboxamido)methyl)piperidine-1-carboxylate: Was prepared from cyclopropoane carboxylic acid and tert-butyl 3-(((6-chloro-4-methylbenzo[d]thiazol-2-yl)amino)methyl)piperidine-1-carboxylate according to the procedure outlined in Step 2 for example 37. LCMS: 3.377 min, MS: ES+464.2.

Step 3—N-(6-chloro-4-methyl-1,3-benzothiazol-2-yl)-N-[(piperidin-3-yl)methyl]cyclopropanecarboxamide: Was prepared from the compound above according to the procedure outlined for example 30. $^1$H NMR (400 MHz, DMSO-$d_6$) δ ppm 8.97-8.56 (br s, 2H), 7.95 (d, J=1.8 Hz, 1H), 7.37 (d, J=1.1 Hz, 1H), 4.56-4.46 (m, 2H), 3.77-3.69 (m, 1H), 3.56-3.48 (m, 1H), 3.29-3.22 (m, 2H), 2.92-2.80 (m, 2H), 2.65 (s, 3H), 2.47-2.41 (m, 1H), 1.87 (m, 2H), 1.71-1.61 (m, 1H), 1.49-1.41 (m, 2H), 1.11 (m, 4H). LCMS: 2.50 min, MS: ES+364.1

Synthesis of N-(6-chloro-4-methyl-1,3-benzothiazol-2-yl)-N-[2-(piperidin-4-yl)ethyl]cyclopropanecarboxamide (example 43) Step 1—tert-butyl 4-(2-((6-chloro-4-methylbenzo[d]thiazol-2-yl)amino)ethyl)piperidine-1-carboxylate. Was prepared from t-butyl-4-(aminoethyl)pyrrolidine carboxylate according to the procedure outlined in Step 1 for example 30. LCMS: 2.823 min, MS: ES+410.2

Step 2—tert-butyl 4-(2-(N-(6-chloro-4-methylbenzo[d]thiazol-2-yl)cyclopropanecarboxamido)ethyl)piperidine-1-carboxylate: Was prepared from cyclopropoane carboxylic acid and tert-butyl 4-(((6-chloro-4-methylbenzo[d]thiazol-2-yl)amino)ethyl)piperidine-1-carboxylate according to the procedure outlined in Step 2 for example 37. LCMS: 3.510 min, MS: ES+478.2.

Step 3—N-(6-chloro-4-methyl-1,3-benzothiazol-2-yl)-N-[2-(piperidin-4-yl)ethyl]cyclopropanecarboxamide: Was prepared from the compound above according to the procedure outlined for example 30. $^1$H NMR (400 MHz, DMSO-$d_6$) δ ppm 8.75 (br s, 1H), 7.93 (d, J=1.8 Hz, 1H), 7.36 (d, J=1.1 Hz, 1H), 4.54 (br t, J=7.5 Hz, 2H), 3.30 (br d, J=12.6 Hz, 2H), 2.86 (td, J=12.4, 2.0 Hz, 2H), 2.61 (s, 3H), 2.41-2.35 (m, 1H), 2.04-2.01 (br d, J=12.5 Hz, 2H), 1.85-

1.80 (m, 2H), 1.73 (br m, 1H), 1.54-1.45 (m, 2H), 1.11-1.09 (m, 4H). LCMS: 2.54 min, MS: ES+378.1

Synthesis of N-(6-chloro-4-methyl-1,3-benzothiazol-2-yl)-N-[3-(1H-pyrrol-1-yl)propyl]furan-2-carboxamide (example 44) Step 1—N-(3-(JH-pyrrol-1-yl)propyl)-6-chloro-4-methylbenzo[d]thiazol-2-amine: Was prepared from 3-(1H-pyrrol-1-yl)propane amine according to the procedure outlined in Step 1 for example 30. LCMS: 2.56 min, MS: ES+306.2

Synthesis of N-(6-chloro-4-methyl-1,3-benzothiazol-2-yl)-N-[3-(1H-pyrrol-1-yl)propyl]furan-2-carboxamide: To a solution of 2-furoic acid (0.029 g, 0.259 mmol) in dichloromethane (0.5 mL) was added diisopropylethyl amine (0.161 mL, 0.900 mmol) and BTFFH (0.095 g, 0.300 mmol). The resulting mixture was stirred at room temperature for 30 minutes and N-(3-(1H-pyrrol-1-yl)propyl)-6-chloro-4-methylbenzo[d]thiazol-2-amine (0.061 g, 0.200 mmol) was added. The mixture was stirred at room temperature overnight and then diluted with dichloromethane. The reaction mixture was washed with water and brine. The organic layers were concentrated under reduced pressure. The residue was purified by silica gel chromatography (hexanes-ethyl acetate, 1:0 to 1:1) to yield the title compound (0.047 g, 59%) as a white solid. $^1$H NMR (400 MHz, DMSO-$d_6$) δ ppm 7.98 (d, J=1.0 Hz, 1H), 7.96 (d, J=2.0 Hz, 1H), 7.35 (d, J=1.2 Hz, 1H), 7.27 (d, J=3.6 Hz, 1H), 6.84 (m, 2H), 6.75-6,74 (m, 1H), 6.03 (m, 2H), 4.46 (br t, J=Hz, 2H), 4.11 (t, J=7.7 Hz, 2H), 2.61 (s, 3H), 2.41-2.34 (m, 2H). LCMS: 3.27 min, MS: ES+400.1

Synthesis of N-(6-chloro-4-methyl-1,3-benzothiazol-2-yl)-N-{[(1r,4r)-4-aminocyclohexyl] methyl}cyclopropanecarboxamide (example 45): Step 1—N-(((1r,4r)-4-aminocyclohexyl)methyl)-6-chloro-4-methylbenzo[d]thiazol-2-amine: To a solution of tert-butyl-trans-4-formylcyclohexyl-carbamate (0.229 g, 1.01 mmol) in dichloromethane (2.0 mL) and acetic acid (0.231 mL, 4.04 mmol) was added 6-chloro-4-methylbenzo[d]thiazole-2-amine (0.200 g, 1.01 mmol). The heterogenous mixture was stirred at room temperature overnight. Sodium triacetoxyborohydride (0.642 g, 3.03 mmol) was added to the homogenous mixture, which was stirred at room temperature overnight. Crushed 4 Å M.S. were added to the reaction mixture and stirred at room temperature for an additional 24 h. The resulting mixture was filtered through a pad of Celite® washing with dichloromethane and then slowly with a saturated solution of $NaHCO_3$. The filtrate was extracted with dichloromethane. The combined organic layers were dried ($Na_2SO_4$), filtered and concentrated under reduced pressure. The residue was purified by silica gel chromatography (hexanes-ethyl acetate, 1:0 to 1:1) to provide the desired compound (0.064 g, 15%) as a white foam/solid. LCMS: 2.71 min, MS: ES+410.2.

Step 2—N-(((1r,4r)-4-aminocyclohexyl)methyl)-N-(6-chloro-4-methylbenzo[d]thiazol-2-yl)cyclopropanecarboxamide: Was prepared from the above compound and cyclopropane carboxylic acid according to the procedure outlined in Step 2 for example 37. LCMS: 2.543 min, MS: ES+378.2.

Step 3—N-(6-chloro-4-methyl-1,3-benzothiazol-2-yl)-N-{[(1r,4r)-4-aminocyclohexyl] methyl}cyclopropanecarboxamide: Was prepared from the compound above according to the procedure outlined for example 30. $^1$H NMR (400 MHz, DMSO-$d_6$) δ ppm 7.93 (d, J=2.0 Hz, 1H), 7.35 (d, J=1.2 Hz, 1H), 4.46 (d, J=6.9 Hz, 2H), 2.99 (br s, 1H), 2.62 (s, 3H), 2.42 (quint, J=6.2 Hz, 1H), 1.99 (br m, 3H), 1.82 (br m, 2H), 1.30-1.27 (br m, 4H), 1.10-1.08 (m, 4H). LCMS: 2.54 min, MS: ES+378.2

Synthesis of Compounds of Type E

Synthesis of N-[4-(aminomethyl)-1,3-benzothiazol-2-yl]-N-[3-(1H-imidazol-1-yl)propyl]furan-2-carboxamide (example 46) Step 1—tert-butyl ((2-((3-(1H-imidazol-1-yl)propyl)amino)benzo[d]thiazol-4-yl)methyl)carbamate. To a solution of 2-[(N-Boc)aminomethyl]aniline (0.445 g, 2.00 mmol) in dichloromethane (4.0 mL) was added di-2-pyridylthiocarbonate (0.465 g, 2.0 mmol) and the resulting mixture was stirred at room temperature overnight. To the mixture was added 1-(3-aminopropyl)imidazole (0.250 g, 2.00 mmol). The mixture was stirred at room temperature for 2 days and then concentrated under reduced pressure. The residue was dissolved in ethyl acetate. The organic layer was washed with water, brine, dried ($Na_2SO_4$), filtered and concentrated under reduced pressure. The crude product was taken up in dichloromethane (10.0 mL) and treated with benzyltrimethyl ammonium tribromide (0.753 g, 1.93 mmol) and the resulting mixture was stirred at room temperature overnight. The reaction was concentrated under reduced pressure and subjected to preparative HPLC (RP18 acetonitrile/water w/0.1% TFA). The fractions containing the desired compound were partially concentrated to remove the acetonitrile. The aqueous layer was treated with 1.0 N NaOH to adjust the pH ≥7. The aqueous layer was extracted with ethyl acetate. The combined organic layers were washed with brine, dried ($Na_2SO_4$), filtered and concentrated to give the product (0.469 g, 63%) brown oily residue. LCMS: 1.93 min, MS: ES+388.2.

Step 2—tert-butyl ((2-(N-(3-(1H-imidazol-1-yl)propyl) furan-2-carboxamido)benzo[d]thiazol-4-yl)methyl)carbamate Was prepared from the compound above and 2-furoic acid according to the procedure outlined in Step 2 for example 37. LCMS: 2.47 min, MS: ES+482.2.

Step 3—N-[4-(aminomethyl)-1,3-benzothiazol-2-yl]-N-[3-(1H-imidazol-1-yl)propyl]furan-2-carboxamide: Was prepared according to the procedure outlined in for example 30. $^1$H NMR (400 MHz, DMSO-$d_6$) δ ppm 14.68 (br s, 1H), 9.39 (s, 1H), 8.69 (br s, 2H), 8.11-8.09 (m, 2H), 7.99 (s, 1H), 7.86 (s, 1H), 7.65 (d, J=7.4 Hz, 1H), 7.56 (d, J=3.6 Hz, 1H), 7.48-7.45 (m, 1H), 6.88-6.87 (m, 1H), 4.63 (m, 2H), 4.56 (t, J=6.9 Hz, 2H), 4.46-4.44 (m, 2H), 2.63-2.57 (m, 2H). LCMS: 1.77 min, MS: ES+382.1

Synthesis of N-[4-(aminomethyl)-1,3-benzothiazol-2-yl]-N-[3-(1H-imidazol-1-yl)propyl]cyclobutanecarboxamide (example 47). Step 1—tert-butyl ((2-(N-(3-(1H-imidazol-1-yl)propyl)cyclobutanecarboxamido)benzo[d]thiazol-4-yl) methyl)carbamate: Was prepared from tert-butyl ((2-((3-(1H-imidazol-1-yl)propyl)amino)benzo[d]thiazol-4-yl) methyl)carbamate and cyclobutane carboxylic acid according to the procedure outlined in Step 2 for example 37. LCMS: 2.538 min, MS: ES+470.2

Step 2—N-[4-(aminomethyl)-1,3-benzothiazol-2-yl]-N-[3-(1H-imidazol-1-yl)propyl]cyclobutanecarboxamide: Was prepared from the above compound according to the procedure outlined for example 30. $^1$H NMR (400 MHz, DMSO-$d_6$) δ ppm 14.65 (br s, 1H), 9.35 (s, 1H), 8.61 (br s, 2H), 8.05 (d, J=7.9 Hz, 1H), 7.96 (s, 1H), 7.88 (s, 1H), 7.61 (d, J=7.5 Hz, 1H), 7.24 (t, J=7.5 Hz, 1H), 4.50 (m, 2H), 4.41-4.40 (m, 2H), 4.22-4.18 (m, 2H), 3.84-3.80 (m, 1H), 2.46-2.30 (m, 6H), 2.12-2.00 (m, 1H), 1.91 (m, 1H). LCMS: 1.84 min, MS: ES+370.2

Synthesis of N-[4-(aminomethyl)-1,3-benzothiazol-2-yl]-N-[3-(1H-imidazol-1-yl)propyl]cyclopropanecarboxamide (example 48). Step 1—tert-butyl ((2-(N-(3-(1H-imidazol-1-yl)propyl)cyclopropanecarboxamido)benzo[d]thiazol-4-yl) methyl)carbamate: Was prepared from tert-butyl ((2-((3-(1H-imidazol-1-yl)propyl)amino)benzo[d]thiazol-4-yl) methyl)carbamate and cyclopropane carboxylic acid according to the procedure outlined in Step 2 for example 37. LCMS: 2.338 min, MS: ES+456.2

Step 2—N-[4-(aminomethyl)-1,3-benzothiazol-2-yl]-N-[3-(1H-imidazol-1-yl)propyl]cyclopropanecarboxamide: Was prepared from the above compound according to the procedure outlined for example 30. $^1$H NMR (400 MHz, DMSO-$d_6$) δ ppm 14.65 (br s, 1H), 9.36 (s, 1H), 8.65 (br s, 3H), 8.03 (d, J=7.8 Hz, 1H), 7.97 (s 1H), 7.87 (s, 1H), 7.61 (d, J=7.4 Hz, 1H), 7.42 (t, J=7.7 Hz, 1H), 4.63-4.59 (m, 2H), 4.53-4.49 (m, 2H), 4.42-4.40 (m, 2H), 2.51-2.43 (m, 3H), 1.12 (m, 4H). LCMS: 1.74 min, MS: ES+356.2

Synthesis of Compounds of Type F

Synthesis of N-[6-(aminomethyl)-1,3-benzothiazol-2-yl]-N-[3-(1H-imidazol-1-yl)propyl]furan-2-carboxamide (example 49) Step 1—tert-butyl ((2-((3-(1H-imidazol-1-yl)propyl)amino)benzo[d]thiazol-6-yl)methyl)carbamate: To a solution of 4-[(N-Boc)aminomethyl]aniline (0.222 g, 1.00 mmol) in dichloromethane (2.0 mL) was added di-2-pyridylthiocarbonate (0.232 g, 1.0 mmol) and the resulting mixture was stirred at room temperature overnight. To the mixture was added 1-(3-aminopropyl)imidazole (0.125 g, 1.00 mmol). The mixture was stirred at room temperature for 4 h and then concentrated under reduced pressure. The crude product was taken up in dichloromethane (3.0 mL) and treated with benzyltrimethyl ammonium tribromide (0.251 g, 0.644 mmol) and the resulting mixture was stirred at room temperature overnight. The reaction was concentrated under reduced pressure and subjected to preparative HPLC (RP18 acetonitrile/water w/0.1% TFA). The fractions containing the desired compound were partially concentrated to remove the acetonitrile. The aqueous layer was treated with 1.0 N NaOH to adjust the pH ≥7. The aqueous layer was extracted with ethyl acetate. The combined organic layers were washed with brine, dried ($Na_2SO_4$), filtered and concentrated to give the product (0.098 g, 39%) as an off-white solid. LCMS: 2.06 min, MS: ES+388.2.

Step 2—tert-butyl ((2-(N-(3-(1H-imidazol-1-yl)propyl)furan-2-carboxamido)benzo[d]thiazol-6-yl)methyl)carbamate: Was prepared from tert-butyl ((2-((3-(1H-imidazol-1-yl)propyl)amino)benzo[d]thiazol-6-yl)methyl)carbamate and 2-furanoic acid according to the procedure outlined in Step 2 for example 37. LCMS: 2.30 min, MS: ES+482.2

Step 3—N-[6-(aminomethyl)-1,3-benzothiazol-2-yl]-N-[3-(1H-imidazol-1-yl)propyl]furan-2-carboxamide: Was prepared from the above compound according to the procedure outlined for example 30. $^1$H NMR (400 MHz, DMSO-$d_6$) δ ppm 14.74-14.61 (br s, 1H), 9.29 (s, 1H), 8.48 (br s, 2H), 8.15 (s, 1H), 8.05 (d, J=0.98 Hz, 1H), 7.93 (m, 1H), 7.87 (d, J=8.3 Hz, 1H), 7.80 (m, 1H), 7.65 (d, J=8.5 Hz, 1H), 7.52 (d, J=3.4 Hz, 1H), 6.85 (dd, J=3.6, 1.7 Hz, 1H), 4.55 (t, J=7.5 Hz, 2H), 4.46 (t, J=6.7 Hz, 2H), 4.19-4.16 (m, 2H). LCMS: 1.61 min, MS: ES+382.1

Synthesis of N-[6-(aminomethyl)-1,3-benzothiazol-2-yl]-N-[3-(1H-imidazol-1-yl)propyl]cyclobutanecarboxamide (example 50). Step 1—tert-butyl ((2-(N-(3-(1H-imidazol-1-yl)propyl)cyclobutanecarboxamido)benzo[d]thiazol-6-yl) methyl)carbamate: Was prepared from tert-butyl ((2-((3-(1H-imidazol-1-yl)propyl)amino)benzo[d]thiazol-6-yl) methyl)carbamate and cyclobutane carboxylic acid according to the procedure outlined in Step 2 for example 37. LCMS: 2.73 min, MS: ES+470.2.

Step 2—N-[6-(aminomethyl)-1,3-benzothiazol-2-yl]-N-[3-(1H-imidazol-1-yl)propyl]cyclobutanecarboxamide: Was prepared from the above compound according to the procedure outlined for example 30. $^1$H NMR (400 MHz, DMSO-$d_6$) δ ppm 14.84 (br s, 1H), 9.32 (s, 1H), 8.55 (br s, 2H), 8.11 (d, J=1.2 Hz, 1H), 7.92 (m, 1H), 7.82-7.79 (m, 2H), 7.64-7.62 (dd, J=8.4, 1.6 Hz, 1H), 4.42 (t, J=6.8 Hz, 2H), 4.16-4.11 (m, 4H), 3.82-3.73 (m, 1H), 2.44-2.23 (m, 6H), 2.10-1.98 (m, 1H), 1.92-1.84 (m, 1H). LCMS: 2.05 min, MS: ES+370.2

Synthesis of N-[4-(aminomethyl)-1,3-benzothiazol-2-yl]-N-[3-(1H-imidazol-1-yl)propyl]furan-2-carboxamide (example 51): Step 1—tert-butyl ((2-(N-(3-(1H-imidazol-1-yl) propyl)cyclopropanecarboxamido)benzo[d]thiazol-6-yl) methyl)carbamate. Was prepared from tert-butyl ((2-((3-(1H-imidazol-1-yl)propyl)amino)benzo[d]thiazol-6-yl) methyl)carbamate and cyclopropane carboxylic acid according to the procedure outlined in Step 2 for example 37. LCMS: 2.37 min, MS: ES+456.1

Step 2—N-[4-(aminomethyl)-1,3-benzothiazol-2-yl]-N-[3-(1H-imidazol-1-yl)propyl]furan-2-carboxamide: Was prepared from the above compound according to the procedure outlined for example 30. $^1$H NMR (400 MHz, DMSO-$d_6$) δ ppm 14.87 (br s, 1H), 9.31 (s, 1H), 8.58 (br s, 2H), 8.15 (s, 1H), 8.10 (d, J=1.2 Hz, 1H), 7.92 (t, J=1.5, 1H), 7.81-7.79 (m, 2H), 7.65-7.62 (dd, J=8.4, 1.6 Hz, 1H), 4.53 (t, J=7.4 Hz, 2H), 4.44 (t, J=6.9 Hz, 2H), 4.14 (m, 2H), 2.49-2.38 (m, 3H), 1.10 (m, 4H). LCMS: 1.60 min, MS: ES+356.2

Synthesis of Compounds of Type G

Synthesis of N-{5-chloro-[1,3]thiazolo[5,4-b]pyridin-2-yl}-N-[3-(1H-imidazol-1-yl)propyl]furan-2-carboxamide (example 52): Step 1—N-(3-(1H-imidazol-1-yl)propyl)-5-chlorothiazolo[5,4-b]pyridin-2-amine: Copper(II)bromide (0.759 g, 3.40 mmol) and tert-butyl nitrite (0.351 g, 3.40 mmol) were combined in acetonitrile (5.0 mL) and stirred at room temperature for 10 minutes. This mixture was added to a suspension of 5-chlorothiazolo[5,4]pyridine-2-amine (0.372 g, 2.00 mmol) in acetonitrile (10.0 mL). The resulting mixture was stirred at room temperature for 2 h and then concentrated under reduced pressure. The reaction mixture was taken up in ethyl acetate which was then washed with water, a solution of 1.0 N HCl, a saturated solution of $NaHCO_3$, brine, dried ($Na_2SO_4$), filtered and concentrated under reduced pressure to give the desired compound (0.441 g, 88%) as a yellow solid. LC: 2.35 min Step—2: To a solution of the above bromide (0.249 g, 1.00 mmol) in 1,4-dioxane (2.0 mL) was added 1-(3-aminopropyl)imidazole (0.376 g, 3.00 mmol) and potassium carbonate (0.622 g, 4.50 mmol). The mixture was heated at 100° C. overnight. The resulting mixture was cooled to room temperature and then concentrated under reduced pressure. Water was added to the residue and the solids were collected by filtration washing with water and then hexanes to provide the title compound (0.295 g, >100%) as a tan solid. LCMS: 2.02 min, MS: ES+294.1

Step 3—N-{5-chloro-[1,3]thiazolo[5,4-b]pyridin-2-yl}-N-[3-(1H-imidazol-1-yl)propyl]furan-2-carboxamide: Was prepared from N-[4-(aminomethyl)-1,3-benzothiazol-2-yl]-N-[3-(1H-imidazol-1-yl)propyl]furan-2-carboxamide and 2-furanoic acid according to the procedure outlined in Step 2 for example 37. $^1$H NMR (400 MHz, DMSO-$d_6$) δ ppm 8.83 (br s, 1H), 8.24 (d, J=8.5 Hz, 1H), 8.04 (d, J=1.0 Hz, 1H), 7.74 (br s, 1H), 7.66 (d, J=8.5 Hz, 1H), 7.56-7.54 (m, 2H), 6.85 (m, 1H), 4.55 (m, 2H), 4.39 (t, J=6.7 Hz, 2H), 3.20 (m, 1H), 2.52-2.46 (m, 2H), 1.78 (m, 1H). LCMS: 2.13 min, MS: ES+388.1

Synthesis of N-{5-chloro-[1,3]thiazolo[5,4-b]pyridin-2-yl}-N-[3-(1H-imidazol-1-yl)propyl]cyclopropanecarboxamide (example 53): Was prepared from N-[4-(aminomethyl)-1,3-benzothiazol-2-yl]-N-[3-(1H-imidazol-1-yl)propyl]furan-2-carboxamide and cyclopropane carboxylic acid according to the procedure outlined in Step 2 for example 37. $^1$H NMR (400 MHz, DMSO-$d_6$) δ ppm 9.08 (br s, 1H), 8.15 (d, J=8.5 Hz, 1H), 7.84 (br s, 1H), 7.70 (br m, 1H), 7.62 (d, J=8.5 Hz, 1H), 4.54 (t, J=7.4 Hz, 2H), 4.39 (t, J=7.0 Hz, 2H), 2.49-2.37 (m, 3H), 1.14-1.12 (m, 4H). LCMS: 2.11 min, MS: ES+362.1

Synthesis of Compounds of Type H

Synthesis of N-{6-chloro-4-methyl-[1,3]thiazolo[4,5-c]pyridin-2-yl}-N-[3-(1H-imidazol-1-yl)propyl]furan-2-carboxamide (example 55). Step 1—N-(3-(1H-imidazol-1-yl)propyl)-6-chloro-4-methylthiazolo[4,5-c]pyridin-2-amine: To a solution of 4-bromo-6-chloro-2-methylpyridin-3-amine, prepared according to the procedure described in WO2017220431 (1.25 g, 5.64 mmol) in 1,4-dioxane (20 mL) was added potassium thiocyanate (1.65 g, 16.93 mmol) followed by concentrated HCl (0.1 mL). The resulting mixture was heated at reflux for 2 days and then allowed to cool to room temperature and concentrated under reduced pressure. Water and 1.0 N NaOH was added to the residue and the precipitate was collected by filtration and washed with ethyl acetate. The filtrate was placed in a separatory funnel and the layers where separated. The aqueous layer was further extracted with ethyl acetate. The combined organics were washed with water, a saturated solution of $Na_2S_2O_3$, brine, dried ($Na_2SO_4$), filtered and concentrated under reduced pressure. The residue was absorbed on to silica gel and purified by silica gel chromatography (hexanes-ethyl acetate, 1:0 to 0:1) to provide the desired compound as a brick colored solid. LCMS: 1.53 min, MS: ES+200.0

Step 2: Copper(II)bromide (0.373 g, 1.67 mmol) and tert-butyl nitrite (0.172 g, 1.67 mmol) were combined in acetonitrile (2.5 mL) and stirred at room temperature for 10 minutes. This mixture was added to a suspension of aminobenzothiazole from above (0.196 g, 0.892 mmol) in acetonitrile (5.0 mL). The resulting mixture was stirred at room temperature overnight. By LC/MS there was still starting material present. A mixture of copper(II)bromide (0.110 g, 0.491 mmol) and tert-butyl nitrite (0.051 g, 0.491 mmol), previously stirred at room temperature for 10 minutes, was added to the reaction mixture which was stirred at room temperature for 1.5 h. The reaction mixture was then concentrated under reduced pressure. The residue was taken up in ethyl acetate which was then washed with water, a solution of 1.0 N HCl, a saturated solution of $NaHCO_3$, brine, dried ($Na_2SO_4$), filtered and concentrated under reduced pressure. The residue was purified by silica gel chromatography (hexanes-ethyl acetate, 1:0 to 3:7) to provide the bromothiazole (0.116 g, 48%) as an orange solid. LCMS: 2.28 min, MS: ES+264.9.

Step 3: To a solution of the above bromo compound (0.116 g, 0.441 mmol) in 1,4-dioxane (1.0 mL) was added 1-(3-aminopropyl)imidazole (0.218 g, 1.74 mmol). The resulting black mixture was stirred at room temperature overnight. The reaction mixture was concentrated under reduced pressure and water was added to the residue. The solids were collected by filtration washing with water and then hexanes to provide the desired compound (0.116 g, 86%) as a pink colored solid. LCMS: 1.70 min, MS: ES+308.1.

Step—3: N-{6-chloro-4-methyl-[1,3]thiazolo[4,5-c]pyridin-2-yl}-N-[3-(1H-imidazol-1-yl)propyl]furan-2-carboxamide. To a solution of N-(3-(1H-imidazol-1-yl)propyl)-6-chloro-4-methylthiazolo[4,5-c]pyridin-2-amine (0.060 g, 0.195 mmol) and 2-furoic acid (0.066 g, 0.585 mmol) in ethyl acetate (0.5 mL) and pyridine (0.25 mL) was added T3P (0.696 mL, 50% wt in ethyl acetate, 1.17 mmol). The mixture was stirred at room temperature overnight and then heated at 50° C. for 48 h. The resulting mixture was cooled to room temperature, quenched by the addition of water. The aqueous layer was extracted into ethyl acetate. The pH of the aqueous layer was carefully adjusted to ~7 with 0.5 N NaOH. The aqueous layer was again extracted with ethyl acetate. The organic layers concentrated under reduced pressure and subjected to preparative HPLC (RP18 acetonitrile/water w/0.1% TFA) to yield the title compound (0.041 g, 33%) as a white solid. $^1$H NMR (400 MHz, DMSO-$d_6$) δ ppm 8.46 (br s, 1H), 8.09 (d, J=1.0 Hz, 1H), 7.61 (br s, 1H), 7.52 (d, J=3.6 Hz, 1H), 7.36 (br s, 1H), 6.86-6.84 (m, 1H), 4.57-4.53 (m, 2H), 4.36 (t, J=6.5 Hz, 2H), 2.78 (s, 3H), 2.51-2.46 (m, 2H). LCMS: 2.16 min, MS: ES+402.1.

Synthesis of N-{6-chloro-4-methyl-[1,3]thiazolo[4,5-c]pyridin-2-yl}-N-[3-(1H-imidazol-1-yl)propyl]cyclopropanecarboxamide (example 55): Was prepared from cyclopropane carboxylic acid according to the procedure outlined above for 1795. $^1$H NMR (400 MHz, DMSO-$d_6$) δ ppm 8.54 (br s, 1H), 8.03 (s, 1H), 7.63 (br s, 1H), 7.39 (br s, 1H), 4.55-4.51 (m, 2H), 4.34 (t, J=6.7 Hz, 2H), 2.72 (s, 3H), 2.44-2.34 (m, 3H), 1.12-1.10 (m 4H). LCMS: 2.12 min, MS: ES+376.1

Example 2: Biological Activity

S. *Aureus* $MIC_{80}$ determinations in *S. aureus* ATCC25923 or in multidrug-resistant strains AR215, AR217 and AR255. $MIC_{80}$'s were determined by the broth microdilution method recommended by the Clinical and Laboratory Standards Institute (CLSI) in Cation-adjusted Mueller-Hinton broth (CAMHB). (Cao et al., 2018). In the preliminary screening, three compound concentrations were used: 5.8, 20.4, and 71.4 μM; for quantitative MIC80 measurements, a 1.5-fold dilution series of the compounds was prepared in CAMHB. Overnight bacterial culture was added to the diluted compounds in a 96-well plate after adjusting the bacterial concentration to achieve a $5\times10^5$ CFU/mL final concentration. After 16-24 h incubation at 35±2° C., the plates were read at 600 nM in a microplate reader. The $MIC_{80}$ was defined as the concentration of an antibacterial agent that inhibited bacteria growth ≥80% compared to vehicle-treated control cultures. All values were determined at least twice independently, and the average number is reported.

AR215, AR217, and AR222 were obtained from the Centers for Disease Control and Prevention (CDC). AR215 and AR217 are cefoxitin-screen positive (resistant to cefoxitin) and resistant to oxacillin, which are MRSA strains. AR215 is also resistant to clindamycin, erythromycin, levofloxacin, and penicillin. AR217 is also resistant to levofloxacin, penicillin, and Trimethoprim-sulfamethoxazole. AR222 is only resistant to penicillin.

TABLE 1
| MRSA $MIC_{80}$ for Aminobenzothiazole Compounds | | | |
|---|---|---|---|
| Example No. | Compound ID | Structure | ATCC 25923 $MIC_{80}$ (μM) |
| 1 | 1491 | 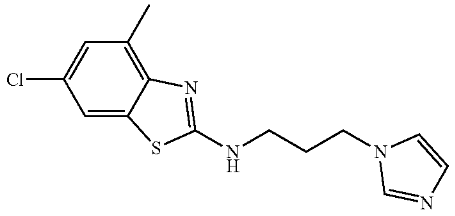 [SMILES: Cc1cc(Cl)cc2sc(NCCCn3ccnc3)nc12] | 19.8 |
| 2 | 1395 | 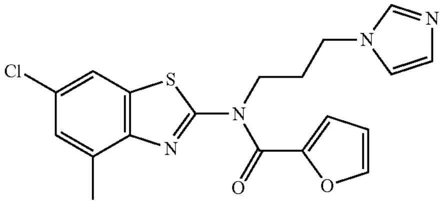 [SMILES: Cc1cc(Cl)cc2sc(N(CCCn3ccnc3)C(=O)c3ccco3)nc12] | 1.7 |
| 3 | 1482 | 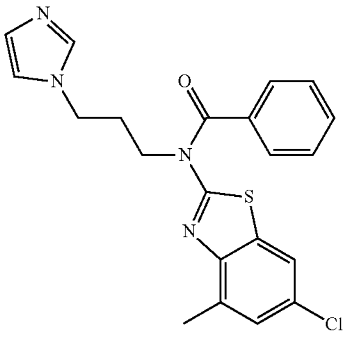 [SMILES: Cc1cc(Cl)cc2sc(N(CCCn3ccnc3)C(=O)c3ccccc3)nc12] | 3.9 |
| 4 | 1483 | 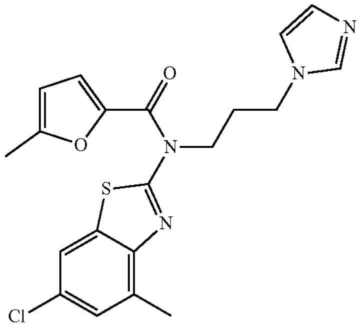 | 2.6 |
| 5 | 1484 | 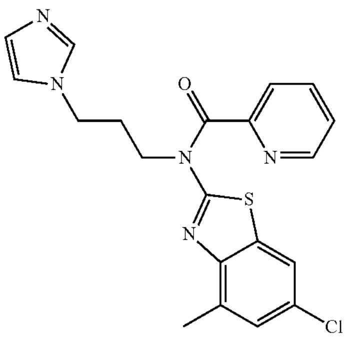 [SMILES: Cc1cc(Cl)cc2sc(N(CCCn3ccnc3)C(=O)c3ccccn3)nc12] | 8.8 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 6 | 1485 | 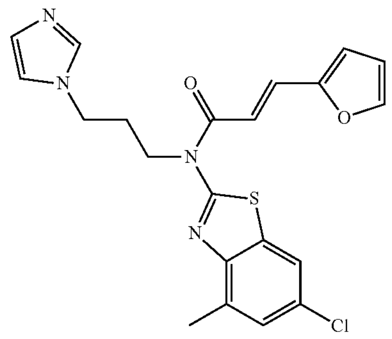 [SMILES: Cc1cc(Cl)cc2sc(N(CCCn3ccnc3)C(=O)/C=C/c3ccco3)nc12] | 2.6 |
| 7 | 1486 | 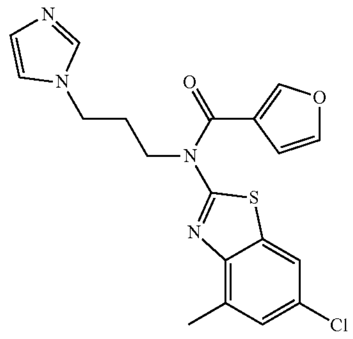 [SMILES: Cc1cc(Cl)cc2sc(N(CCCn3ccnc3)C(=O)c3ccoc3)nc12] | 2.6 |
| 8 | 1487 | 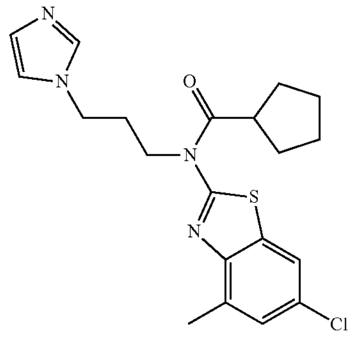 [SMILES: Cc1cc(Cl)cc2sc(N(CCCn3ccnc3)C(=O)C3CCCC3)nc12] | 3.9 |
| 9 | 1494 | 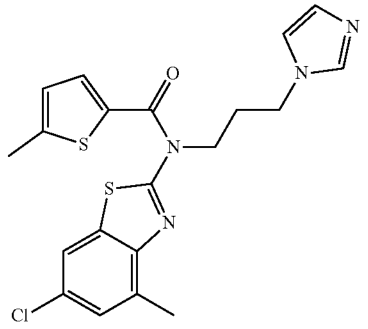 [SMILES: Cc1ccc(C(=O)N(CCCn2ccnc2)c2nc3c(C)cc(Cl)cc3s2)s1] | 2.6 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 10 | 1510 | 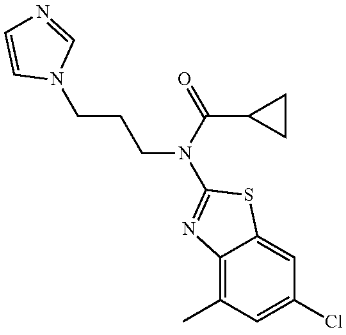 [SMILES: Cc1cc(Cl)cc2sc(N(CCCn3ccnc3)C(=O)C3CC3)nc12] | 1.7 |
| 11 | 1511 | 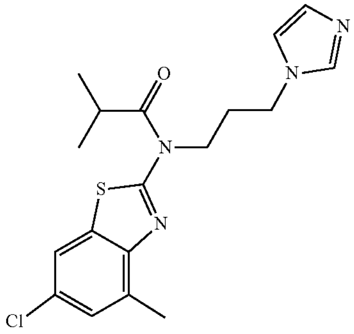 [SMILES: Cc1cc(Cl)cc2sc(N(CCCn3ccnc3)C(=O)C(C)C)nc12] | 2.7 |
| 12 | 1596 | 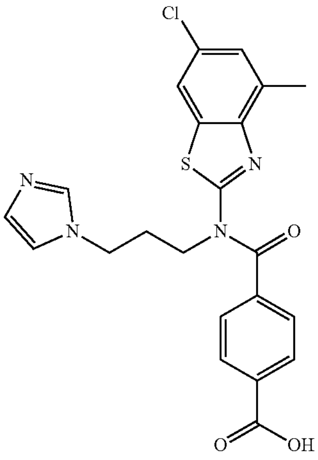 [SMILES: Cc1cc(Cl)cc2sc(N(CCCn3ccnc3)C(=O)c3ccc(C(=O)O)cc3)nc12] | >100 |
| 13 | 1598 | 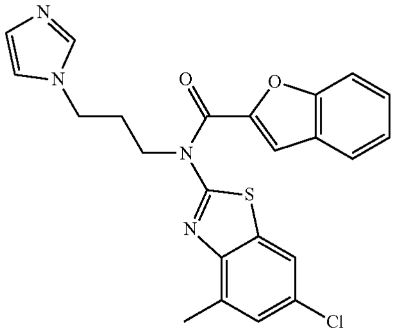 [SMILES: Cc1cc(Cl)cc2sc(N(CCCn3ccnc3)C(=O)c3cc4ccccc4o3)nc12] | 8.8 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 14 | 1599 | 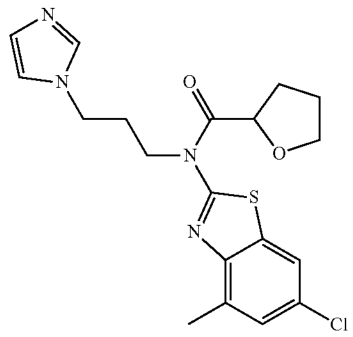 [SMILES: Cc1cc(Cl)cc2sc(N(CCCn3ccnc3)C(=O)C3CCCO3)nc12] | 29.6 |
| 15 | 1600 | 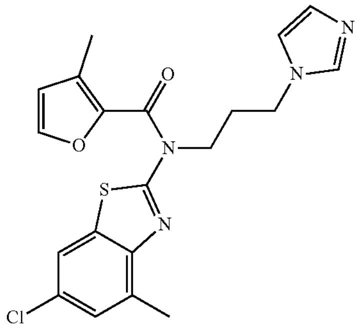 [SMILES: Cc1ccoc1C(=O)N(CCCn1ccnc1)c1nc2c(C)cc(Cl)cc2s1] | <1.7 |
| 16 | 1601 | 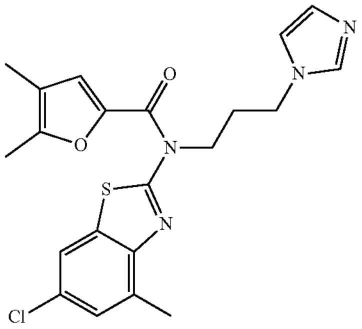 [SMILES: Cc1cc(C(=O)N(CCCn2ccnc2)c2nc3c(C)cc(Cl)cc3s2)oc1C] | 3.9 |
| 17 | 1602 | 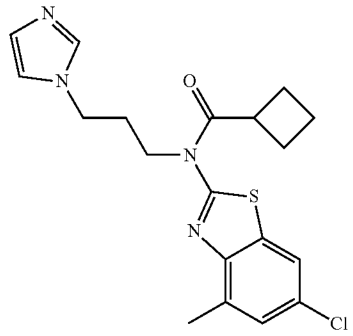 [SMILES: Cc1cc(Cl)cc2sc(N(CCCn3ccnc3)C(=O)C3CCC3)nc12] | 2.6 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 18 | 1603 | 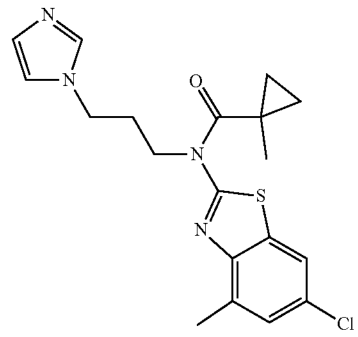 [SMILES: Cc1cc(Cl)cc2sc(N(CCCn3ccnc3)C(=O)C3(C)CC3)nc12] | 5.9 |
| 19 | 1639 | 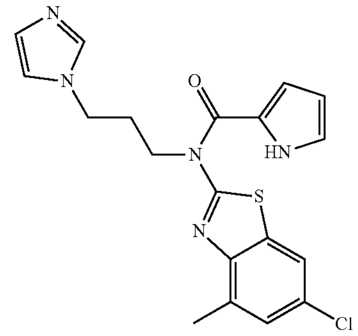 [SMILES: Cc1cc(Cl)cc2sc(N(CCCn3ccnc3)C(=O)c3ccc[nH]3)nc12] | 1.3 |
| 20 | 1640 | 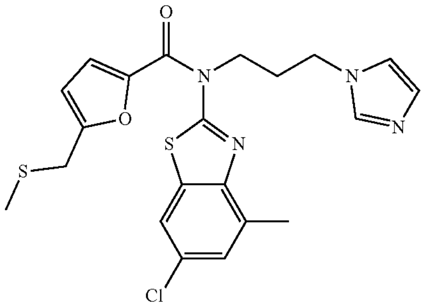 [SMILES: CSCc1ccc(C(=O)N(CCCn2ccnc2)c2nc3c(C)cc(Cl)cc3s2)o1] | 2.9 |
| 21 | 1641 | 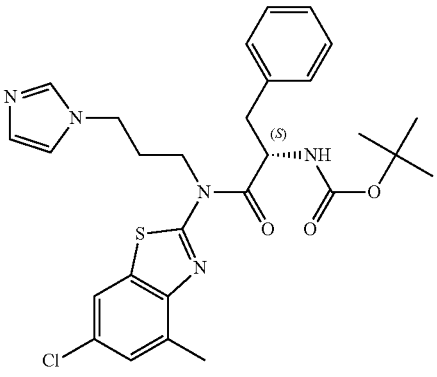 | 14.8 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 22 | 1488 | 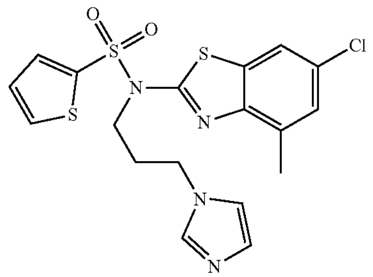 [SMILES: Cc1cc(Cl)cc2sc(N(CCCn3ccnc3)S(=O)(=O)c3cccs3)nc12] | 3.9 |
| 23 | 1490 | 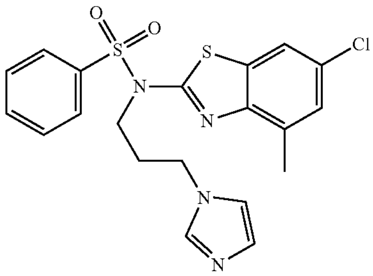 [SMILES: Cc1cc(Cl)cc2sc(N(CCCn3ccnc3)S(=O)(=O)c3ccccc3)nc12] | 3.9 |
| 24 | 1493 | 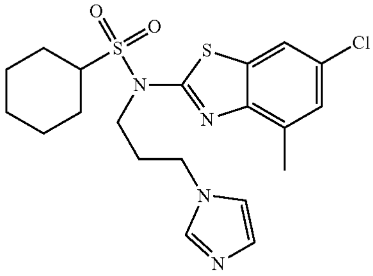 [SMILES: Cc1cc(Cl)cc2sc(N(CCCn3ccnc3)S(=O)(=O)C3CCCCC3)nc12] | 13.2 |
| 25 | 1495 | 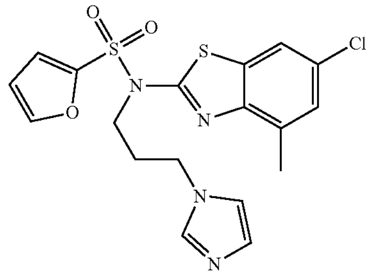 [SMILES: Cc1cc(Cl)cc2sc(N(CCCn3ccnc3)S(=O)(=O)c3ccco3)nc12] | 8.8 |
| 26 | 1489 | 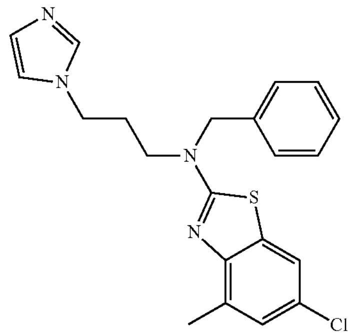 [SMILES: Cc1cc(Cl)cc2sc(N(CCCn3ccnc3)Cc3ccccc3)nc12] | 3.9 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 27 | 1642 | 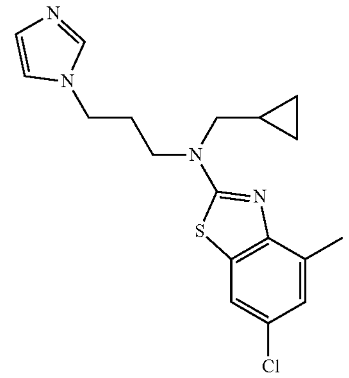 [SMILES: Cc1cc(Cl)cc2sc(N(CCCn3ccnc3)CC3CC3)nc12] | 6.6 |
| 28 | 1666 | 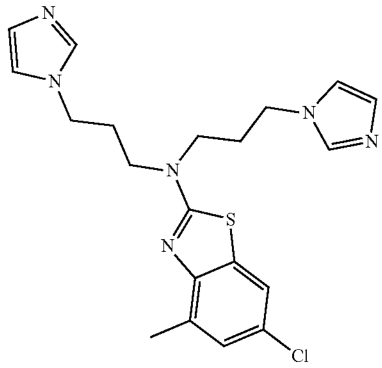 [SMILES: Cc1cc(Cl)cc2sc(N(CCCn3ccnc3)CCCn3ccnc3)nc12] | 5.9 |
| 29 | 1604 | 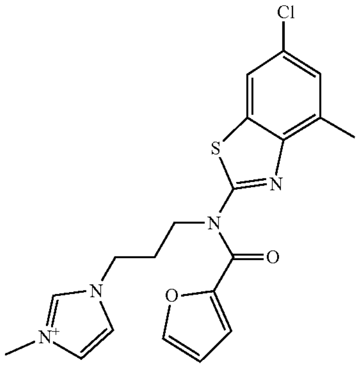 | 13.2 |
| 30 | 1725 | 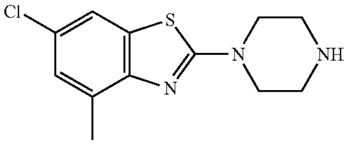 [SMILES: Cc1cc(Cl)cc2sc(N3CCNCC3)nc12] | 100 |
| 31 | 1674 | 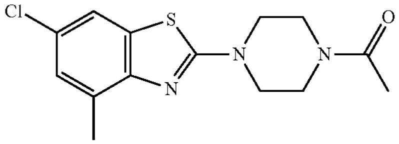 [SMILES: CC(=O)N1CCN(c2nc3c(C)cc(Cl)cc3s2)CC1] | >100 |

TABLE 1-continued
MRSA $MIC_{80}$ for Aminobenzothiazole Compounds
| Example No. | Compound ID | Structure | ATCC 25923 $MIC_{80}$ (μM) |
|---|---|---|---|
| 32 | 1675 | 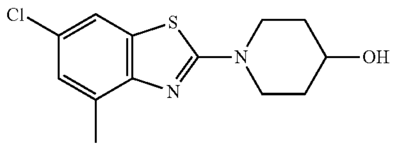 [SMILES: Cc1cc(Cl)cc2sc(N3CCC(O)CC3)nc12] | >100 |
| 33 | 1726 | 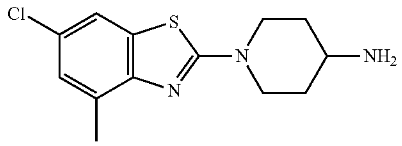 [SMILES: Cc1cc(Cl)cc2sc(N3CCC(N)CC3)nc12] | 66.7 |
| 34 | 1727 | 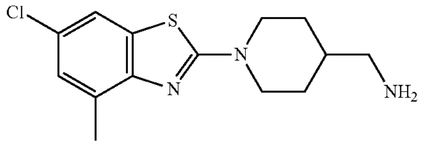 [SMILES: Cc1cc(Cl)cc2sc(N3CCC(CN)CC3)nc12] | 44.4 |
| 35 | 1756 | 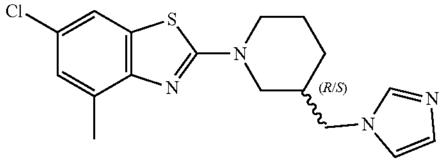 [SMILES: Cc1cc(Cl)cc2sc(N3CCCC(Cn4ccnc4)C3)nc12] | 66.7 |
| 36 | 1752 | 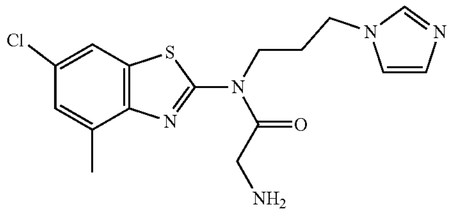 [SMILES: Cc1cc(Cl)cc2sc(N(CCCn3ccnc3)C(=O)CN)nc12] | >100 |
| 37 | 1737 | 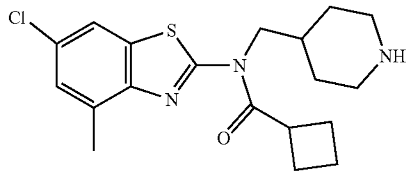 [SMILES: Cc1cc(Cl)cc2sc(N(CC3CCNCC3)C(=O)C3CCC3)nc12] | 19.8 |
| 38 | 1757 | 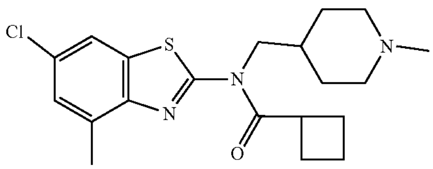 [SMILES: Cc1cc(Cl)cc2sc(N(CC3CCN(C)CC3)C(=O)C3CCC3)nc12] | >100 |
| 39 | 1729 | 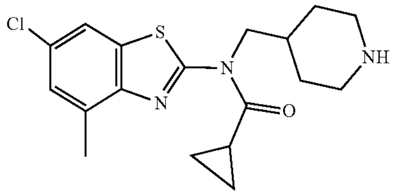 [SMILES: Cc1cc(Cl)cc2sc(N(CC3CCNCC3)C(=O)C3CC3)nc12] | 19.8 |

TABLE 1-continued
MRSA $MIC_{80}$ for Aminobenzothiazole Compounds
| Example No. | Compound ID | Structure | ATCC 25923 $MIC_{80}$ (μM) |
|---|---|---|---|
| 40 | 1740 | 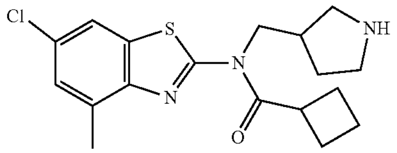 [SMILES: Cc1cc(Cl)cc2sc(N(CC3CCNC3)C(=O)C3CCC3)nc12] | 29.6 |
| 41 | 1736 | 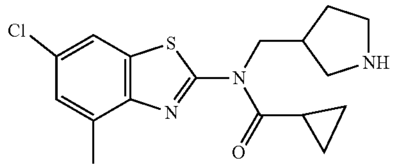 [SMILES: Cc1cc(Cl)cc2sc(N(CC3CCNC3)C(=O)C3CC3)nc12] | 44.4 |
| 42 | 1790 | 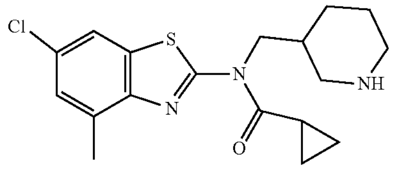 [SMILES: Cc1cc(Cl)cc2sc(N(CC3CCCNC3)C(=O)C3CC3)nc12] | 66.7 |
| 43 | 1791 | 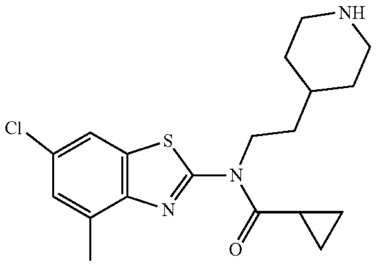 [SMILES: Cc1cc(Cl)cc2sc(N(CCC3CCNCC3)C(=O)C3CC3)nc12] | 100 |
| 44 | 1788 | 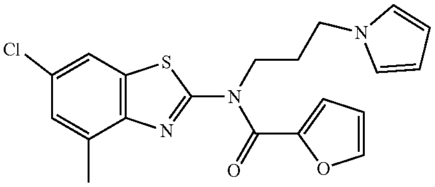 [SMILES: Cc1cc(Cl)cc2sc(N(CCCn3cccc3)C(=O)c3ccco3)nc12] | >100 |
| 45 | 1796 | 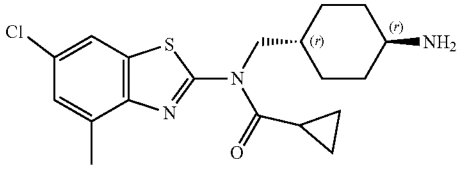 [SMILES: Cc1cc(Cl)cc2sc(N(C[C@H]3CC[C@H](N)CC3)C(=O)C3CC3)nc12] | 19.8 |
| 46 | 1755 | 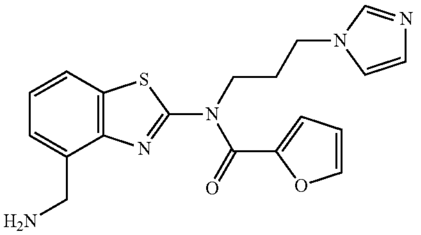 [SMILES: NCc1cccc2sc(N(CCCn3ccnc3)C(=O)c3ccco3)nc12] | >100 |

TABLE 1-continued
| MRSA MIC$_{80}$ for Aminobenzothiazole Compounds | | | |
|---|---|---|---|
| Example No. | Compound ID | Structure | ATCC 25923 MIC$_{80}$ (μM) |
| 47 | 1754 | 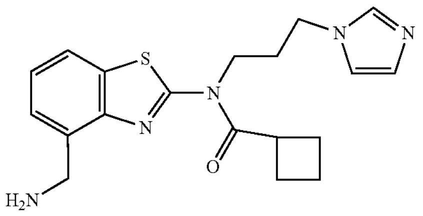 [SMILES: NCc1cccc2sc(N(CCCn3ccnc3)C(=O)C3CCC3)nc12] | >100 |
| 48 | 1753 | 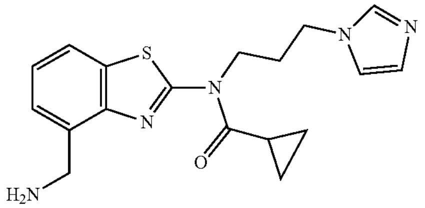 [SMILES: NCc1cccc2sc(N(CCCn3ccnc3)C(=O)C3CC3)nc12] | >100 |
| 49 | 1734 | 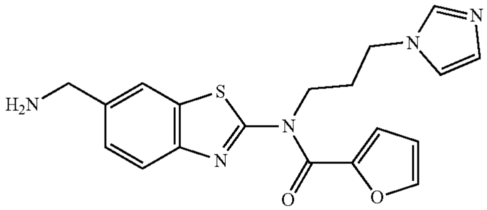 [SMILES: NCc1ccc2nc(N(CCCn3ccnc3)C(=O)c3ccco3)sc2c1] | >100 |
| 50 | 1735 | 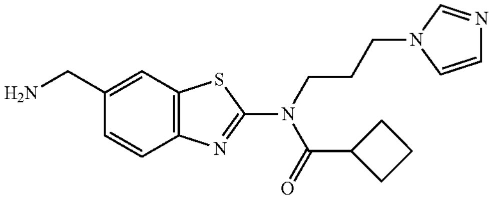 [SMILES: NCc1ccc2nc(N(CCCn3ccnc3)C(=O)C3CCC3)sc2c1] | >100 |
| 51 | 1728 | 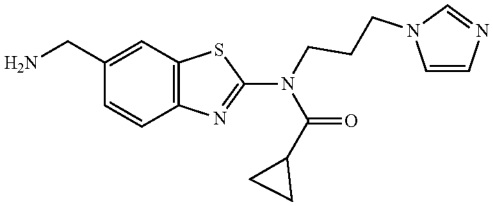 [SMILES: NCc1ccc2nc(N(CCCn3ccnc3)C(=O)C3CC3)sc2c1] | >100 |
| 52 | 1789 | 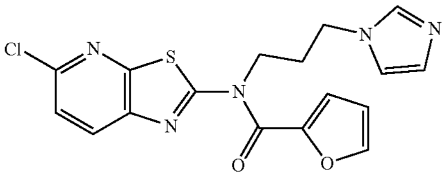 [SMILES: O=C(c1ccco1)N(CCCn1ccnc1)c1nc2ccc(Cl)nc2s1] | >100 |
| 53 | 1794 | 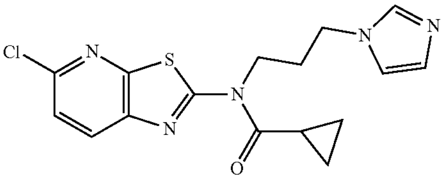 [SMILES: O=C(C1CC1)N(CCCn1ccnc1)c1nc2ccc(Cl)nc2s1] | >100 |

TABLE 1-continued
| MRSA $MIC_{80}$ for Aminobenzothiazole Compounds | | | |
|---|---|---|---|
| Example No. | Compound ID | Structure | ATCC 25923 $MIC_{80}$ (μM) |
| 54 | 1795 | 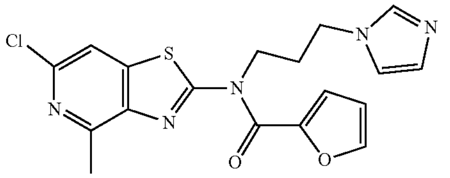 [SMILES: Cc1nc(Cl)cc2sc(N(CCCn3ccnc3)C(=O)c3ccco3)nc12] | >100 |
| 55 | 1797 | 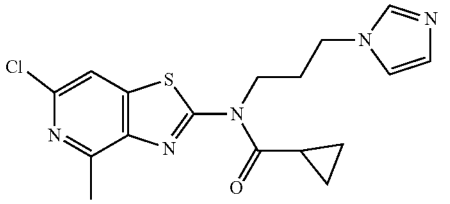 [SMILES: Cc1nc(Cl)cc2sc(N(CCCn3ccnc3)C(=O)C3CC3)nc12] | 100 |
| 56 | 1741 | 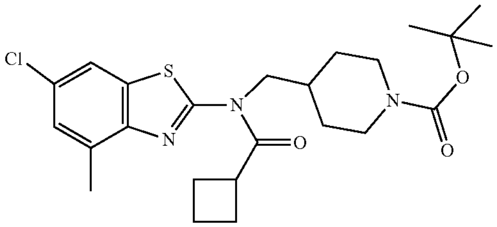 [SMILES: Cc1cc(Cl)cc2sc(N(CC3CCN(C(=O)OC(C)(C)C)CC3)C(=O)C3CCC3)nc12] | >100 |
| 57 | 1694 | 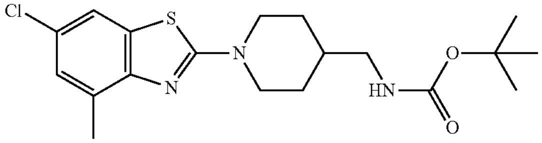 [SMILES: Cc1cc(Cl)cc2sc(N3CCC(CNC(=O)OC(C)(C)C)CC3)nc12] | >100 |
| 58 | 1693 | 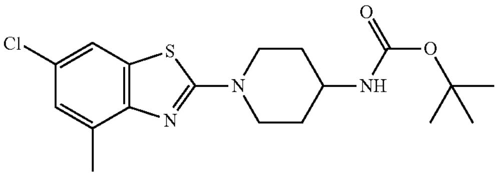 [SMILES: Cc1cc(Cl)cc2sc(N3CCC(NC(=O)OC(C)(C)C)CC3)nc12] | >100 |
| 59 | 1673 | 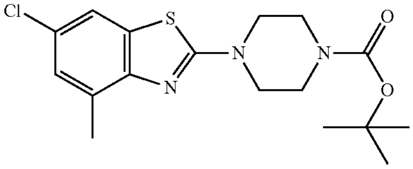 [SMILES: Cc1cc(Cl)cc2sc(N3CCN(C(=O)OC(C)(C)C)CC3)nc12] | >100 |
| 60 | 1792 | 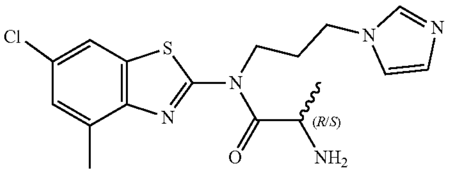 [SMILES: Cc1cc(Cl)cc2sc(N(CCCn3ccnc3)C(=O)C(C)N)nc12] | >100 |
| 61 | 1739 | 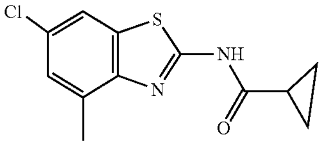 [SMILES: Cc1cc(Cl)cc2sc(NC(=O)C3CC3)nc12] | >100 |

TABLE 1-continued

| MRSA $MIC_{80}$ for Aminobenzothiazole Compounds | | | |
|---|---|---|---|
| Example No. | Compound ID | Structure | ATCC 25923 $MIC_{80}$ (μM) |
| 62 | 1595 | 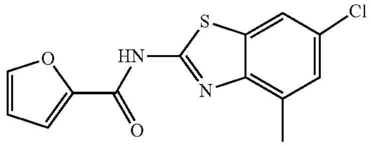 [SMILES: Cc1cc(Cl)cc2sc(NC(=O)c3ccco3)nc12] | >100 |

TABLE 2

MIC$_{80}$ on *S. aureus* ATCC 25923, MRSA and other multi-drug resistant strains for compound 1483 and 1600.

| | Resistance | ANTIBIOTICS | | | | | | | | | | | | | COMPOUNDS (μM) | | Control (μM) |
|---|---|---|---|---|---|---|---|---|---|---|---|---|---|---|---|---|---|
| *S. aureus* | Mechanisms | FOX | CLI | DAP | ERY | GEN | LVX | LZD | OXA | P | RIF | TET | SXT | VAN | 1483 | 1600 | clorofloxacin |
| ATCC 25923 | | Neg | S | S | S | S | S | S | S | | S | S | S | S | 0.78 | 1.8 | 40.52 |
| AR215 | aadD, blaZ, arm(A), mecA, spc | R | R | NS | R | S | R | S | R | R | S | S | S | I | 8.9 | 13.3 | .66 |
| AR217 | blaZ, dfrG, mecA | R | S | NS | S | S | R | S | R | R | S | S | R | I | 5.9 | 4 | .30 |
| AR222 | blaZ | S | S | S | S | S | S | S | S | R | I | S | S | I | 0.78 | 2.6 | 0.52 |

R: resistance; S: sensitive; I: intermediate.
Cefoxitin (FOX);
Clindamycin (CLI);
Daptomycin (DAP);
Erythromycin (ERY);
Gentamicin (GEN);
Levofloxacin (LVX);
Linezolid (LZD);
Oxacillin (OXA);
Penicillin (P);
Rifampin (RIF);
Tetracycline (TET);
Trimethoprim-sulfamethoxazole (SXT);
Vancomycin (VAN)

All of the compounds, formulations, and methods disclosed and claimed herein can be made and executed without undue experimentation in light of the present disclosure. While the compounds, formulations, and methods of this invention have been described in terms of preferred embodiments, it will be apparent to those of skill in the art that variations may be applied to the compounds, formulations, and methods, as well as in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Anderson, *Practical Process Research & Development—A Guide for Organic Chemists*, 2nd ed., Academic Press, New York, 2012.
Cao et al., *ACS Omega*, 3(11):15125-133, 2018.
*Handbook of Pharmaceutical Salts: Properties, and Use*, Stahl and Wermuth Eds., Verlag Helvetica Chimica Acta, 2002.
Kavanagh, *Antimicrobial Resistance & Infection Control*, 8:103, 2019.
Peeters et al., *Infect. Drug Resist.*, 12:329-343, 2019.
Smith, *March's Advanced Organic Chemistry: Reactions, Mechanisms, and Structure*, 7th Ed., Wiley, 2013.
Umei et al., *Bioorg & Med. Chem.*, 25(13):3406-3430, 2017.
von Bubnoff, *Cell*, 127(5):867-869, 2006.
WO 2017/220431
Wright et al., *Angew Chem. Int. Ed.*, 53(34):8840-8869, 2014.

What is claimed is:

1. A compound of the formula:

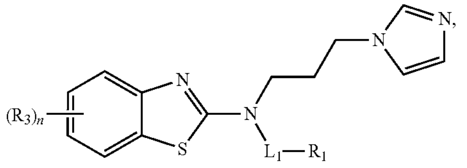

(II)

wherein:

n is 0, 1, 2, 3, or 4;

$L_1$ is —C(O)— or —S(O)$_2$—; or $L_1$ and $R_1$ are taken together and are an amino acid residue or a monoprotected amino acid residue;

$R_1$ is alkyl$_{(C\leq12)}$, cycloalkyl$_{(C\leq12)}$, heterocycloalkyl$_{(C\leq12)}$, aralkyl$_{(C\leq12)}$, heteroaralkyl$_{(C\leq12)}$, or a substituted version of any one of these groups; or $R_1$ and $L_1$ are taken together and is as defined above; and $R_3$ is, in each instance independently, amino, cyano, halo, hydroxy, or nitro; or alkyl$_{(C\leq12)}$, cycloalkyl$_{(C\leq12)}$, heterocycloalkyl$_{(C\leq12)}$, aryl$_{(C\leq12)}$, heteroaryl$_{(C\leq12)}$, alkoxy$_{(C\leq12)}$, alkylamino$_{(C\leq12)}$, dialkylamino$_{(C\leq12)}$, or a substituted version of any one of these groups;

provided the compound is not N-(3-(1H-imidazol-1-yl) propyl)-N-(6-chloro-4-methylbenzo[d]thiazol-2-yl) furan-2-carboxamide;

or a pharmaceutically acceptable salt thereof.

2. The compound of claim 1, wherein the compound is further defined:

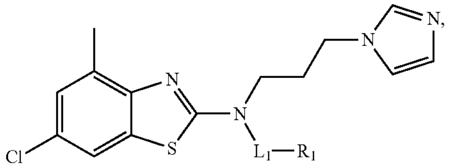

(III)

wherein:

$L_1$ is —C(O)— or —S(O)$_2$—; or $L_1$ and $R_1$ are taken together and is an amino acid residue or a monoprotected amino acid residue; and $R_1$ is alkyl$_{(C\leq12)}$, cycloalkyl$_{(C\leq12)}$, heterocycloalkyl$_{(C\leq12)}$, aralkyl$_{(C\leq12)}$, heteroaralkyl$_{(C\leq12)}$, or a substituted version of any one of these groups; or $R_1$ and $L_1$ are taken together and is as defined above;

provided the compound is not N-(3-(1H-imidazol-1-yl) propyl)-N-(6-chloro-4-methylbenzo[d]thiazol-2-yl) furan-2-carboxamide;

or a pharmaceutically acceptable salt thereof.

3. The compound of claim 1, wherein $L_1$ is —C(O)—.

4. The compound of claim 1, wherein $L_1$ is —S(O)$_2$—.

5. The compound of claim 1, wherein $L_1$ and $R_1$ are taken together and is a monoprotected amino acid residue.

6. The compound of claim 5, wherein $L_1$ and $R_1$ are taken together and is N-Boc-phenylalanine.

7. The compound of claim 1, wherein $R_1$ is alkyl$_{(C\leq12)}$.

8. The compound of claim 1, wherein $R_1$ is cycloalkyl$_{(C\leq12)}$.

9. The compound of claim 1, wherein $R_1$ is heterocycloalkyl$_{(C\leq12)}$.

10. The compound of claim 1, wherein the compound is further defined as:

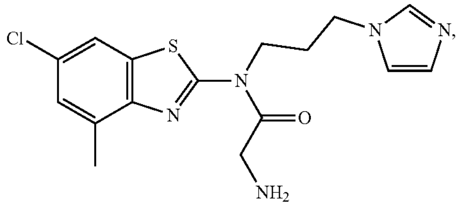

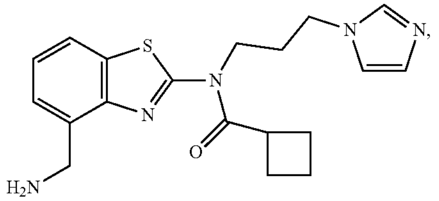

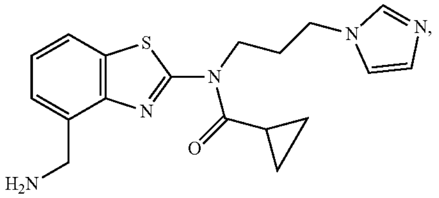

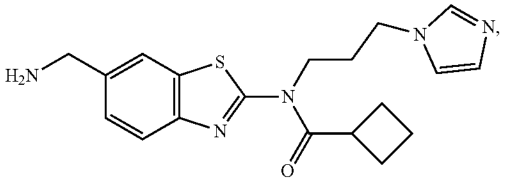

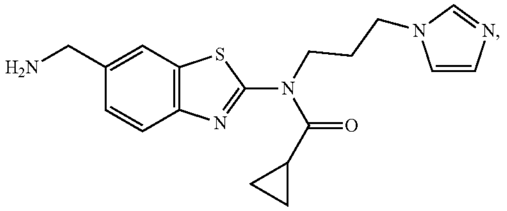

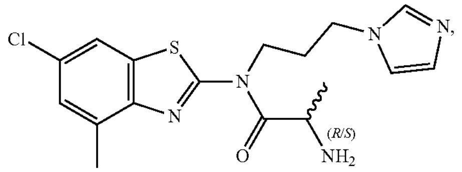

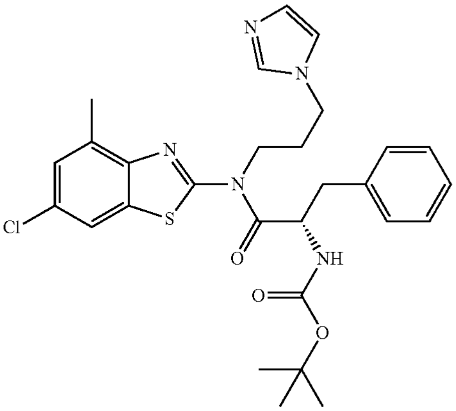

,

-continued

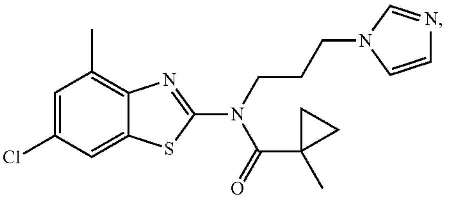

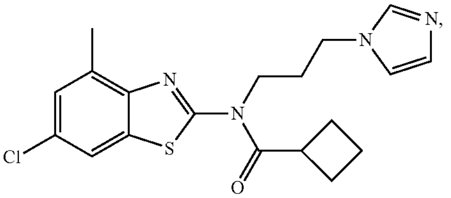

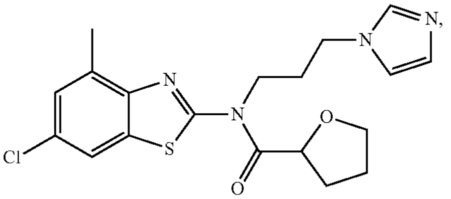

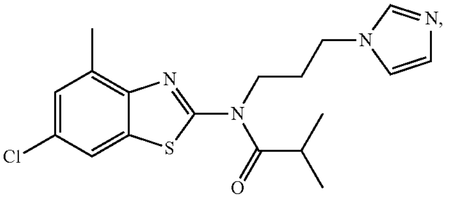

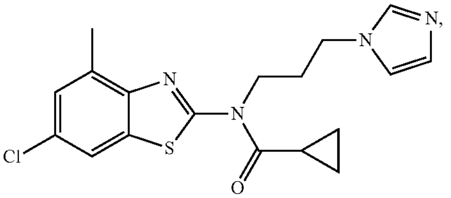

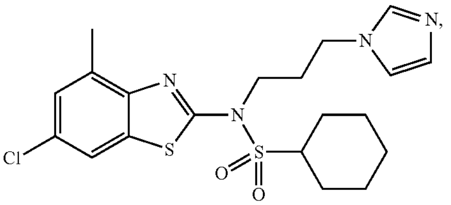

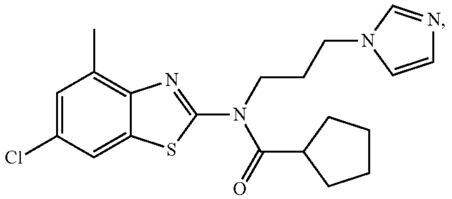

or

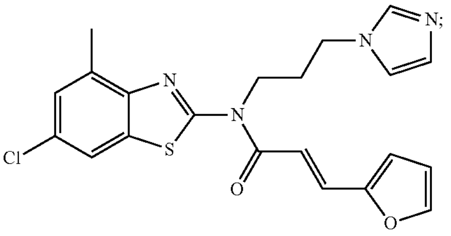 [SMILES: Cc1cc(Cl)cc2sc(N(CCCn3ccnc3)C(=O)/C=C/c3ccco3)nc12]

or a pharmaceutically acceptable salt thereof.

11. A compound of the formula:

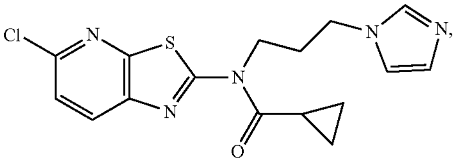

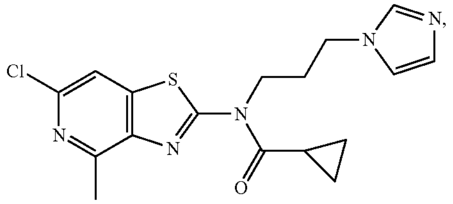

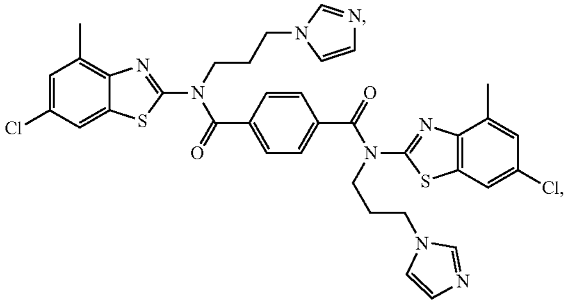

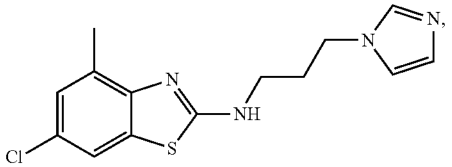

or

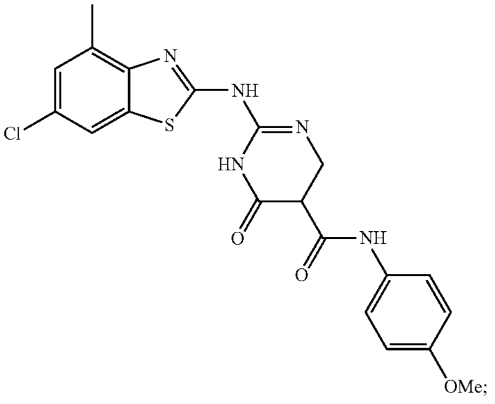

or a pharmaceutically acceptable salt thereof.

12. A pharmaceutical composition comprising:

a) a compound of claim 1; and b) an excipient or a pharmaceutically acceptable carrier.

13. A method of treating a disease or disorder associated with gram-positive bacteria in a patient in need thereof comprising administering to the patient a therapeutically effective amount of N-(3-(1H-imidazol-1-yl)propyl)-N-(6-chloro-4-methylbenzo[d]thiazol-2-yl)furan-2-carboxamide or a compound of claim 1.

14. A method of inhibiting gram-positive bacteria comprising contacting the bacteria with an effective amount of N-(3-(1H-imidazol-1-yl)propyl)-N-(6-chloro-4-methylbenzo[d]thiazol-2-yl)furan-2-carboxamide or a compound of claim 1.

* * * * *